(12) United States Patent
Jensen et al.

(10) Patent No.: US 7,850,965 B2
(45) Date of Patent: Dec. 14, 2010

(54) ANTI-ORTHOPOXVIRUS RECOMBINANT POLYCLONAL ANTIBODY

(75) Inventors: Allan Jensen, Fredensborg (DK); Johan Lantto, Lund (SE); Margit Haahr Hansen, Copenhagen (DK); Lone Kjær Rasmussen, Skodsborg (DK); Søren Kofoed Rasmussen, Roskilde (DK); Lucilla Steinaa, Hørsholm (DK)

(73) Assignee: Symphogen A/S, Lyngby (DK)

( * ) Notice: Subject to any disclaimer, the term of this patent is extended or adjusted under 35 U.S.C. 154(b) by 556 days.

(21) Appl. No.: 11/633,070

(22) Filed: Dec. 4, 2006

(65) Prior Publication Data
US 2008/0069822 A1    Mar. 20, 2008

(30) Foreign Application Priority Data
Dec. 5, 2005   (DK) .............................. 2005 01720

(51) Int. Cl.
*A61K 39/00* (2006.01)
*A61K 39/42* (2006.01)
*C07K 16/08* (2006.01)

(52) U.S. Cl. .............. 424/133.1; 424/159.1; 530/387.3; 530/389.4

(58) Field of Classification Search ........................ None
See application file for complete search history.

(56) References Cited

U.S. PATENT DOCUMENTS

| | | | |
|---|---|---|---|
| 6,451,309 B2 | 9/2002 | Hooper et al. | |
| 6,562,376 B2 * | 5/2003 | Hooper et al. | .............. 424/489 |
| 6,783,759 B2 | 8/2004 | Rosengard | |
| 2005/0129700 A1 | 6/2005 | Rosengard | |
| 2006/0275766 A1 | 12/2006 | Haurum et al. | |
| 2007/0141048 A1 | 6/2007 | Oleksiewicz et al. | |

FOREIGN PATENT DOCUMENTS

| | | |
|---|---|---|
| WO | WO 03/049117 A2 | 6/2003 |
| WO | WO 03/068151 A2 | 8/2003 |
| WO | WO 2004/061104 A2 | 7/2004 |
| WO | WO 2004/061107 A1 | 7/2004 |
| WO | WO 2005/042774 A2 | 5/2005 |
| WO | WO 2006/007850 A1 | 1/2006 |
| WO | WO 2006/007853 A2 | 1/2006 |
| WO | WO 2007/101441 A1 | 9/2007 |

OTHER PUBLICATIONS

Lustig, et al. Combinations of Polyclonal or Monoclonal Antibodies to Proteins of the Outer Membranes of the Two Infectious Forms of Vaccinia Virus Protect Mice against a Lethal Respiratory Challenge. J. Virol. 2005; 79(21):13454-13462.*

Bregenholt and Haurum Pathogen-specific recombinant human polyclonal antibodies: biodefence application. Expert Opin. Biol Ther. 2004; 4(3):387-396.*

Fogg, et al. Protective Immunity to Vaccinia Virus Induced by Vaccination with Multiple Recombinant Outer Membrane Proteins of Intracellular and Extracellular Virion. J. Virol. 2004; 78(19):10230-10237.*

(Continued)

*Primary Examiner*—Mary E Mosher
*Assistant Examiner*—Stuart W Snyder
(74) *Attorney, Agent, or Firm*—Sterne, Kessler, Goldstein & Fox P.L.L.C.

(57) ABSTRACT

Disclosed is an anti-orthopoxvirus recombinant polyclonal antibody comprising distinct members which in union are capable of binding at least three orthopoxvirus related antigens, a pharmaceutical composition comprising the antibody, and a method for its production. Also disclosed is a polyclonal cell line capable of producing the recombinant polyclonal antibody as therapeutic methods utilizing the polyclonal antibody. Finally, the invention also pertains to a method for screening for useful $V_H$ and $V_L$ pairs useful when preparing the polyclonal antibody.

6 Claims, 15 Drawing Sheets

OTHER PUBLICATIONS

Isaacs, et al. Restoration of Complement-Enhanced Neutralization of Vaccinia Virus Virions by Novel Monoclonal Antibodies Raised against the Vaccinia Virus Complement Control Protein. J Virol. 2003; 77(15): 8256-8262.*

Schmaljohn, et al. Production and Characterization of Human Monoclonal Antibody Fab Fragments to Vaccinia Virus from a Phage-Display Combinatorial Library. Virol. 1999; 258:189-200.*

Watts and Lanzavecchia. Suppressive Effect of Antibody on Processing of T Cell Epitopes. J. Exp. Med. 1993; 178:1459-1463.*

Nowak, MA.Immune responses against multiple epitopes: a theory for immunodominance and antigenic variation. Sem. Virol. 1996. 7:83-92.*

Schmaljohn, C., et al., "Production and Characterization of Human Monoclonal Antibody Fab Fragments to Vaccinia Virus from a Phage-Display Combinatorial Library," *Virology* 258:189-200, Academic Press (1999).

Boulter, E.A., and Appleyard, G., "Differences between Extracellular and Intracellular Forms of Poxvirus and Their Implications," *Prog. Med. Virol. 16*:86-108, Karger (1973).

Chen, N., et al., "Virulence differences between monkeypox virus isolates from West Africa and the Congo basin," *Virology* 340:46-63, Academic Press (Sep. 2005).

Davies, D.H., et al., "Profiling the humoral immune response to infection by using proteome microarrays: High-throughput vaccine and diagnostic antigen discovery," *Proc. Natl. Acad. Sci. U.S.A. 102*:547-552, The National Academy of Sciences (Jan. 2005).

Demkowicz, W.E., et al., "Identification and Characterization of Vaccinia Virus Genes Encoding Proteins That are Highly Antigenic in Animals and Are Immunodominant in Vaccinated Humans," *J. Virol. 66*: 386-398, American Society for Microbiology (1992).

Fogg, C., et al., "Protective Immunity to Vaccinia Virus Induced by Vaccination with Multiple Recombinant Outer Membrane Proteins of Intracellular and Extracellular Virions," *J. Virol. 78*:10230-10237, American Society for Microbiology (Oct. 2004).

Galmiche, M.C., et al., "Neutralizing and Protective Antibodies Directed against Vaccinia Virus Envelope Antigens," *Virology 254*:71-80, Academic Press (1999).

Gordon, J., et al., "A Prominent Antigenic Surface Polypeptide Involved in the Biogenesis and Function of the Vaccinia Virus Envelope," *Virology 18*:671-686, Academic Press, Inc. (1991).

Hooper, J.W., et al., "DNA Vaccination with Vaccinia Virus L1R and A33R Genes Protects Mice against a lethal Poxvirus Challenge," *Virology 266*:329-339 (2000).

Hooper, J.W., et al., "Four-gene-combination DNA vaccine protects mice against a lethal vaccinia virus challenge and elicits appropriate antibody responses in nonhuman primates," *Virology 306*:181-195, Elsevier Science (2003).

Issacs, S.N., et al., "Restoration of Complement-Enhanced Neutralization of Vaccinia Virus Virions by Novel Monoclonal Antibodies Raised against the Vaccinia Virus Complement Control Protein," *J. Virol. 77*:8256-8262, American Society for Microbiology (2003).

Lai, C., et al., "The Purified 14-Kilodalton Envelope Protein of Vaccinia Virus Produced in *Escherichia coli* Induces Virus Immunity in Animals," *J. Virol. 65*:5631-5635, American Society for Microbiology (1991).

Law, M., and Smith, G.L., "Antibody Neutralization of the Extracellular Enveloped Form of Vaccinia Virus," *Virology 280*:132-142, Academic Press (2001).

Lin, C-L., et al., "Vaccinia Virus Envelope H3L Protein Binds to Cell Surface Heparan Sulfate and Is Important for Intracellular Mature Virion Morphogenesis and Virus Infection In Vitro and In Vivo," *J. Virol. 74*:3353-3365, American Society for Microbiology (2000).

Lustig, S., et al., "Combinations of Polyclonal or Monoclonal Antibodies to Proteins of the Outer Membranes of the Two Infectious Forms of Vaccinia Virus Protect Mice against a Lethal Respiratory Challenge," *J. Virol. 79*:13454-13462, American Society for Microbiology (Nov. 2005).

Mullick, J., et al., "Herpes and pox viral complement control proteins: 'the mask of self'," *Trend Immunol. 24*:500-507, Elsevier Ltd. (2003).

Ramirez, J.C., et al., "Administration to mice of monoclonal antibody that neutralizes the intracellular mature virus form of vaccinia virus limits virus replication efficiently under prophylactic and therapeutic conditions," *J. Gen. Virol. 83*:1059-1067, Society for General Microbiology (2002).

Rodriguez, J.F., et al., "Isolation and Characterization of Neutralizing Monoclonal Antibodies of Vaccinia Virus," *J. Virol. 56*:482-488, American Society for Microbiology (1985).

Wallengren, K., et al., "The A17L Gene Product of Vaccinia Virus Is Exposed on the Surface of IMV," *Virology 290*:143-152, Academic Press (2001).

Wolffe, E.J., et al., "A Myristylated Membrane Protein Encoded by the Vaccinia Virus L1R Open Reading Frame Is the Target of Potent Neutralizing Monoclonal Antibodies," *Virology 21*:53-63, Academic Press, Inc. (1995).

Dialog English abstract for WO 2004-061107 A1, 2 pages, accessed on May 2007 (Document FP3 listed on accompanying PTO/SB/08A).

Law, M., et al., "An investigation of the therapeutic value of vaccinia-immune IgG in a mouse pneumonia model," *J. Gen. Virol. 86*:991-1000, SGM (Apr. 2005).

Co-pending U.S. Appl. No. 11/632,937, inventors Rasmussen, S.K., et al., filed Jan. 19, 2007 (Not Published).

Co-pending U.S. Appl. No. 11/658,201, inventors Rasmussen, L.K., et al., filed Jan. 22, 2007 (Not Published).

Co-pending U.S. Appl. No. 11/792,927, inventors Lantto, J., et al., filed Jun. 13, 2007 (Not Published).

Co-pending U.S. Appl. No. 11/658,021, inventors Rasmussen, L.K., et al., filed Jan. 22, 2007 (Not Published).

Gordon, J., et al., "A Prominent Antigenic Surface Polypeptide Involved in the Biogenesis and Function of the Vaccinia Virus Envelope," *Virology 181*:671-686, Academic Press, Inc. (1991).

Bregenholt, S., and Haurum, J., "Pathogen-specific recombinant human polyclonal antibodies: biodefence applications," *Expert Opin. Biol. Ther. 4*:387-396, Ashley Publications Ltd. (Mar. 2004).

Haurum, J., and Bregenholt, S., "Recombinant polyclonal antibodies: Therapeutic antibody technologies come full circle," *IDrugs 8*:404-409, The Thomson Corporation (May 2005).

Tikunova, N.V., et al., "Phage Antibodies Neutralize Vaccinia Virus," *Dokl. Biochem. Biophys. 382*:10-12, Maik "Nauka/Interperiodica" Publishing (2002).

Communication Relating to the Results of the Partial International Search for International Application No. PCT/DK2006/000686, European Patent Office, Netherlands, mailed on Aug. 13, 2007.

Bregenholt, S., et al., "Recombinant Human Polyclonal Antibodies: A New Class of Therapeutic Antibodies Against Viral Infections," *Curr. Pharm. Des. 12*:2007-2015, Bentham Science Publishers Ltd. (Jun. 2006).

Haurum, J.S., "Recombinant polyclonal antibodies: the next generation of antibody therapeutics?" *Drug Disc. Today 11*:655-660, Elsevier Science Publishers (Jul. 2006).

Logtenberg, T., "Antibody cocktails: next-generation biopharmaceuticals with improved potency," *Trends Biotechnol. 25*:390-394, Elsevier Science Publishers (Sep. 2007).

Meijer, P.-J., et al., "Isolation of Human Antibody Repertoires with Preservation of the Natural Heavy and Light Chain Pairing," *J. Mol. Biol. 358*:764-772, Academic Press (May 2006).

Poulsen, T.R., et al., "Kinetic, Affinity, and Diversity Limits of Human Polyclonal Antibody Responses against Tetanus Toxoid," *J. Immunol. 179*:3841-3850, American Association of Immunologists (Sep. 2007).

Sharon, J., et al., "Recombinant Polyclonal Antibodies for Cancer Therapy," *J. Cell. Biochem. 96*:305-313, Wiley-Liss, Inc. (Oct. 2005).

Tolstrup, A.B., et al., "Development of recombinant human polyclonal antibodies for the treatment of complex human diseases," *Expert Opin. Biol. Ther. 6*:905-912, Ashley Publications Limited (Sep. 2006).

Wiberg, F.C., et al., "Production of Target-Specific Recombinant Human Polyclonal Antibodies in Mammalian Cells," *Biotechnol. Bioeng. 94*:396-405, Wiley Periodicals, Inc. (Apr. 2006).

* cited by examiner

Fig. 1

```
              1                                                        50
    VCP-VV    MKVESVTFLT LLGIGCVLSC CTIPSRPINM KFKNSVETDA NAN..YNIGD
  VCP-CMLV    MKVESVTFLT LLGIVCVLSC CTIPSRPINM KFKNSVETYA NTNTNYNIGD
     SPICE    MKVERVTFLT LLGIGCVLSC CTIPSRPINM KFKNSVETDA NAN..YNIGD
       IMP    MKVESVTFLT LLGIGCVLSC CTIPSRPINM KFKNSVGTDA NAN..YNIGD
  VCP-MPXV    MKVESVTFLT LLGIGCVLSY CTIPSRPINM KFKNSVETDA N....YNIGD
 Consensus    MKVEsVTFLT LLGIgCVLSc CTIPSRPINM KFKNSVeTdA N.n..YNIGD 51                                                      100
    VCP-VV    TIEYLCLPGY RKQKMGPIYA KCTGTGWTLF NQCIKRRCPS PRDIDNGQLD
  VCP-CMLV    TIEYLCLPGY RKQKMGPIYA KCTGTGWTLF NQCIKRRCPS PRDIDNGQLD
     SPICE    TIEYLCLPGY RKQKMGPIYA KCTGTGWTLF NQCIKRRCPS PRDIDNGHLD
       IMP    TIEYLCLPGY RKQKMGPIYA KCTGTGWTLF NQCIKRKCPS PRDIDNGQID
  VCP-MPXV    TIEYLCLPGY RKQKMGPIYA KCTGTGWTLF NQCIKRRCPS PRDIDNGQLD
 Consensus    TIEYLCLPGY RKQKMGPIYA KCTGTGWTLF NQCIKRrCPS PRDIDNGqlD 101                                                     150
    VCP-VV    IGGVDFGSSI TYSCNSGYHL IGESKSYCEL GSTGSMVWNP EAPICESVKC
  VCP-CMLV    IGGVDFGSSI TYSCNSGYHL IGESKSYCEL GSTGSMVWNP EAPICESVKC
     SPICE    IGGVDFGSSI TYSCNSGYYL IGEYKSYCKL GSTGSMVWNP KAPICESVKC
       IMP    IGGVEFGSSI TYSCNSGYQL IGESKSYCEL GYTGSMVWNP EAPICESVKC
  VCP-MPXV    IGGVDFGSSI TYSCNSGYHL IGESKSYCEL GSTGSMVWNP EAPICESVKC
 Consensus    IGGV#FGSSI TYSCNSGYhL IGEsKSYCeL GsTGSMVWNP eAPICESVKC 151                                                     200
    VCP-VV    QSPPSISNGR HNGYEDFYTD GSVVTYSCNS GYSLIGNSGV LCSGGEWSDP
  VCP-CMLV    QSPPSISNGR HNGYDNFYTD GSVVTYSCNS GYSLIGNSGV LCSGGEWSDP
     SPICE    QLPPSISNGR HNGYNDFYTD GSVVTYSCNS GYSLIGNSGV LCSGGEWSNP
       IMP    PSPPSVTNGR HNGYEDFYTD GSVVTYSCNS GYSLIGNSGI VCSGGEWSDP
  VCP-MPXV    QSPPSISNGR HNGYEDFYID GSIVTYSCNS GYSLIGNSGV MCSGGEWSNP
 Consensus    qsPPS!sNGR HNGY##FYtD GS!VTYSCNS GYSLIGNSG! .CSGGEWS#P 201                                                     250
    VCP-VV    PTCQIVKCPH PTISNGYLSS GFKRSYSYND NVDFKCKYGY KLSGSSSSTC
  VCP-CMLV    PTCQIVKCPH PTISNGYLSS GFKRSYSYND NVDFTCKYGY KLSGSSSSTC
     SPICE    PTCQIVKCPH PTILNGYLSS GFKRSYSYND NVDFTCKYGY KLSGSSSSTC
       IMP    PTCQIVKCPH PSITNGYLSS GFKRSYSHND NVDFKCRHGY KLSGSSSSTC
  VCP-MPXV    PTCQIVKCPH P.ISNGKLLA A......... ..........
 Consensus    PTCQIVKCPH P.IsNGyLss gfkrsys.nd nvdf.c...gy klsgssssstc 251        265
    VCP-VV    SPGNTWKPEL PKCVR   (SEQ ID NO: 584)
  VCP-CMLV    SPGNTWQPEL PKCVR   (SEQ ID NO: 585)
     SPICE    SPGNTWQPEL PKCVR   (SEQ ID NO: 586)
       IMP    SPGNTWQPEL PKCVR   (SEQ ID NO: 587)
  VCP-MPXV    .......... .....   (SEQ ID NO: 588)
 Consensus    SPGNTW.PEL PKCVR   (SEQ ID NO: 589)
```

Fig. 2
A
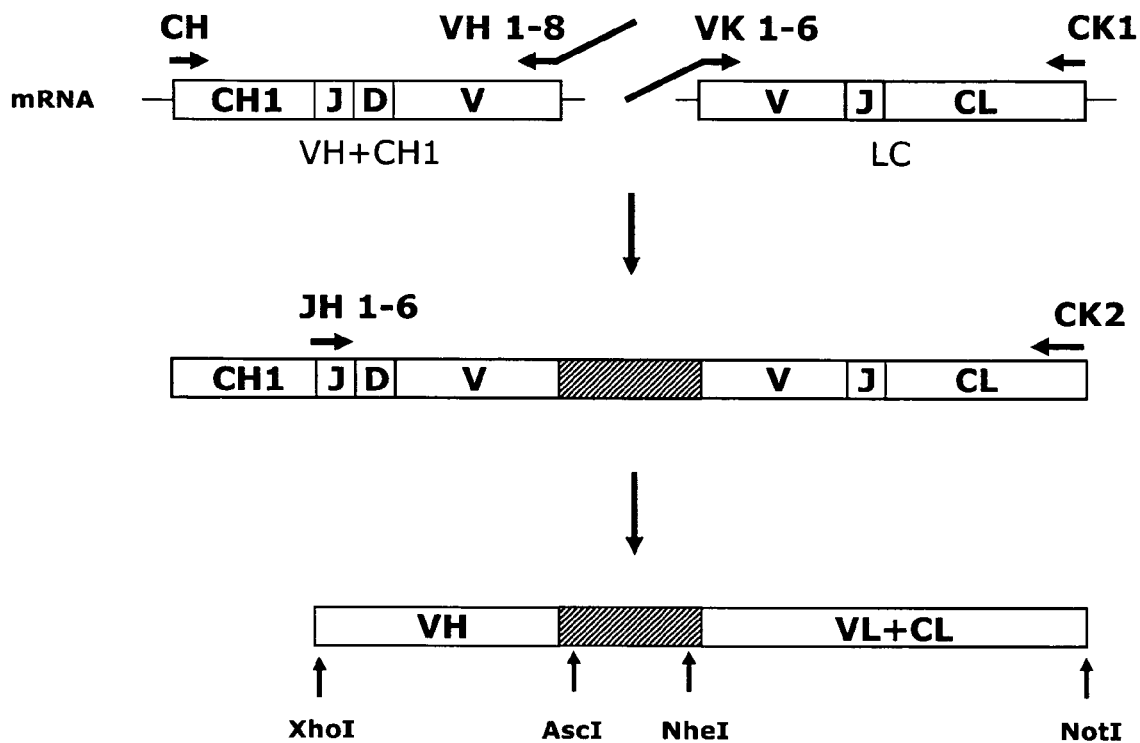
B
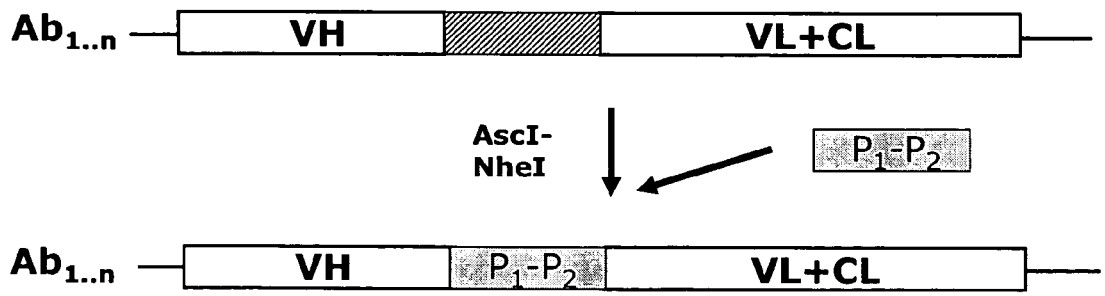

Fig. 3
A
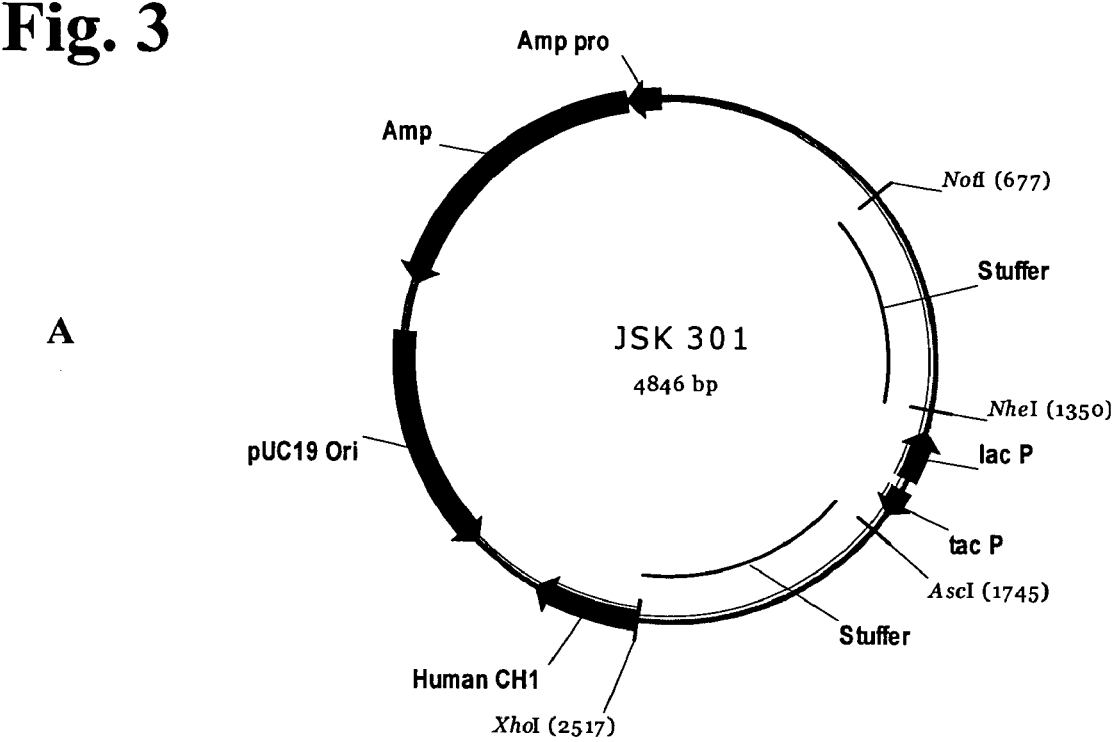
B
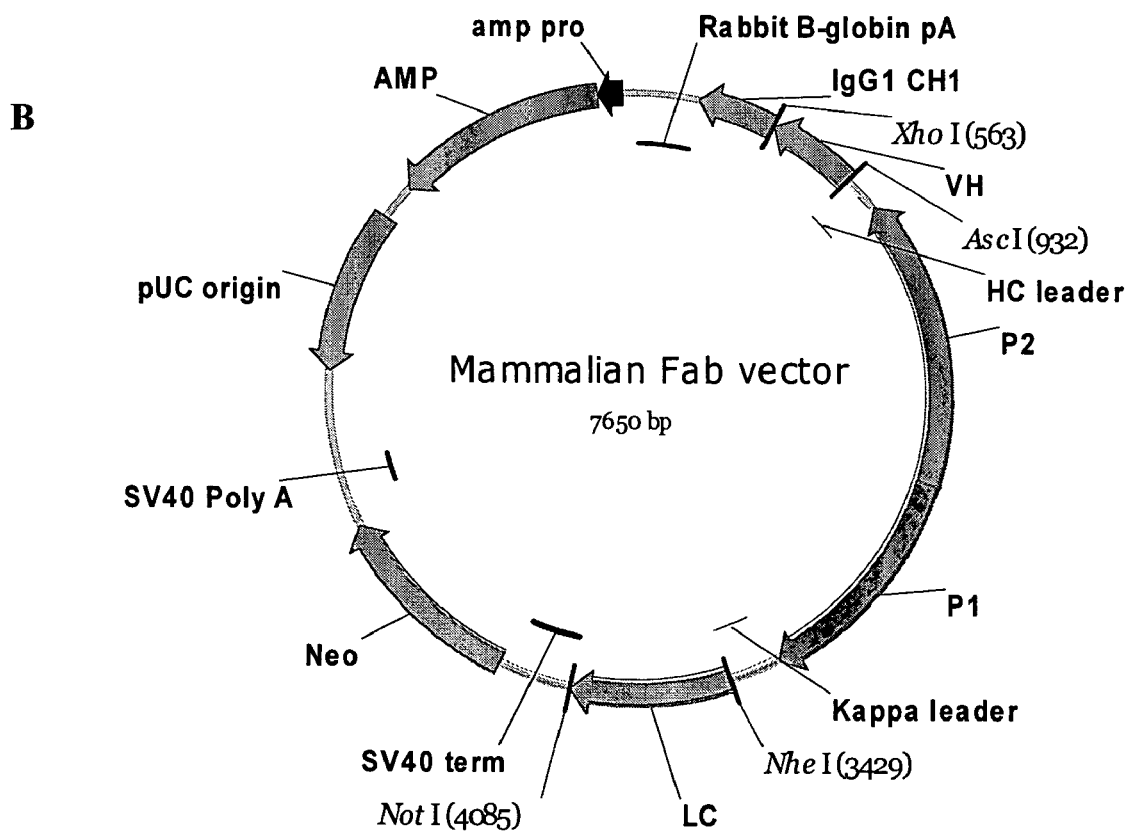

Fig. 11
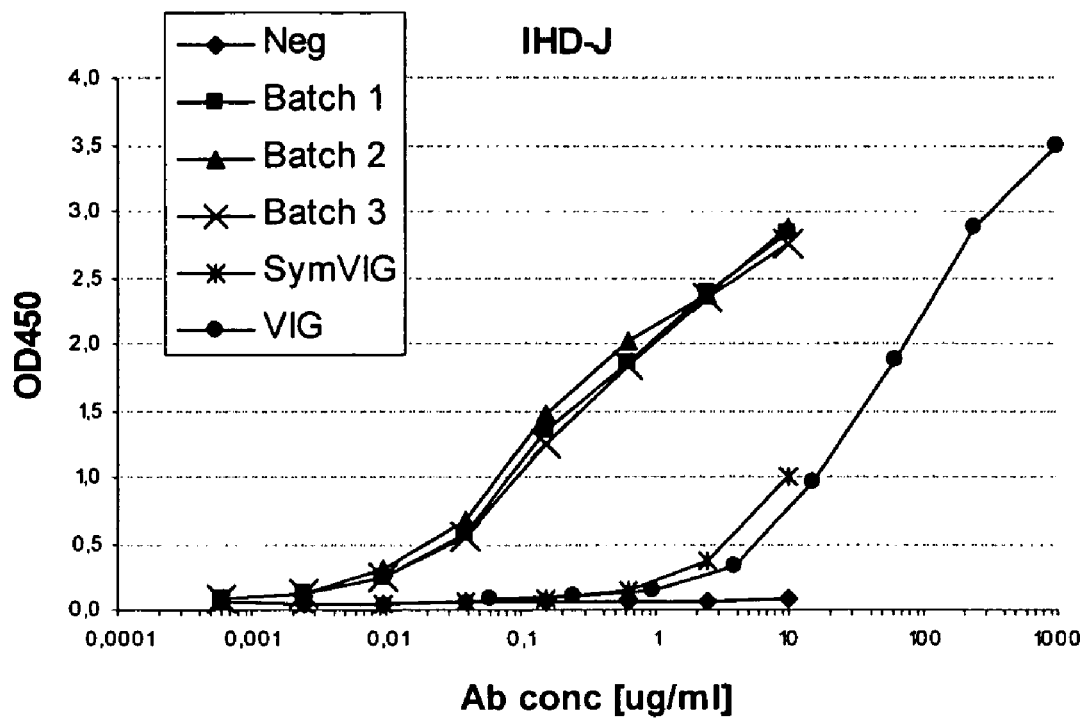
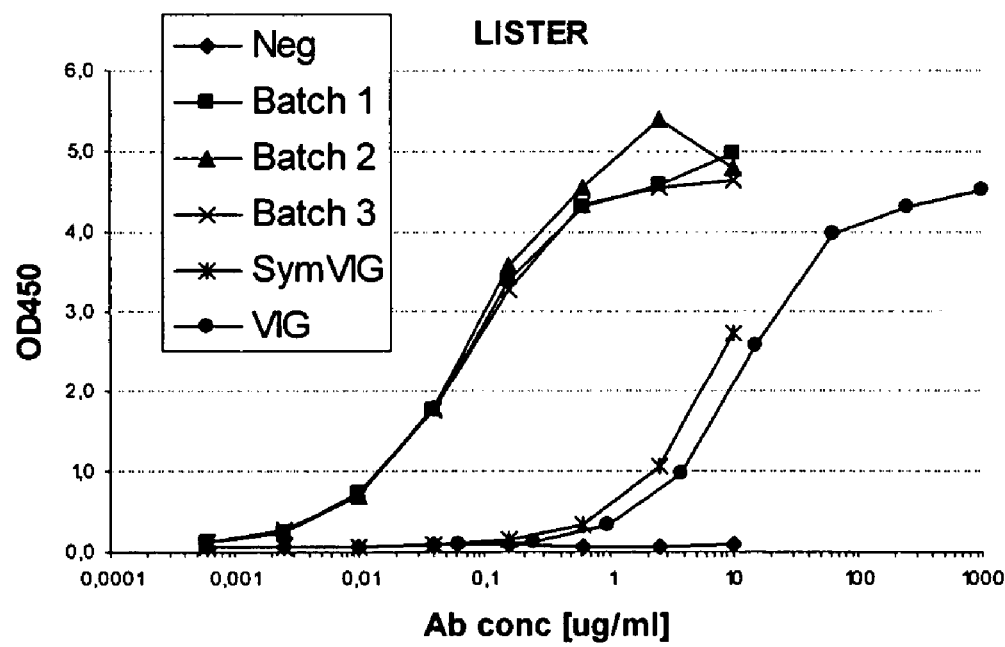

Fig. 11 Contd.
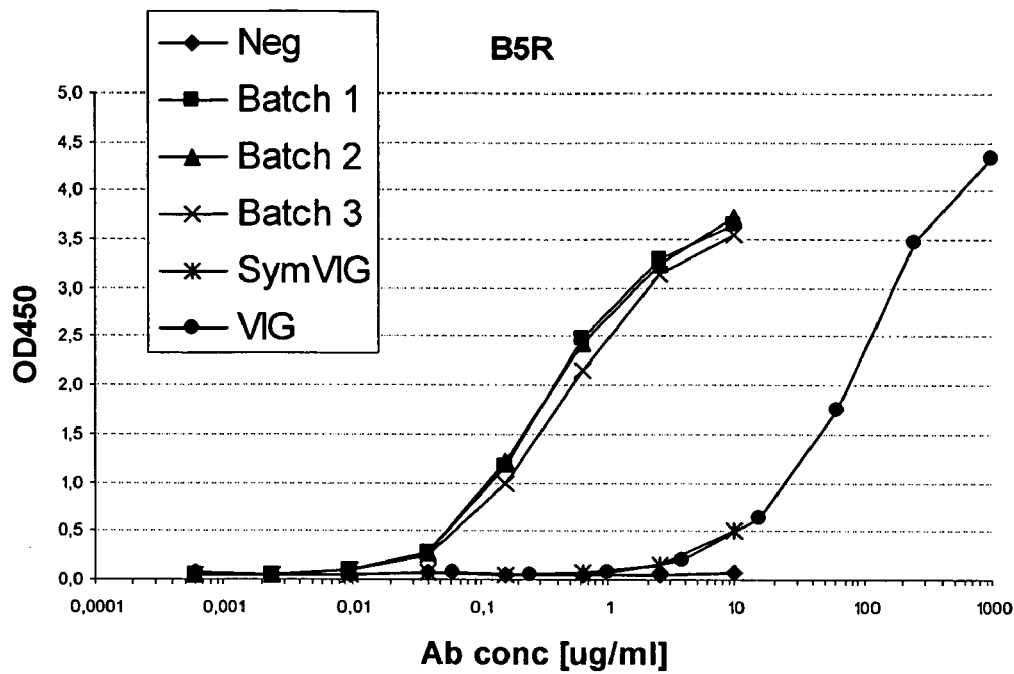
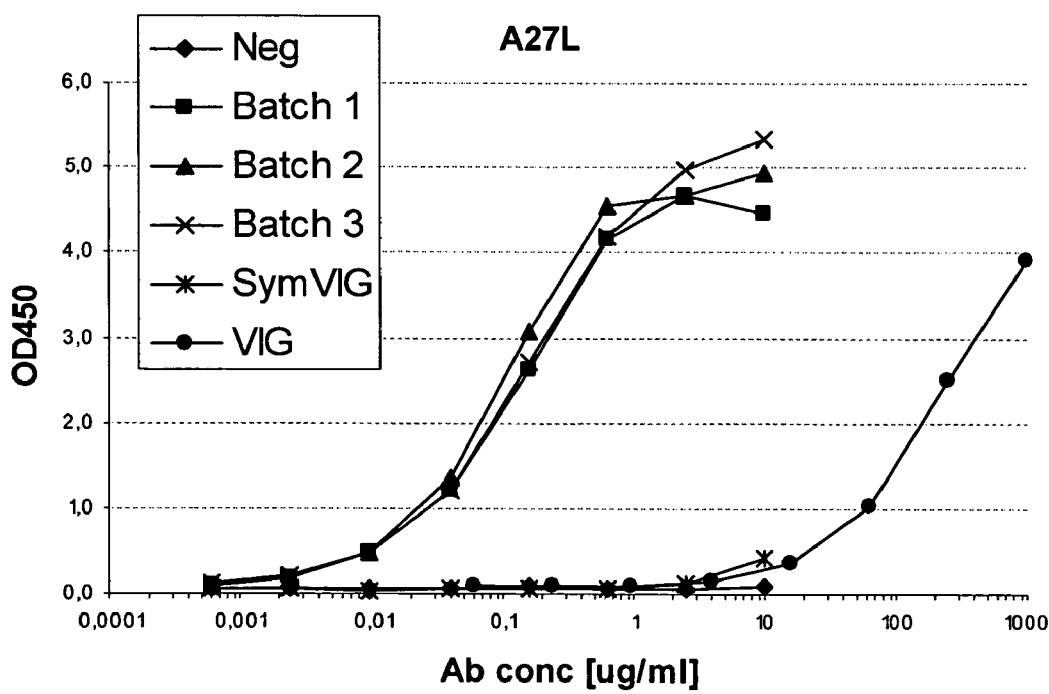

Fig. 11 Contd.
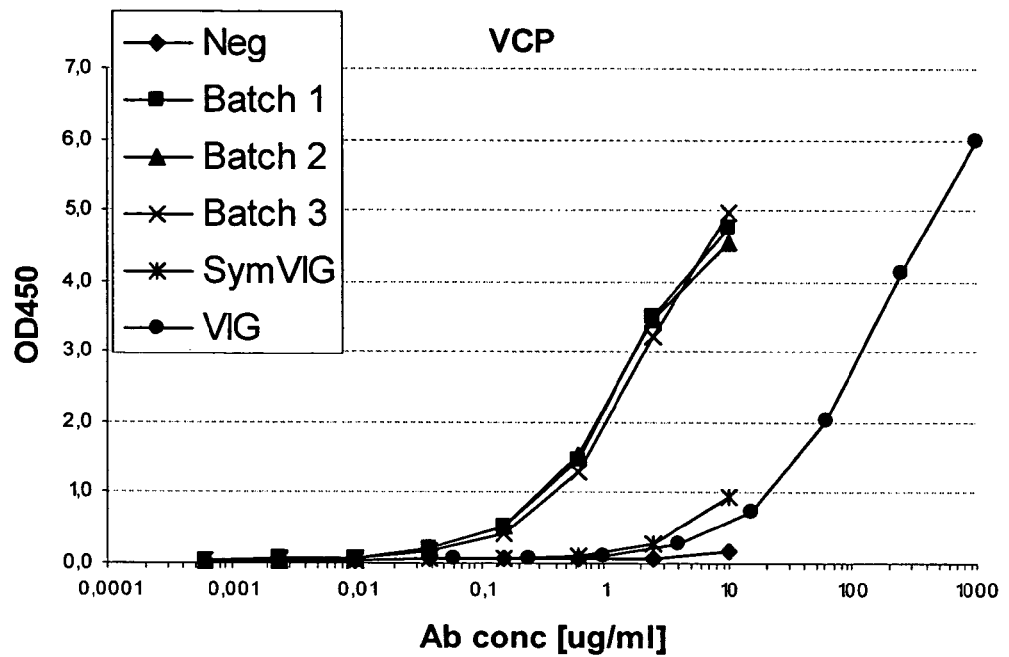
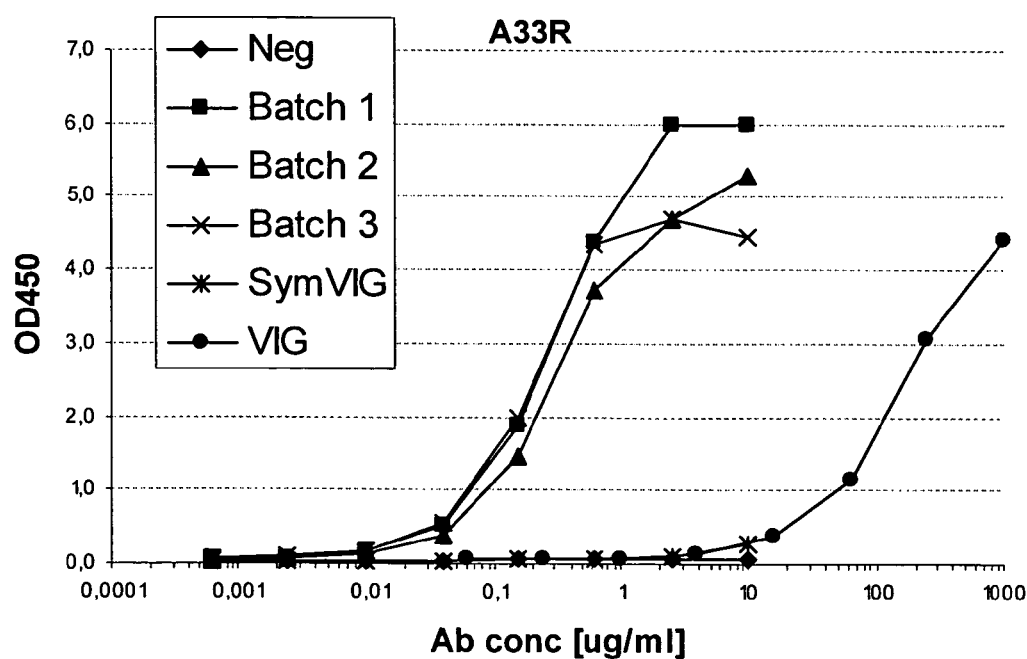

Fig. 11 Contd.
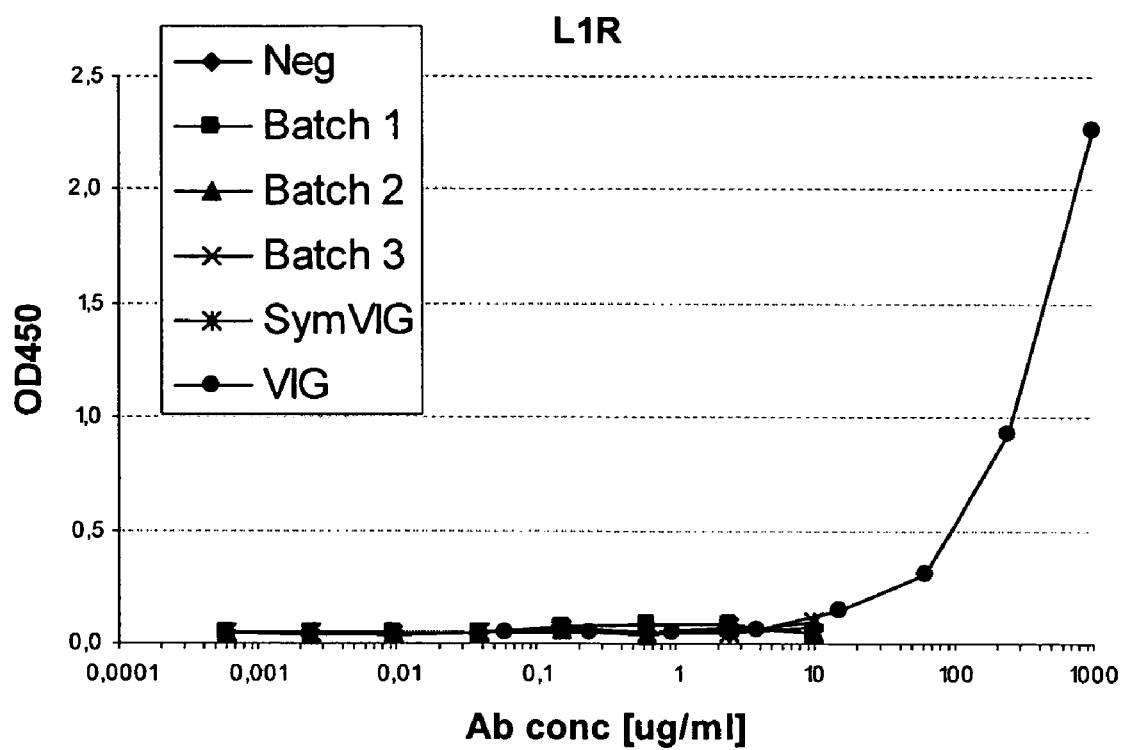

SEQUENCE LISTING

<160> NUMBER OF SEQ ID NOS: 589

<210> SEQ ID NO 1
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 1
gacsgatggg cccttggtgg                                            20

<210> SEQ ID NO 2
<211> LENGTH: 20
<212> TYPE: DNA
<213> ORGANISM: Artificial sequence
<220> FEATURE:
<223> OTHER INFORMATION: Synthetic PCR primer

<400> SEQUENCE: 2
gagtggctcc tgggggaaga                                              20

<210> SEQ ID NO 3
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 3
tattcccatg gcgcgcccag rtgcagctgg tgcart                            36

<210> SEQ ID NO 4
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 4
tattcccatg gcgcgccsag gtccagctgg trcagt                            36

<210> SEQ ID NO 5
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 5
tattcccatg gcgcgcccag rtcaccttga aggagt                            36

<210> SEQ ID NO 6
<211> LENGTH: 35
<212> TYPE: DNA
<213> ORGANISM: Artificial sequence
<220> FEATURE:
<223> OTHER INFORMATION: Synthetic PCR primer

<400> SEQUENCE: 6
tattcccatg gcgcgccsag gtgcagctgg tggag                             35

<210> SEQ ID NO 7
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 7
tattcccatg gcgcgcccag gtgcagctac agcagt                            36

<210> SEQ ID NO 8
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 8
tattcccatg gcgcgcccag stgcagctgc aggagt          36

<210> SEQ ID NO 9
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 9
tattcccatg gcgcgccgar gtgcagctgg tgcagt          36

<210> SEQ ID NO 10
<211> LENGTH: 37
<212> TYPE: DNA
<213> ORGANISM: Artificial sequence
<220> FEATURE:
<223> OTHER INFORMATION: Synthetic PCR primer

<400> SEQUENCE: 10
tattcccatg gcgcgcccag gtacagctgc agcagtc         37

<210> SEQ ID NO 11
<211> LENGTH: 38
<212> TYPE: DNA
<213> ORGANISM: Artificial sequence
<220> FEATURE:
<223> OTHER INFORMATION: Synthetic PCR primer

<400> SEQUENCE: 11
atatatatgc ggccgcttat taacactctc ccctgttg        38

<210> SEQ ID NO 12
<211> LENGTH: 45
<212> TYPE: DNA
<213> ORGANISM: Artificial sequence
<220> FEATURE:
<223> OTHER INFORMATION: Synthetic PCR primer

<400> SEQUENCE: 12
ggcgcgccat gggaatagct agccgacatc cagwtgaccc agtct    45

<210> SEQ ID NO 13
<211> LENGTH: 45
<212> TYPE: DNA
<213> ORGANISM: Artificial sequence
<220> FEATURE:
<223> OTHER INFORMATION: Synthetic PCR primer

<400> SEQUENCE: 13
ggcgcgccat gggaatagct agccgatgtt gtgatgactc agtct    45

<210> SEQ ID NO 14
<211> LENGTH: 45
<212> TYPE: DNA
<213> ORGANISM: Artificial sequence
<220> FEATURE:
<223> OTHER INFORMATION: Synthetic PCR primer

<400> SEQUENCE: 14
ggcgcgccat gggaatagct agccgaaatt gtgwtgacrc agtct    45

<210> SEQ ID NO 15

```
<211> LENGTH: 45
<212> TYPE: DNA
<213> ORGANISM: Artificial sequence
<220> FEATURE:
<223> OTHER INFORMATION: Synthetic PCR primer

<400> SEQUENCE: 15
ggcgcgccat gggaatagct agccgatatt gtgatgaccc acact            45

<210> SEQ ID NO 16
<211> LENGTH: 43
<212> TYPE: DNA
<213> ORGANISM: Artificial sequence
<220> FEATURE:
<223> OTHER INFORMATION: Synthetic PCR primer

<400> SEQUENCE: 16
ggcgcgccat gggaatagct agccgaaacg acactcacgc agt              43

<210> SEQ ID NO 17
<211> LENGTH: 45
<212> TYPE: DNA
<213> ORGANISM: Artificial sequence
<220> FEATURE:
<223> OTHER INFORMATION: Synthetic PCR primer

<400> SEQUENCE: 17
ggcgcgccat gggaatagct agccgaaatt gtgctgactc agtct            45

<210> SEQ ID NO 18
<211> LENGTH: 51
<212> TYPE: DNA
<213> ORGANISM: Artificial sequence
<220> FEATURE:
<223> OTHER INFORMATION: Synthetic PCR primer

<400> SEQUENCE: 18
accgcctcca ccggcggccg cttattaaca ctctcccctg ttgaagctct t      51

<210> SEQ ID NO 19
<211> LENGTH: 30
<212> TYPE: DNA
<213> ORGANISM: Artificial sequence
<220> FEATURE:
<223> OTHER INFORMATION: Synthetic PCR primer

<400> SEQUENCE: 19
ggaggcgctc gagacggtga ccagggtgcc                              30

<210> SEQ ID NO 20
<211> LENGTH: 30
<212> TYPE: DNA
<213> ORGANISM: Artificial sequence
<220> FEATURE:
<223> OTHER INFORMATION: Synthetic PCR primer

<400> SEQUENCE: 20
ggaggcgctc gagacggtga ccattgtccc                              30

<210> SEQ ID NO 21
<211> LENGTH: 30
<212> TYPE: DNA
<213> ORGANISM: Artificial sequence
<220> FEATURE:
<223> OTHER INFORMATION: Synthetic PCR primer

<400> SEQUENCE: 21
```
ggaggcgctc gagacggtga ccagggttcc          30

<210> SEQ ID NO 22
<211> LENGTH: 30
<212> TYPE: DNA
<213> ORGANISM: Artificial sequence
<220> FEATURE:
<223> OTHER INFORMATION: Synthetic PCR primer

<400> SEQUENCE: 22
ggaggcgctc gagacggtga ccgtggtccc          30

<210> SEQ ID NO 23
<211> LENGTH: 38
<212> TYPE: DNA
<213> ORGANISM: Artificial sequence
<220> FEATURE:
<223> OTHER INFORMATION: Synthetic PCR primer

<400> SEQUENCE: 23
gggaacagcc accatggcgg cggtgaaaac tcctgtta          38

<210> SEQ ID NO 24
<211> LENGTH: 43
<212> TYPE: DNA
<213> ORGANISM: Artificial sequence
<220> FEATURE:
<223> OTHER INFORMATION: Synthetic PCR primer

<400> SEQUENCE: 24
ggatcctcta gatcattaaa atgaaatcag tggagtagta aac          43

<210> SEQ ID NO 25
<211> LENGTH: 42
<212> TYPE: DNA
<213> ORGANISM: Artificial sequence
<220> FEATURE:
<223> OTHER INFORMATION: Synthetic PCR primer

<400> SEQUENCE: 25
gggaacagcc accatgacat gacaccttttt cctcagacat ct          42

<210> SEQ ID NO 26
<211> LENGTH: 39
<212> TYPE: DNA
<213> ORGANISM: Artificial sequence
<220> FEATURE:
<223> OTHER INFORMATION: Synthetic PCR primer

<400> SEQUENCE: 26
ggatcctcta gatcattaag aggttgtact actacctac          39

<210> SEQ ID NO 27
<211> LENGTH: 38
<212> TYPE: DNA
<213> ORGANISM: Artificial sequence
<220> FEATURE:
<223> OTHER INFORMATION: Synthetic PCR primer

<400> SEQUENCE: 27
gggaacagcc accatgacat gtactgtacc cactatga          38

<210> SEQ ID NO 28
<211> LENGTH: 36
<212> TYPE: DNA

<213> ORGANISM: Artificial sequence
<220> FEATURE:
<223> OTHER INFORMATION: Synthetic PCR primer

<400> SEQUENCE: 28
ggatcctcta gatcattata acgattctat ttcttg                               36

<210> SEQ ID NO 29
<211> LENGTH: 48
<212> TYPE: DNA
<213> ORGANISM: Artificial sequence
<220> FEATURE:
<223> OTHER INFORMATION: Synthetic PCR primer

<400> SEQUENCE: 29
tttttttttt tttttttttt tttttttttt ggatcctcta gatcatta                  48

<210> SEQ ID NO 30
<211> LENGTH: 39
<212> TYPE: DNA
<213> ORGANISM: Artificial sequence
<220> FEATURE:
<223> OTHER INFORMATION: Synthetic PCR primer

<400> SEQUENCE: 30
ggatcctaat acgactcact atagggaaca gccaccatg                            39

<210> SEQ ID NO 31
<211> LENGTH: 35
<212> TYPE: DNA
<213> ORGANISM: Artificial sequence
<220> FEATURE:
<223> OTHER INFORMATION: Synthetic PCR primer

<400> SEQUENCE: 31
gggaacagcc accatgatgc ctattaagtc aatag                                35

<210> SEQ ID NO 32
<211> LENGTH: 34
<212> TYPE: DNA
<213> ORGANISM: Artificial sequence
<220> FEATURE:
<223> OTHER INFORMATION: Synthetic PCR primer

<400> SEQUENCE: 32
ggatcctcta gatcattatt catcatcaaa agag                                 34

<210> SEQ ID NO 33
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 33
gggaacagcc accatggaag ccgtggtcaa tagcga                               36

<210> SEQ ID NO 34
<211> LENGTH: 40
<212> TYPE: DNA
<213> ORGANISM: Artificial sequence
<220> FEATURE:
<223> OTHER INFORMATION: Synthetic PCR primer

<400> SEQUENCE: 34
ggatcctcta gatcattaaa atagttctgt aatatgtcta                           40

<210> SEQ ID NO 35
<211> LENGTH: 36
<212> TYPE: DNA
<213> ORGANISM: Artificial sequence
<220> FEATURE:
<223> OTHER INFORMATION: Synthetic PCR primer

<400> SEQUENCE: 35
gggaacagcc accatgattg gtattctttt gttgat                                 36

<210> SEQ ID NO 36
<211> LENGTH: 38
<212> TYPE: DNA
<213> ORGANISM: Artificial sequence
<220> FEATURE:
<223> OTHER INFORMATION: Synthetic PCR primer

<400> SEQUENCE: 36
ggatcctcta gatcattata cagaagattt aactagat                               38

<210> SEQ ID NO 37
<211> LENGTH: 34
<212> TYPE: DNA
<213> ORGANISM: Artificial sequence
<220> FEATURE:
<223> OTHER INFORMATION: Synthetic PCR primer

<400> SEQUENCE: 37
gggaacagcc accatgccgc aacaactatc tcct                                   34

<210> SEQ ID NO 38
<211> LENGTH: 43
<212> TYPE: DNA
<213> ORGANISM: Artificial sequence
<220> FEATURE:
<223> OTHER INFORMATION: Synthetic PCR primer

<400> SEQUENCE: 38
ggatcctcta gatcattatt tattcccttc gatatatttt tga                         43

<210> SEQ ID NO 39
<211> LENGTH: 34
<212> TYPE: DNA
<213> ORGANISM: Artificial sequence
<220> FEATURE:
<223> OTHER INFORMATION: Synthetic PCR primer

<400> SEQUENCE: 39
gggaacagcc accatgacga ccgtaccagt gacg                                   34

<210> SEQ ID NO 40
<211> LENGTH: 38
<212> TYPE: DNA
<213> ORGANISM: Artificial sequence
<220> FEATURE:
<223> OTHER INFORMATION: Synthetic PCR primer

<400> SEQUENCE: 40
ggatcctcta gatcattaaa taattttaat tcgtttaa                               38

<210> SEQ ID NO 41
<211> LENGTH: 37
<212> TYPE: DNA
<213> ORGANISM: Artificial sequence
<220> FEATURE:

<223> OTHER INFORMATION: Synthetic PCR primer

<400> SEQUENCE: 41
gggaacagcc accatgagtt atttaagata ttacaat                       37

<210> SEQ ID NO 42
<211> LENGTH: 39
<212> TYPE: DNA
<213> ORGANISM: Artificial sequence
<220> FEATURE:
<223> OTHER INFORMATION: Synthetic PCR primer

<400> SEQUENCE: 42
ggatcctcta gatcattaat aatcgtcagt atttaaact                     39

<210> SEQ ID NO 43
<211> LENGTH: 34
<212> TYPE: DNA
<213> ORGANISM: Artificial sequence
<220> FEATURE:
<223> OTHER INFORMATION: Synthetic PCR primer

<400> SEQUENCE: 43
gggaacagcc accatggaga atgttcctaa tgta                          34

<210> SEQ ID NO 44
<211> LENGTH: 37
<212> TYPE: DNA
<213> ORGANISM: Artificial sequence
<220> FEATURE:
<223> OTHER INFORMATION: Synthetic PCR primer

<400> SEQUENCE: 44
ggatcctcta gattatcatc tgcgaagaac atcgtta                       37

<210> SEQ ID NO 45
<211> LENGTH: 34
<212> TYPE: DNA
<213> ORGANISM: Artificial sequence
<220> FEATURE:
<223> OTHER INFORMATION: Synthetic PCR primer

<400> SEQUENCE: 45
gggaacagcc accatgtggc catttgcatc ggta                          34

<210> SEQ ID NO 46
<211> LENGTH: 38
<212> TYPE: DNA
<213> ORGANISM: Artificial sequence
<220> FEATURE:
<223> OTHER INFORMATION: Synthetic PCR primer

<400> SEQUENCE: 46
ggatcctcta gatcattaaa tttttaacga tttactgt                      38

<210> SEQ ID NO 47
<211> LENGTH: 37
<212> TYPE: DNA
<213> ORGANISM: Artificial sequence
<220> FEATURE:
<223> OTHER INFORMATION: Synthetic PCR primer

<400> SEQUENCE: 47
gggaacagcc accatgatgg gggcagctgt tactctt                       37

```
<210> SEQ ID NO 48
<211> LENGTH: 41
<212> TYPE: DNA
<213> ORGANISM: Artificial sequence
<220> FEATURE:
<223> OTHER INFORMATION: Synthetic PCR primer

<400> SEQUENCE: 48
ggatcctcta gatcattaag gcagttttat tttatctttt a                              41

<210> SEQ ID NO 49
<211> LENGTH: 132
<212> TYPE: PRT
<213> ORGANISM: Homo sapiens

<400> SEQUENCE: 49

Gln Val Gln Leu Val Gln Ser Gly Ala Glu Val Lys Lys Pro Gly Tyr
 1               5                  10                  15

Ser Val Lys Val Ser Cys Gln Ala Ser Gly Leu Thr Phe Ser Asn Tyr
             20                  25                  30

Arg Val Ser Trp Val Arg Gln Ala Pro Gly Gln Gly Leu Glu Trp Met
         35                  40                  45

Gly Gly Ile Ile Pro Ile Phe Gly Thr Thr Asn Tyr Ala Gln Lys Phe
     50                  55                  60

Gln Gly Arg Val Thr Ile Ser Ala Asp Arg Ser Pro Ser Arg Val Thr
 65                  70                  75                  80

Ser Leu Ala Asp Lys Ser Thr Ile Thr Val Tyr Met Glu Leu Ser Ser
                 85                  90                  95

Leu Arg Ser Glu Asp Thr Ala Val Tyr Tyr Cys Ala Arg Ser Arg Gly
            100                 105                 110

Ser Gln Asp Tyr Tyr Gly Met Asp Val Trp Gly Gln Gly Thr Thr Val
        115                 120                 125

Thr Val Ser Ser
    130

<210> SEQ ID NO 50
<211> LENGTH: 5
<212> TYPE: PRT
<213> ORGANISM: Homo sapiens

<400> SEQUENCE: 50

Glu Leu Ala Met His
 1               5

<210> SEQ ID NO 51
<211> LENGTH: 5
<212> TYPE: PRT
<213> ORGANISM: Homo sapiens

<400> SEQUENCE: 51

Gly Phe His Trp Ser
 1               5

<210> SEQ ID NO 52
<211> LENGTH: 7
<212> TYPE: PRT
<213> ORGANISM: Homo sapiens

<400> SEQUENCE: 52

Asn Asn Ile Ala Ser Trp Asn
 1               5
```

```
<210> SEQ ID NO 53
<211> LENGTH: 5
<212> TYPE: PRT
<213> ORGANISM: Homo sapiens

<400> SEQUENCE: 53

Arg Tyr Gly Met His
1               5

<210> SEQ ID NO 54
<211> LENGTH: 5
<212> TYPE: PRT
<213> ORGANISM: Homo sapiens

<400> SEQUENCE: 54

Thr Tyr Trp Ile Gly
1               5

<210> SEQ ID NO 55
<211> LENGTH: 5
<212> TYPE: PRT
<213> ORGANISM: Homo sapiens

<400> SEQUENCE: 55

Gly His Tyr Met His
1               5

<210> SEQ ID NO 56
<211> LENGTH: 7
<212> TYPE: PRT
<213> ORGANISM: Homo sapiens

<400> SEQUENCE: 56

Thr Ser Gly Val Gly Val Asp
1               5

<210> SEQ ID NO 57
<211> LENGTH: 7
<212> TYPE: PRT
<213> ORGANISM: Homo sapiens

<400> SEQUENCE: 57

Thr Ser Gly Met Cys Val Ser
1               5

<210> SEQ ID NO 58
<211> LENGTH: 5
<212> TYPE: PRT
<213> ORGANISM: Homo sapiens

<400> SEQUENCE: 58

Lys Tyr Trp Met Ser
1               5

<210> SEQ ID NO 59
<211> LENGTH: 5
<212> TYPE: PRT
<213> ORGANISM: Homo sapiens

<400> SEQUENCE: 59

Ser Tyr Gly Met His
1               5

<210> SEQ ID NO 60
```

```
<211> LENGTH: 5
<212> TYPE: PRT
<213> ORGANISM: Homo sapiens

<400> SEQUENCE: 60

Asn Tyr Tyr Ile His
1               5

<210> SEQ ID NO 61
<211> LENGTH: 5
<212> TYPE: PRT
<213> ORGANISM: Homo sapiens

<400> SEQUENCE: 61

Asp Tyr Ala Met His
1               5

<210> SEQ ID NO 62
<211> LENGTH: 5
<212> TYPE: PRT
<213> ORGANISM: Homo sapiens

<400> SEQUENCE: 62

Gly Tyr Tyr Trp Thr
1               5

<210> SEQ ID NO 63
<211> LENGTH: 5
<212> TYPE: PRT
<213> ORGANISM: Homo sapiens

<400> SEQUENCE: 63

Thr Tyr Trp Ile Gly
1               5

<210> SEQ ID NO 64
<211> LENGTH: 5
<212> TYPE: PRT
<213> ORGANISM: Homo sapiens

<400> SEQUENCE: 64

Ser Tyr Thr Met Asn
1               5

<210> SEQ ID NO 65
<211> LENGTH: 5
<212> TYPE: PRT
<213> ORGANISM: Homo sapiens

<400> SEQUENCE: 65

Lys Tyr Trp Ile Gly
1               5

<210> SEQ ID NO 66
<211> LENGTH: 5
<212> TYPE: PRT
<213> ORGANISM: Homo sapiens

<400> SEQUENCE: 66

Asn Tyr Ala Val His
1               5

<210> SEQ ID NO 67
<211> LENGTH: 7
<212> TYPE: PRT
```

<213> ORGANISM: Homo sapiens

<400> SEQUENCE: 67

Ser Gly Asp Tyr Tyr Trp Asn
1               5

<210> SEQ ID NO 68
<211> LENGTH: 5
<212> TYPE: PRT
<213> ORGANISM: Homo sapiens

<400> SEQUENCE: 68

Lys Tyr Tyr Met His
1               5

<210> SEQ ID NO 69
<211> LENGTH: 5
<212> TYPE: PRT
<213> ORGANISM: Homo sapiens

<400> SEQUENCE: 69

Thr Tyr Gly Ile Ser
1               5

<210> SEQ ID NO 70
<211> LENGTH: 6
<212> TYPE: PRT
<213> ORGANISM: Homo sapiens

<400> SEQUENCE: 70

Ser Asn Asn Trp Trp Ser
1               5

<210> SEQ ID NO 71
<211> LENGTH: 5
<212> TYPE: PRT
<213> ORGANISM: Homo sapiens

<400> SEQUENCE: 71

Lys Tyr Tyr Ile His
1               5

<210> SEQ ID NO 72
<211> LENGTH: 7
<212> TYPE: PRT
<213> ORGANISM: Homo sapiens

<400> SEQUENCE: 72

Arg Gly Asp Phe Tyr Trp Ser
1               5

<210> SEQ ID NO 73
<211> LENGTH: 5
<212> TYPE: PRT
<213> ORGANISM: Homo sapiens

<400> SEQUENCE: 73

Asp Tyr Thr Thr His
1               5

<210> SEQ ID NO 74
<211> LENGTH: 5
<212> TYPE: PRT
<213> ORGANISM: Homo sapiens

```
<400> SEQUENCE: 74

Asp Tyr Ala Met His
1               5

<210> SEQ ID NO 75
<211> LENGTH: 5
<212> TYPE: PRT
<213> ORGANISM: Homo sapiens

<400> SEQUENCE: 75

Asp Tyr Ala Met His
1               5

<210> SEQ ID NO 76
<211> LENGTH: 5
<212> TYPE: PRT
<213> ORGANISM: Homo sapiens

<400> SEQUENCE: 76

Asp Tyr Tyr Ile His
1               5

<210> SEQ ID NO 77
<211> LENGTH: 5
<212> TYPE: PRT
<213> ORGANISM: Homo sapiens

<400> SEQUENCE: 77

Ser Tyr Ala Ile Ala
1               5

<210> SEQ ID NO 78
<211> LENGTH: 5
<212> TYPE: PRT
<213> ORGANISM: Homo sapiens

<400> SEQUENCE: 78

Gly Tyr Tyr Trp Gly
1               5

<210> SEQ ID NO 79
<211> LENGTH: 5
<212> TYPE: PRT
<213> ORGANISM: Homo sapiens

<400> SEQUENCE: 79

Asp Tyr Ala Val Ser
1               5

<210> SEQ ID NO 80
<211> LENGTH: 7
<212> TYPE: PRT
<213> ORGANISM: Homo sapiens

<400> SEQUENCE: 80

Ser Arg Asn Tyr Tyr Trp Gly
1               5

<210> SEQ ID NO 81
<211> LENGTH: 8
<212> TYPE: PRT
<213> ORGANISM: Homo sapiens

<400> SEQUENCE: 81
```

```
Ser Ser Thr Asn Tyr Tyr Trp Gly
1               5

<210> SEQ ID NO 82
<211> LENGTH: 7
<212> TYPE: PRT
<213> ORGANISM: Homo sapiens

<400> SEQUENCE: 82

Thr Ser Thr Ala Ala Trp Asn
1               5

<210> SEQ ID NO 83
<211> LENGTH: 5
<212> TYPE: PRT
<213> ORGANISM: Homo sapiens

<400> SEQUENCE: 83

Asp Tyr Ala Met His
1               5

<210> SEQ ID NO 84
<211> LENGTH: 5
<212> TYPE: PRT
<213> ORGANISM: Homo sapiens

<400> SEQUENCE: 84

Glu Tyr Tyr Ile His
1               5

<210> SEQ ID NO 85
<211> LENGTH: 5
<212> TYPE: PRT
<213> ORGANISM: Homo sapiens

<400> SEQUENCE: 85

Ser Tyr Trp Ile Ser
1               5

<210> SEQ ID NO 86
<211> LENGTH: 5
<212> TYPE: PRT
<213> ORGANISM: Homo sapiens

<400> SEQUENCE: 86

Ser Tyr Trp Ile Ala
1               5

<210> SEQ ID NO 87
<211> LENGTH: 5
<212> TYPE: PRT
<213> ORGANISM: Homo sapiens

<400> SEQUENCE: 87

Asp Phe Ala Met His
1               5

<210> SEQ ID NO 88
<211> LENGTH: 5
<212> TYPE: PRT
<213> ORGANISM: Homo sapiens

<400> SEQUENCE: 88

Asp Tyr Ala Ile Ser
1               5
```

```
<210> SEQ ID NO 89
<211> LENGTH: 7
<212> TYPE: PRT
<213> ORGANISM: Homo sapiens

<400> SEQUENCE: 89

Ser Thr Gly Val Gly Val Gly
1               5

<210> SEQ ID NO 90
<211> LENGTH: 5
<212> TYPE: PRT
<213> ORGANISM: Homo sapiens

<400> SEQUENCE: 90

Ser Tyr Ala Ile Asn
1               5

<210> SEQ ID NO 91
<211> LENGTH: 5
<212> TYPE: PRT
<213> ORGANISM: Homo sapiens

<400> SEQUENCE: 91

Gly Tyr Tyr Trp Ser
1               5

<210> SEQ ID NO 92
<211> LENGTH: 5
<212> TYPE: PRT
<213> ORGANISM: Homo sapiens

<400> SEQUENCE: 92

Gly Tyr Gly Ile Ser
1               5

<210> SEQ ID NO 93
<211> LENGTH: 5
<212> TYPE: PRT
<213> ORGANISM: Homo sapiens

<400> SEQUENCE: 93

Asn Ser Ala Ile Asn
1               5

<210> SEQ ID NO 94
<211> LENGTH: 5
<212> TYPE: PRT
<213> ORGANISM: Homo sapiens

<400> SEQUENCE: 94

Asn Tyr Arg Val Ser
1               5

<210> SEQ ID NO 95
<211> LENGTH: 5
<212> TYPE: PRT
<213> ORGANISM: Homo sapiens

<400> SEQUENCE: 95

Asn Tyr Ala Met Ser
1               5
```

```
<210> SEQ ID NO 96
<211> LENGTH: 5
<212> TYPE: PRT
<213> ORGANISM: Homo sapiens

<400> SEQUENCE: 96

Asp Asn Tyr Met Asn
1               5

<210> SEQ ID NO 97
<211> LENGTH: 5
<212> TYPE: PRT
<213> ORGANISM: Homo sapiens

<400> SEQUENCE: 97

Asp Tyr Ala Met His
1               5

<210> SEQ ID NO 98
<211> LENGTH: 7
<212> TYPE: PRT
<213> ORGANISM: Homo sapiens

<400> SEQUENCE: 98

Thr Ser Gly Val Gly Val Gly
1               5

<210> SEQ ID NO 99
<211> LENGTH: 5
<212> TYPE: PRT
<213> ORGANISM: Homo sapiens

<400> SEQUENCE: 99

Thr Tyr Gly Met His
1               5

<210> SEQ ID NO 100
<211> LENGTH: 5
<212> TYPE: PRT
<213> ORGANISM: Homo sapiens

<400> SEQUENCE: 100

Asn Tyr Gly Ile His
1               5

<210> SEQ ID NO 101
<211> LENGTH: 5
<212> TYPE: PRT
<213> ORGANISM: Homo sapiens

<400> SEQUENCE: 101

Ser Asp Asn Trp Ser
1               5

<210> SEQ ID NO 102
<211> LENGTH: 5
<212> TYPE: PRT
<213> ORGANISM: Homo sapiens

<400> SEQUENCE: 102

Ser Phe Trp Ile Gly
1               5

<210> SEQ ID NO 103
<211> LENGTH: 5
```

```
<212> TYPE: PRT
<213> ORGANISM: Homo sapiens

<400> SEQUENCE: 103

Asn Tyr Ala Met Tyr
1               5

<210> SEQ ID NO 104
<211> LENGTH: 5
<212> TYPE: PRT
<213> ORGANISM: Homo sapiens

<400> SEQUENCE: 104

Ser Tyr Tyr Met His
1               5

<210> SEQ ID NO 105
<211> LENGTH: 7
<212> TYPE: PRT
<213> ORGANISM: Homo sapiens

<400> SEQUENCE: 105

Ser Pro Gly Tyr Tyr Trp Asn
1               5

<210> SEQ ID NO 106
<211> LENGTH: 5
<212> TYPE: PRT
<213> ORGANISM: Homo sapiens

<400> SEQUENCE: 106

Ser Phe Ala Ile Ser
1               5

<210> SEQ ID NO 107
<211> LENGTH: 5
<212> TYPE: PRT
<213> ORGANISM: Homo sapiens

<400> SEQUENCE: 107

Thr Tyr Gly Ile Ser
1               5

<210> SEQ ID NO 108
<211> LENGTH: 7
<212> TYPE: PRT
<213> ORGANISM: Homo sapiens

<400> SEQUENCE: 108

Ser Ala Gly Tyr Tyr Trp Ser
1               5

<210> SEQ ID NO 109
<211> LENGTH: 5
<212> TYPE: PRT
<213> ORGANISM: Homo sapiens

<400> SEQUENCE: 109

Ser Tyr Trp Ile Gly
1               5

<210> SEQ ID NO 110
<211> LENGTH: 7
<212> TYPE: PRT
<213> ORGANISM: Homo sapiens
```

```
<400> SEQUENCE: 110

Ser Gly Gly Tyr Tyr Trp Ser
1               5

<210> SEQ ID NO 111
<211> LENGTH: 5
<212> TYPE: PRT
<213> ORGANISM: Homo sapiens

<400> SEQUENCE: 111

Asp Tyr Tyr Met Ser
1               5

<210> SEQ ID NO 112
<211> LENGTH: 6
<212> TYPE: PRT
<213> ORGANISM: Homo sapiens

<400> SEQUENCE: 112

Gly Ala Tyr His Trp Ser
1               5

<210> SEQ ID NO 113
<211> LENGTH: 5
<212> TYPE: PRT
<213> ORGANISM: Homo sapiens

<400> SEQUENCE: 113

Ala Tyr Tyr Trp Ser
1               5

<210> SEQ ID NO 114
<211> LENGTH: 5
<212> TYPE: PRT
<213> ORGANISM: Homo sapiens

<400> SEQUENCE: 114

Asp Tyr Thr Met Ser
1               5

<210> SEQ ID NO 115
<211> LENGTH: 5
<212> TYPE: PRT
<213> ORGANISM: Homo sapiens

<400> SEQUENCE: 115

Asp His Ser Ile Gly
1               5

<210> SEQ ID NO 116
<211> LENGTH: 6
<212> TYPE: PRT
<213> ORGANISM: Homo sapiens

<400> SEQUENCE: 116

Ser Ser His Trp Trp Asn
1               5

<210> SEQ ID NO 117
<211> LENGTH: 5
<212> TYPE: PRT
<213> ORGANISM: Homo sapiens

<400> SEQUENCE: 117
```

```
Tyr Tyr Ala Ile Asn
1               5

<210> SEQ ID NO 118
<211> LENGTH: 5
<212> TYPE: PRT
<213> ORGANISM: Homo sapiens

<400> SEQUENCE: 118

Asn Tyr Tyr Met His
1               5

<210> SEQ ID NO 119
<211> LENGTH: 5
<212> TYPE: PRT
<213> ORGANISM: Homo sapiens

<400> SEQUENCE: 119

Ser Phe Gly Ile Ser
1               5

<210> SEQ ID NO 120
<211> LENGTH: 7
<212> TYPE: PRT
<213> ORGANISM: Homo sapiens

<400> SEQUENCE: 120

Asn Asp Arg Met Gly Val Ser
1               5

<210> SEQ ID NO 121
<211> LENGTH: 5
<212> TYPE: PRT
<213> ORGANISM: Homo sapiens

<400> SEQUENCE: 121

Ser Tyr Tyr Trp Ser
1               5

<210> SEQ ID NO 122
<211> LENGTH: 5
<212> TYPE: PRT
<213> ORGANISM: Homo sapiens

<400> SEQUENCE: 122

Gly Tyr Tyr Trp Thr
1               5

<210> SEQ ID NO 123
<211> LENGTH: 5
<212> TYPE: PRT
<213> ORGANISM: Homo sapiens

<400> SEQUENCE: 123

Ser Tyr Gly Met His
1               5

<210> SEQ ID NO 124
<211> LENGTH: 5
<212> TYPE: PRT
<213> ORGANISM: Homo sapiens

<400> SEQUENCE: 124

Asn Tyr Trp Ile Gly
```

```
1               5

<210> SEQ ID NO 125
<211> LENGTH: 5
<212> TYPE: PRT
<213> ORGANISM: Homo sapiens

<400> SEQUENCE: 125

Thr Tyr Thr Met His
1               5

<210> SEQ ID NO 126
<211> LENGTH: 5
<212> TYPE: PRT
<213> ORGANISM: Homo sapiens

<400> SEQUENCE: 126

Asn Tyr Ala Ile Ile
1               5

<210> SEQ ID NO 127
<211> LENGTH: 5
<212> TYPE: PRT
<213> ORGANISM: Homo sapiens

<400> SEQUENCE: 127

Asn Tyr Tyr Val His
1               5

<210> SEQ ID NO 128
<211> LENGTH: 5
<212> TYPE: PRT
<213> ORGANISM: Homo sapiens

<400> SEQUENCE: 128

Ser His Gly Val Asn
1               5

<210> SEQ ID NO 129
<211> LENGTH: 7
<212> TYPE: PRT
<213> ORGANISM: Homo sapiens

<400> SEQUENCE: 129

Thr Gly Asp Tyr Tyr Trp Ser
1               5

<210> SEQ ID NO 130
<211> LENGTH: 7
<212> TYPE: PRT
<213> ORGANISM: Homo sapiens

<400> SEQUENCE: 130

Ser Gly Tyr Tyr Tyr Trp Asn
1               5

<210> SEQ ID NO 131
<211> LENGTH: 5
<212> TYPE: PRT
<213> ORGANISM: Homo sapiens

<400> SEQUENCE: 131

Gly Tyr Tyr Ile His
1               5
```

```
<210> SEQ ID NO 132
<211> LENGTH: 5
<212> TYPE: PRT
<213> ORGANISM: Homo sapiens

<400> SEQUENCE: 132

Ala Tyr Tyr Ile His
1               5

<210> SEQ ID NO 133
<211> LENGTH: 5
<212> TYPE: PRT
<213> ORGANISM: Homo sapiens

<400> SEQUENCE: 133

Thr Tyr Glu Met Ser
1               5

<210> SEQ ID NO 134
<211> LENGTH: 5
<212> TYPE: PRT
<213> ORGANISM: Homo sapiens

<400> SEQUENCE: 134

Thr Tyr Trp Ile Ala
1               5

<210> SEQ ID NO 135
<211> LENGTH: 5
<212> TYPE: PRT
<213> ORGANISM: Homo sapiens

<400> SEQUENCE: 135

Ser Tyr Ala Met Asn
1               5

<210> SEQ ID NO 136
<211> LENGTH: 7
<212> TYPE: PRT
<213> ORGANISM: Homo sapiens

<400> SEQUENCE: 136

Ser Gly Pro Tyr Tyr Trp Ser
1               5

<210> SEQ ID NO 137
<211> LENGTH: 5
<212> TYPE: PRT
<213> ORGANISM: Homo sapiens

<400> SEQUENCE: 137

Ser Asn Pro Val Ser
1               5

<210> SEQ ID NO 138
<211> LENGTH: 5
<212> TYPE: PRT
<213> ORGANISM: Homo sapiens

<400> SEQUENCE: 138

Asp Tyr Tyr Leu His
1               5

<210> SEQ ID NO 139
```

```
<211> LENGTH: 17
<212> TYPE: PRT
<213> ORGANISM: Homo sapiens

<400> SEQUENCE: 139

Gly Phe Asp Pro Glu Asp Gly Glu Ala Val Tyr Ala Gln Gly Phe Gln
1               5                   10                  15

Gly

<210> SEQ ID NO 140
<211> LENGTH: 16
<212> TYPE: PRT
<213> ORGANISM: Homo sapiens

<400> SEQUENCE: 140

Glu Ile Asn His Ser Gly Ser Thr Asn Tyr Asn Pro Ser Val Lys Ser
1               5                   10                  15

<210> SEQ ID NO 141
<211> LENGTH: 18
<212> TYPE: PRT
<213> ORGANISM: Homo sapiens

<400> SEQUENCE: 141

Arg Thr Tyr Tyr Arg Ser Lys Trp Tyr Asp Asp Phe Ala Leu Ser Val
1               5                   10                  15

Lys Gly

<210> SEQ ID NO 142
<211> LENGTH: 17
<212> TYPE: PRT
<213> ORGANISM: Homo sapiens

<400> SEQUENCE: 142

Phe Leu Ser Phe Asp Glu Arg Asn Lys Phe Tyr Pro Asp Ser Leu Lys
1               5                   10                  15

Gly

<210> SEQ ID NO 143
<211> LENGTH: 17
<212> TYPE: PRT
<213> ORGANISM: Homo sapiens

<400> SEQUENCE: 143

Ile Ile Tyr Pro Gly Asp Ser Asp Thr Lys Tyr Ser Pro Ser Phe Gln
1               5                   10                  15

Gly

<210> SEQ ID NO 144
<211> LENGTH: 17
<212> TYPE: PRT
<213> ORGANISM: Homo sapiens

<400> SEQUENCE: 144

Trp Ile Asn Pro Ser Ser Gly Gly Thr Asn Tyr Ala Gln Lys Phe Gln
1               5                   10                  15

Gly

<210> SEQ ID NO 145
<211> LENGTH: 16
<212> TYPE: PRT
<213> ORGANISM: Homo sapiens
```

-continued

<400> SEQUENCE: 145

Leu Ile Tyr Trp Asp Asp Asp Lys Arg Tyr Ser Pro Ser Leu Lys Ser
1               5                   10                  15

<210> SEQ ID NO 146
<211> LENGTH: 16
<212> TYPE: PRT
<213> ORGANISM: Homo sapiens

<400> SEQUENCE: 146

Phe Ile Asp Trp Asp Asp Asp Lys Tyr Tyr Thr Thr Ser Leu Lys Thr
1               5                   10                  15

<210> SEQ ID NO 147
<211> LENGTH: 17
<212> TYPE: PRT
<213> ORGANISM: Homo sapiens

<400> SEQUENCE: 147

Asn Ile Asn Gln Glu Gly Ser Ala Lys His Tyr Val Asp Ser Val Lys
1               5                   10                  15

Gly

<210> SEQ ID NO 148
<211> LENGTH: 17
<212> TYPE: PRT
<213> ORGANISM: Homo sapiens

<400> SEQUENCE: 148

Leu Ile Ser Tyr His Gly Asn Thr Lys Tyr Tyr Ala Asp Ser Val Lys
1               5                   10                  15

Gly

<210> SEQ ID NO 149
<211> LENGTH: 17
<212> TYPE: PRT
<213> ORGANISM: Homo sapiens

<400> SEQUENCE: 149

Ile Ile Asn Pro Ser Gly Gly Ser Thr Thr Tyr Ala Gln Arg Phe Gln
1               5                   10                  15

Gly

<210> SEQ ID NO 150
<211> LENGTH: 17
<212> TYPE: PRT
<213> ORGANISM: Homo sapiens

<400> SEQUENCE: 150

Gly Cys Ser Trp Asn Ser Gly Phe Ile Ser Tyr Ala Asp Ser Val Lys
1               5                   10                  15

Gly

<210> SEQ ID NO 151
<211> LENGTH: 16
<212> TYPE: PRT
<213> ORGANISM: Homo sapiens

<400> SEQUENCE: 151

Glu Ile Asn His Ser Ala Asn Thr Asp Tyr Lys Pro Ser Leu Lys Ser
1               5                   10                  15

<210> SEQ ID NO 152
<211> LENGTH: 17
<212> TYPE: PRT
<213> ORGANISM: Homo sapiens

<400> SEQUENCE: 152

Ile Ile Tyr Pro Gly Asp Ser Asp Thr Arg Tyr Ser Pro Ser Phe Gln
1               5                   10                  15

Gly

<210> SEQ ID NO 153
<211> LENGTH: 17
<212> TYPE: PRT
<213> ORGANISM: Homo sapiens

<400> SEQUENCE: 153

Ala Ile Thr Ser Ser Thr Thr Tyr Ile Tyr Tyr Ala Asp Ser Val Lys
1               5                   10                  15

Gly

<210> SEQ ID NO 154
<211> LENGTH: 17
<212> TYPE: PRT
<213> ORGANISM: Homo sapiens

<400> SEQUENCE: 154

Ile Ile Tyr Pro Glu Asp Gly Asp Thr Arg Tyr Ser Pro Ala Phe Gln
1               5                   10                  15

Gly

<210> SEQ ID NO 155
<211> LENGTH: 17
<212> TYPE: PRT
<213> ORGANISM: Homo sapiens

<400> SEQUENCE: 155

Trp Ile Asn Val Gly Asn Gly Gln Thr Lys Phe Ser Gln Arg Phe Gln
1               5                   10                  15

Gly

<210> SEQ ID NO 156
<211> LENGTH: 16
<212> TYPE: PRT
<213> ORGANISM: Homo sapiens

<400> SEQUENCE: 156

Asn Ile Tyr Ser Thr Gly Ser Thr Tyr Tyr Asp Pro Ser Leu Gln Asn
1               5                   10                  15

<210> SEQ ID NO 157
<211> LENGTH: 17
<212> TYPE: PRT
<213> ORGANISM: Homo sapiens

<400> SEQUENCE: 157

Thr Ile Ser Tyr Asp Val Lys Asn Lys Asp Tyr Ala Asp Ser Val Lys
1               5                   10                  15

Gly

<210> SEQ ID NO 158

```
<211> LENGTH: 17
<212> TYPE: PRT
<213> ORGANISM: Homo sapiens

<400> SEQUENCE: 158

Trp Ile Ser Ala Trp Asp Gly Asn Thr Lys Tyr Gly Glu Lys Phe Gln
1               5                   10                  15
Asp

<210> SEQ ID NO 159
<211> LENGTH: 16
<212> TYPE: PRT
<213> ORGANISM: Homo sapiens

<400> SEQUENCE: 159

Glu Ile Tyr His Ser Gly Asn Thr Asn Tyr Asn Pro Ser Leu Gln Ser
1               5                   10                  15

<210> SEQ ID NO 160
<211> LENGTH: 17
<212> TYPE: PRT
<213> ORGANISM: Homo sapiens

<400> SEQUENCE: 160

Met Ile Asn Pro Ser Gly Gly Thr Thr Thr Tyr Ala Gln Lys Phe Gln
1               5                   10                  15
Gly

<210> SEQ ID NO 161
<211> LENGTH: 16
<212> TYPE: PRT
<213> ORGANISM: Homo sapiens

<400> SEQUENCE: 161

Tyr Ile Tyr Tyr Thr Gly Ser Thr Tyr Tyr Asn Pro Ser Leu Lys Ser
1               5                   10                  15

<210> SEQ ID NO 162
<211> LENGTH: 17
<212> TYPE: PRT
<213> ORGANISM: Homo sapiens

<400> SEQUENCE: 162

Ile Val Leu Tyr Asp Gly Lys Asn Lys Asn Tyr Ala Asp Ser Val Arg
1               5                   10                  15
Gly

<210> SEQ ID NO 163
<211> LENGTH: 17
<212> TYPE: PRT
<213> ORGANISM: Homo sapiens

<400> SEQUENCE: 163

Gly Ile Ser Trp Asn Ser Glu Tyr Ile Gly Tyr Glu Asp Ser Val Lys
1               5                   10                  15
Gly

<210> SEQ ID NO 164
<211> LENGTH: 17
<212> TYPE: PRT
<213> ORGANISM: Homo sapiens

<400> SEQUENCE: 164
```

```
Thr Ile Ser Trp Asn Ser Gly Phe Ile Asp Tyr Ala Asp Ser Val Lys
1               5                   10                  15

Gly

<210> SEQ ID NO 165
<211> LENGTH: 17
<212> TYPE: PRT
<213> ORGANISM: Homo sapiens

<400> SEQUENCE: 165

Trp Ile Asn Pro Asn Phe Gly Gly Thr Asp Tyr Ala Gln Lys Phe Gln
1               5                   10                  15

Gly

<210> SEQ ID NO 166
<211> LENGTH: 17
<212> TYPE: PRT
<213> ORGANISM: Homo sapiens

<400> SEQUENCE: 166

Trp Ile Ser Ala Tyr Asn Gly Asn Thr Asp Tyr Ala Gln Lys Phe Gln
1               5                   10                  15

Gly

<210> SEQ ID NO 167
<211> LENGTH: 16
<212> TYPE: PRT
<213> ORGANISM: Homo sapiens

<400> SEQUENCE: 167

Glu Ile Asn His Ser Gly Ser Ala Asn Tyr His Pro Ser Leu Lys Ser
1               5                   10                  15

<210> SEQ ID NO 168
<211> LENGTH: 19
<212> TYPE: PRT
<213> ORGANISM: Homo sapiens

<400> SEQUENCE: 168

Leu Ile Arg Ser Arg His Tyr Gly Ala Lys Thr Gln Phe Ala Ala Ser
1               5                   10                  15

Val Gln Gly

<210> SEQ ID NO 169
<211> LENGTH: 16
<212> TYPE: PRT
<213> ORGANISM: Homo sapiens

<400> SEQUENCE: 169

Thr Ile Tyr Tyr Thr Gly Arg Thr Tyr Tyr Asn Pro Ser Leu Lys Asn
1               5                   10                  15

<210> SEQ ID NO 170
<211> LENGTH: 16
<212> TYPE: PRT
<213> ORGANISM: Homo sapiens

<400> SEQUENCE: 170

Thr Val Tyr Leu Ser Gly Arg Ala Tyr Tyr Asn Pro Ser Leu Lys Ser
1               5                   10                  15
```

```
<210> SEQ ID NO 171
<211> LENGTH: 18
<212> TYPE: PRT
<213> ORGANISM: Homo sapiens

<400> SEQUENCE: 171

Arg Thr Tyr Tyr Arg Ser Arg Trp Arg Asn Asp Tyr Ala Gly Ser Val
1               5                   10                  15

Arg Ser

<210> SEQ ID NO 172
<211> LENGTH: 17
<212> TYPE: PRT
<213> ORGANISM: Homo sapiens

<400> SEQUENCE: 172

Gly Ile Asn Trp Asn Ser Gly Asn Ile Val Tyr Ala Asp Ser Val Lys
1               5                   10                  15

Gly

<210> SEQ ID NO 173
<211> LENGTH: 17
<212> TYPE: PRT
<213> ORGANISM: Homo sapiens

<400> SEQUENCE: 173

Leu Val Asp Pro Glu Asp Gly Glu Pro Ile Tyr Ala Glu Lys Phe Gln
1               5                   10                  15

Gly

<210> SEQ ID NO 174
<211> LENGTH: 17
<212> TYPE: PRT
<213> ORGANISM: Homo sapiens

<400> SEQUENCE: 174

Ile Ile Tyr Gly Gly Asp Ser Asp Thr Lys Tyr Ser Pro Ser Phe Gln
1               5                   10                  15

Gly

<210> SEQ ID NO 175
<211> LENGTH: 17
<212> TYPE: PRT
<213> ORGANISM: Homo sapiens

<400> SEQUENCE: 175

Ile Ile Phe Pro Gly Asp Ser Asp Thr Arg Tyr Ser Pro Ser Phe Gln
1               5                   10                  15

Gly

<210> SEQ ID NO 176
<211> LENGTH: 17
<212> TYPE: PRT
<213> ORGANISM: Homo sapiens

<400> SEQUENCE: 176

Gly Val Ser Trp Asn Ser Asp Val Ile Asn Tyr Ser Asp Ser Val Lys
1               5                   10                  15

Gly

<210> SEQ ID NO 177
```

```
<211> LENGTH: 17
<212> TYPE: PRT
<213> ORGANISM: Homo sapiens

<400> SEQUENCE: 177

Gly Ile Ile Pro Val Phe Gly Thr Pro Asn Tyr Ala Gln Gln Phe Gln
1               5                   10                  15

Gly

<210> SEQ ID NO 178
<211> LENGTH: 16
<212> TYPE: PRT
<213> ORGANISM: Homo sapiens

<400> SEQUENCE: 178

Leu Ile Tyr Trp Asp Asp Glu Glu Arg Tyr Ser Pro Ser Leu Lys Asn
1               5                   10                  15

<210> SEQ ID NO 179
<211> LENGTH: 17
<212> TYPE: PRT
<213> ORGANISM: Homo sapiens

<400> SEQUENCE: 179

Ser Ile Ile Pro Ile Phe Ala Thr Thr Asn Tyr Ala Gln Arg Phe Gln
1               5                   10                  15

Gly

<210> SEQ ID NO 180
<211> LENGTH: 16
<212> TYPE: PRT
<213> ORGANISM: Homo sapiens

<400> SEQUENCE: 180

Glu Val Asn His Ser Gly Ser Thr Asn Tyr Asn Pro Ser Leu Arg Ser
1               5                   10                  15

<210> SEQ ID NO 181
<211> LENGTH: 17
<212> TYPE: PRT
<213> ORGANISM: Homo sapiens

<400> SEQUENCE: 181

Trp Ile Thr Tyr Asp Lys Gly Asn Thr Asn His Ala Gln Lys Phe Arg
1               5                   10                  15

Gly

<210> SEQ ID NO 182
<211> LENGTH: 17
<212> TYPE: PRT
<213> ORGANISM: Homo sapiens

<400> SEQUENCE: 182

Gly Val Val Pro Ile Tyr Asp Thr Ser His Tyr Ala Gln Lys Phe Lys
1               5                   10                  15

Gly

<210> SEQ ID NO 183
<211> LENGTH: 17
<212> TYPE: PRT
<213> ORGANISM: Homo sapiens

<400> SEQUENCE: 183
```

```
Gly Ile Ile Pro Ile Phe Gly Thr Thr Asn Tyr Ala Gln Lys Phe Gln
1               5                   10                  15

Gly
```

<210> SEQ ID NO 184
<211> LENGTH: 17
<212> TYPE: PRT
<213> ORGANISM: Homo sapiens

<400> SEQUENCE: 184

```
Ala Ile Ser Gly Ser Gly Gly Lys Thr Tyr His Ala His Ser Val Arg
1               5                   10                  15

Gly
```

<210> SEQ ID NO 185
<211> LENGTH: 17
<212> TYPE: PRT
<213> ORGANISM: Homo sapiens

<400> SEQUENCE: 185

```
Tyr Ile Ser Ser Thr Ser Gly Ser Ile Tyr Tyr Ala Asp Ser Val Lys
1               5                   10                  15

Gly
```

<210> SEQ ID NO 186
<211> LENGTH: 17
<212> TYPE: PRT
<213> ORGANISM: Homo sapiens

<400> SEQUENCE: 186

```
Gly Leu Asn Trp Asn Gly Ala Asn Ile Arg Tyr Ala Asp Ser Val Lys
1               5                   10                  15

Gly
```

<210> SEQ ID NO 187
<211> LENGTH: 16
<212> TYPE: PRT
<213> ORGANISM: Homo sapiens

<400> SEQUENCE: 187

```
Leu Ile Tyr Trp Asp Asp Asp Lys Arg Tyr Ser Pro Ser Leu Lys Ser
1               5                   10                  15
```

<210> SEQ ID NO 188
<211> LENGTH: 17
<212> TYPE: PRT
<213> ORGANISM: Homo sapiens

<400> SEQUENCE: 188

```
Phe Ile Ser Ser Asp Gly Ser Thr Lys Tyr Tyr Ala Asp Ser Val Lys
1               5                   10                  15

Gly
```

<210> SEQ ID NO 189
<211> LENGTH: 17
<212> TYPE: PRT
<213> ORGANISM: Homo sapiens

<400> SEQUENCE: 189

```
Phe Ile Ser Tyr Asp Gly Ser Lys Lys Tyr Tyr Val Asp Ser Val Lys
1               5                   10                  15
```

Gly

<210> SEQ ID NO 190
<211> LENGTH: 16
<212> TYPE: PRT
<213> ORGANISM: Homo sapiens

<400> SEQUENCE: 190

Tyr Ile Tyr Lys Thr Gly Ser Thr Asn Tyr Asn Pro Ser Leu Lys Ser
1               5                   10                  15

<210> SEQ ID NO 191
<211> LENGTH: 17
<212> TYPE: PRT
<213> ORGANISM: Homo sapiens

<400> SEQUENCE: 191

Val Thr Tyr Pro Gly Asp Ser Asp Thr Arg Tyr Ser Pro Ser Phe Gln
1               5                   10                  15

Gly

<210> SEQ ID NO 192
<211> LENGTH: 17
<212> TYPE: PRT
<213> ORGANISM: Homo sapiens

<400> SEQUENCE: 192

Gly Ile Ile Trp Asn Ser Glu Tyr Ile Gly Tyr Ala Asp Ser Val Lys
1               5                   10                  15

Gly

<210> SEQ ID NO 193
<211> LENGTH: 17
<212> TYPE: PRT
<213> ORGANISM: Homo sapiens

<400> SEQUENCE: 193

Leu Ile Asn Pro Ser Ser Gly Thr Thr Ser Tyr Ala Gln Asn Phe Gln
1               5                   10                  15

Gly

<210> SEQ ID NO 194
<211> LENGTH: 16
<212> TYPE: PRT
<213> ORGANISM: Homo sapiens

<400> SEQUENCE: 194

Tyr Ile Tyr Tyr Ser Gly Ser Thr Asn Tyr Asn Pro Ser Leu Lys Ser
1               5                   10                  15

<210> SEQ ID NO 195
<211> LENGTH: 17
<212> TYPE: PRT
<213> ORGANISM: Homo sapiens

<400> SEQUENCE: 195

Ser Ile Ile Pro Ile Phe Gly Thr Ala His Tyr Ala Gln Arg Phe Glu
1               5                   10                  15

Gly

<210> SEQ ID NO 196

```
<211> LENGTH: 17
<212> TYPE: PRT
<213> ORGANISM: Homo sapiens

<400> SEQUENCE: 196

Gly Ile Arg Val His Asn Gly Asn Thr Asn Tyr Ala Gln Lys Phe Gln
1               5                   10                  15
Gly

<210> SEQ ID NO 197
<211> LENGTH: 16
<212> TYPE: PRT
<213> ORGANISM: Homo sapiens

<400> SEQUENCE: 197

Tyr Ile His Tyr Thr Gly Thr Thr Tyr Asn Pro Ser Leu Lys Ser
1               5                   10                  15

<210> SEQ ID NO 198
<211> LENGTH: 17
<212> TYPE: PRT
<213> ORGANISM: Homo sapiens

<400> SEQUENCE: 198

Ile Ile Tyr Pro Gly Asp Ser Asp Thr Arg Tyr Ser Pro Ser Phe Gln
1               5                   10                  15
Gly

<210> SEQ ID NO 199
<211> LENGTH: 16
<212> TYPE: PRT
<213> ORGANISM: Homo sapiens

<400> SEQUENCE: 199

Tyr Ile His Tyr Ser Gly Ser Thr Tyr Asn Pro Ser Leu Lys Ser
1               5                   10                  15

<210> SEQ ID NO 200
<211> LENGTH: 17
<212> TYPE: PRT
<213> ORGANISM: Homo sapiens

<400> SEQUENCE: 200

Tyr Thr Asn Leu Phe Thr Gly Tyr Thr Asn Tyr Ala Asp Ser Val Lys
1               5                   10                  15
Gly

<210> SEQ ID NO 201
<211> LENGTH: 16
<212> TYPE: PRT
<213> ORGANISM: Homo sapiens

<400> SEQUENCE: 201

Tyr Ile Tyr Tyr Thr Gly Asn Thr Tyr Phe Asn Pro Ser Leu Lys Ser
1               5                   10                  15

<210> SEQ ID NO 202
<211> LENGTH: 16
<212> TYPE: PRT
<213> ORGANISM: Homo sapiens

<400> SEQUENCE: 202

Glu Ile Ser His Ser Gly Ser Thr His Tyr Asn Pro Ser Leu Asn Ser
```

-continued

```
                1               5                  10                 15

<210> SEQ ID NO 203
<211> LENGTH: 19
<212> TYPE: PRT
<213> ORGANISM: Homo sapiens

<400> SEQUENCE: 203

Phe Ile Arg Gly Lys Lys Phe Gly Gly Thr Lys Asp Tyr Ala Ala Ser
1               5                   10                  15

Val Lys Gly

<210> SEQ ID NO 204
<211> LENGTH: 17
<212> TYPE: PRT
<213> ORGANISM: Homo sapiens

<400> SEQUENCE: 204

Lys Ile Ile Pro Ile Tyr Gly Arg Ala Asn Tyr Ala Gln Lys Phe Gln
1               5                   10                  15

Gly

<210> SEQ ID NO 205
<211> LENGTH: 16
<212> TYPE: PRT
<213> ORGANISM: Homo sapiens

<400> SEQUENCE: 205

Glu Ile Tyr His Ser Gly Ser Thr Asn Tyr Asn Pro Ser Leu Lys Ser
1               5                   10                  15

<210> SEQ ID NO 206
<211> LENGTH: 17
<212> TYPE: PRT
<213> ORGANISM: Homo sapiens

<400> SEQUENCE: 206

Gly Ile Val Pro Met Val Gly Pro Ala Asp Tyr Ala Glu Lys Phe Arg
1               5                   10                  15

Gly

<210> SEQ ID NO 207
<211> LENGTH: 17
<212> TYPE: PRT
<213> ORGANISM: Homo sapiens

<400> SEQUENCE: 207

Leu Ile Asn Pro Ser Gly Asp Ser Thr Thr Asn Ala Gln Lys Phe Gln
1               5                   10                  15

Gly

<210> SEQ ID NO 208
<211> LENGTH: 17
<212> TYPE: PRT
<213> ORGANISM: Homo sapiens

<400> SEQUENCE: 208

Gly Ile Ile Pro Ile Phe Gly Thr Pro Asn Tyr Ser Leu Lys Phe Gln
1               5                   10                  15

Asp
```

```
<210> SEQ ID NO 209
<211> LENGTH: 16
<212> TYPE: PRT
<213> ORGANISM: Homo sapiens

<400> SEQUENCE: 209

His Ile Phe Ser Asn Asp Glu Arg Ser His Ser Ser Leu Lys Ser
1               5                   10                  15

<210> SEQ ID NO 210
<211> LENGTH: 16
<212> TYPE: PRT
<213> ORGANISM: Homo sapiens

<400> SEQUENCE: 210

Tyr Ile Phe Tyr Ser Gly Asn Thr Asn Tyr Asn Pro Ser Leu Lys Ser
1               5                   10                  15

<210> SEQ ID NO 211
<211> LENGTH: 16
<212> TYPE: PRT
<213> ORGANISM: Homo sapiens

<400> SEQUENCE: 211

Glu Ile Asn Gln Asn Gly Arg Ser Asn His Asn Pro Ser Leu Lys Ser
1               5                   10                  15

<210> SEQ ID NO 212
<211> LENGTH: 17
<212> TYPE: PRT
<213> ORGANISM: Homo sapiens

<400> SEQUENCE: 212

Val Ile Ser Tyr Asp Gly Arg Tyr Lys Phe Tyr Ala Asn Ser Val Lys
1               5                   10                  15

Gly

<210> SEQ ID NO 213
<211> LENGTH: 17
<212> TYPE: PRT
<213> ORGANISM: Homo sapiens

<400> SEQUENCE: 213

Ile Ile His Pro Gly Asp Ser Glu Thr Arg Tyr Ser Pro Ser Phe Gln
1               5                   10                  15

Gly

<210> SEQ ID NO 214
<211> LENGTH: 17
<212> TYPE: PRT
<213> ORGANISM: Homo sapiens

<400> SEQUENCE: 214

Val Ile Ser Tyr Asp Gly Thr Asn Lys Tyr His Thr Asp Ser Val Lys
1               5                   10                  15

Gly

<210> SEQ ID NO 215
<211> LENGTH: 17
<212> TYPE: PRT
<213> ORGANISM: Homo sapiens

<400> SEQUENCE: 215
```

-continued

```
Glu Ile Ile Pro Lys Phe Gly Thr Ala Asn Tyr Ala Gln Lys Phe Gln
1               5                   10                  15

Gly

<210> SEQ ID NO 216
<211> LENGTH: 17
<212> TYPE: PRT
<213> ORGANISM: Homo sapiens

<400> SEQUENCE: 216

Leu Ile Asn Pro Ser Ala Gly Lys Thr Thr Tyr Ala Gln Arg Phe Gln
1               5                   10                  15

Gly

<210> SEQ ID NO 217
<211> LENGTH: 17
<212> TYPE: PRT
<213> ORGANISM: Homo sapiens

<400> SEQUENCE: 217

Gly Ile Ile Pro Val Phe Gly Thr Thr Asn Tyr Ala Gln Ser Leu Gln
1               5                   10                  15

Gly

<210> SEQ ID NO 218
<211> LENGTH: 16
<212> TYPE: PRT
<213> ORGANISM: Homo sapiens

<400> SEQUENCE: 218

Tyr Val Phe Asn Ser Gly Ser Thr Tyr Tyr Asn Pro Ser Leu Gln Ser
1               5                   10                  15

<210> SEQ ID NO 219
<211> LENGTH: 16
<212> TYPE: PRT
<213> ORGANISM: Homo sapiens

<400> SEQUENCE: 219

Tyr Ile Asp Tyr Arg Gly Thr Thr Tyr Tyr Ser Pro Ser Phe Lys Ser
1               5                   10                  15

<210> SEQ ID NO 220
<211> LENGTH: 17
<212> TYPE: PRT
<213> ORGANISM: Homo sapiens

<400> SEQUENCE: 220

Arg Ile Asn Pro Ile Thr Asp Val Thr Asn Tyr Ala Gln Ile Phe Gln
1               5                   10                  15

Gly

<210> SEQ ID NO 221
<211> LENGTH: 17
<212> TYPE: PRT
<213> ORGANISM: Homo sapiens

<400> SEQUENCE: 221

Arg Ile Asn Pro Asp Ser Gly Thr Asp Phe Ser Gln Lys Phe Gln
1               5                   10                  15

Gly
```

```
<210> SEQ ID NO 222
<211> LENGTH: 17
<212> TYPE: PRT
<213> ORGANISM: Homo sapiens

<400> SEQUENCE: 222

Tyr Ile Gly Ser Gly Gly Val Thr Ile Tyr Tyr Ala Asp Ser Val Lys
1               5                   10                  15

Gly

<210> SEQ ID NO 223
<211> LENGTH: 17
<212> TYPE: PRT
<213> ORGANISM: Homo sapiens

<400> SEQUENCE: 223

Ile Ile Trp Pro Val Asp Ser Asp Thr Arg Tyr Ser Pro Ser Phe Gln
1               5                   10                  15

Gly

<210> SEQ ID NO 224
<211> LENGTH: 17
<212> TYPE: PRT
<213> ORGANISM: Homo sapiens

<400> SEQUENCE: 224

Trp Ile Asn Thr Asn Thr Gly Asn Pro Thr Tyr Ala Gln Gly Phe Thr
1               5                   10                  15

Gly

<210> SEQ ID NO 225
<211> LENGTH: 16
<212> TYPE: PRT
<213> ORGANISM: Homo sapiens

<400> SEQUENCE: 225

Tyr Ser Ser Asn Arg Gly Ile Ala Tyr Tyr Asn Pro Ser Leu Lys Ser
1               5                   10                  15

<210> SEQ ID NO 226
<211> LENGTH: 17
<212> TYPE: PRT
<213> ORGANISM: Homo sapiens

<400> SEQUENCE: 226

Gly Ile Ile Pro Phe Ala Gln Lys Val Leu Gly Ala Gln Arg Val Arg
1               5                   10                  15

Asp

<210> SEQ ID NO 227
<211> LENGTH: 17
<212> TYPE: PRT
<213> ORGANISM: Homo sapiens

<400> SEQUENCE: 227

Arg Ile Asn Pro Lys Ser Gly Asp Thr His His Val Gln Lys Phe Gln
1               5                   10                  15

Gly

<210> SEQ ID NO 228
<211> LENGTH: 20
```

```
<212> TYPE: PRT
<213> ORGANISM: Homo sapiens

<400> SEQUENCE: 228

Cys Ala Thr Asp Val Trp Arg Arg Thr Pro Glu Gly Gly Thr Asp Trp
1               5                   10                  15

Phe Asp Pro Trp
            20

<210> SEQ ID NO 229
<211> LENGTH: 26
<212> TYPE: PRT
<213> ORGANISM: Homo sapiens

<400> SEQUENCE: 229

Cys Ala Gly Ser Arg Ser Phe Asp Leu Leu Thr Ala Tyr Asp Leu Phe
1               5                   10                  15

His Arg Lys Gly Asn Ala Met Asp Val Trp
            20                  25

<210> SEQ ID NO 230
<211> LENGTH: 13
<212> TYPE: PRT
<213> ORGANISM: Homo sapiens

<400> SEQUENCE: 230

Cys Ala Arg Gly Asp Val Leu Arg Tyr Phe Asp Tyr Trp
1               5                   10

<210> SEQ ID NO 231
<211> LENGTH: 14
<212> TYPE: PRT
<213> ORGANISM: Homo sapiens

<400> SEQUENCE: 231

Cys Ala Lys Gly Gly Leu Gly Thr Asn Glu Phe Asp His Trp
1               5                   10

<210> SEQ ID NO 232
<211> LENGTH: 18
<212> TYPE: PRT
<213> ORGANISM: Homo sapiens

<400> SEQUENCE: 232

Cys Ala Thr Leu Pro Arg Tyr Asp Ala Tyr Gly Ala Arg Ile Arg Asp
1               5                   10                  15

Tyr Trp

<210> SEQ ID NO 233
<211> LENGTH: 14
<212> TYPE: PRT
<213> ORGANISM: Homo sapiens

<400> SEQUENCE: 233

Cys Ala Arg Tyr Cys Ser Ser Pro Thr Cys Ser Ile Val Trp
1               5                   10

<210> SEQ ID NO 234
<211> LENGTH: 15
<212> TYPE: PRT
<213> ORGANISM: Homo sapiens

<400> SEQUENCE: 234
```

```
Cys Ala His Ser Ser Gln Arg Val Val Thr Gly Leu Asp Phe Trp
1               5                   10                  15
```

<210> SEQ ID NO 235
<211> LENGTH: 22
<212> TYPE: PRT
<213> ORGANISM: Homo sapiens

<400> SEQUENCE: 235

```
Cys Ala Arg Ile Arg Thr Cys Tyr Pro Asp Leu Tyr Gly Asp Tyr Asn
1               5                   10                  15

Asp Ala Phe Asp Ile Trp
            20
```

<210> SEQ ID NO 236
<211> LENGTH: 13
<212> TYPE: PRT
<213> ORGANISM: Homo sapiens

<400> SEQUENCE: 236

```
Cys Ala Arg Ala Ala Asp Tyr Gly Asp Tyr Val Arg Pro
1               5                   10
```

<210> SEQ ID NO 237
<211> LENGTH: 14
<212> TYPE: PRT
<213> ORGANISM: Homo sapiens

<400> SEQUENCE: 237

```
Cys Ala Lys His Val Ala Ala Gly Gly Thr Leu Asp Tyr Trp
1               5                   10
```

<210> SEQ ID NO 238
<211> LENGTH: 24
<212> TYPE: PRT
<213> ORGANISM: Homo sapiens

<400> SEQUENCE: 238

```
Cys Ala Arg Val Ile Arg Lys Tyr Tyr Thr Ser Ser Asn Ser Tyr Leu
1               5                   10                  15

Thr Glu Gln Ala Phe Asp Ile Trp
            20
```

<210> SEQ ID NO 239
<211> LENGTH: 16
<212> TYPE: PRT
<213> ORGANISM: Homo sapiens

<400> SEQUENCE: 239

```
Cys Val Lys Glu Thr Val Ala Gly Arg Arg Gly Ala Phe Asp Tyr Trp
1               5                   10                  15
```

<210> SEQ ID NO 240
<211> LENGTH: 14
<212> TYPE: PRT
<213> ORGANISM: Homo sapiens

<400> SEQUENCE: 240

```
Cys Ala Arg Gly Arg Glu Trp Pro Ser Asn Phe Asp Ser Trp
1               5                   10
```

<210> SEQ ID NO 241
<211> LENGTH: 13
<212> TYPE: PRT

```
<213> ORGANISM: Homo sapiens

<400> SEQUENCE: 241

Cys Ala Arg Arg Gly Ser Thr Tyr Tyr Tyr Asp Thr Trp
1               5                   10

<210> SEQ ID NO 242
<211> LENGTH: 14
<212> TYPE: PRT
<213> ORGANISM: Homo sapiens

<400> SEQUENCE: 242

Cys Ala Ser Lys Pro Tyr Gly Gly Asp Phe Gly Ser Tyr Trp
1               5                   10

<210> SEQ ID NO 243
<211> LENGTH: 15
<212> TYPE: PRT
<213> ORGANISM: Homo sapiens

<400> SEQUENCE: 243

Cys Ala Arg Pro Pro Ser Asn Trp Asp Glu Ser Phe Asp Ile Trp
1               5                   10                  15

<210> SEQ ID NO 244
<211> LENGTH: 20
<212> TYPE: PRT
<213> ORGANISM: Homo sapiens

<400> SEQUENCE: 244

Cys Ala Arg Asp Pro Thr Gln Trp Leu Leu Gln Gly Asp Val Tyr Asp
1               5                   10                  15

Met Asp Val Trp
            20

<210> SEQ ID NO 245
<211> LENGTH: 21
<212> TYPE: PRT
<213> ORGANISM: Homo sapiens

<400> SEQUENCE: 245

Cys Ala Arg Glu Ala Trp Leu Gly Glu Pro Leu Leu Leu Gly Asp Asp
1               5                   10                  15

Ala Phe Asp Ile Trp
            20

<210> SEQ ID NO 246
<211> LENGTH: 20
<212> TYPE: PRT
<213> ORGANISM: Homo sapiens

<400> SEQUENCE: 246

Cys Ala Arg Asp Gly Ala Gly Glu Trp Asp Leu Leu Met Arg Arg Asp
1               5                   10                  15

Phe Asp Tyr Trp
            20

<210> SEQ ID NO 247
<211> LENGTH: 19
<212> TYPE: PRT
<213> ORGANISM: Homo sapiens

<400> SEQUENCE: 247
```

-continued

Cys Ala Arg Asp Pro Ala Arg Arg Pro Arg Ser Gly Tyr Ser Val Phe
1               5                   10                  15

Glu Tyr Trp

<210> SEQ ID NO 248
<211> LENGTH: 24
<212> TYPE: PRT
<213> ORGANISM: Homo sapiens

<400> SEQUENCE: 248

Cys Ala Arg Asp Asn Arg Gln Ser Ser Ser Trp Val Glu Gly Phe Phe
1               5                   10                  15

Tyr Tyr Tyr Gly Met Asp Val Trp
            20

<210> SEQ ID NO 249
<211> LENGTH: 16
<212> TYPE: PRT
<213> ORGANISM: Homo sapiens

<400> SEQUENCE: 249

Cys Ala Arg Leu Arg Leu Gly Ala Thr Ile Gly Arg Asp Asp Tyr Trp
1               5                   10                  15

<210> SEQ ID NO 250
<211> LENGTH: 19
<212> TYPE: PRT
<213> ORGANISM: Homo sapiens

<400> SEQUENCE: 250

Cys Ala Arg Asp Arg Ala Ser Ser Gly Tyr Asp Ser Arg Val Trp Phe
1               5                   10                  15

Asp Pro Trp

<210> SEQ ID NO 251
<211> LENGTH: 17
<212> TYPE: PRT
<213> ORGANISM: Homo sapiens

<400> SEQUENCE: 251

Cys Ala Arg Thr Tyr Arg Val Tyr Ala Lys Phe Asp Pro Phe Asp Val
1               5                   10                  15

Trp

<210> SEQ ID NO 252
<211> LENGTH: 16
<212> TYPE: PRT
<213> ORGANISM: Homo sapiens

<400> SEQUENCE: 252

Cys Gly Lys Asp Gly Val Pro Gly Arg Arg Gly Tyr Ile Glu Asp Trp
1               5                   10                  15

<210> SEQ ID NO 253
<211> LENGTH: 16
<212> TYPE: PRT
<213> ORGANISM: Homo sapiens

<400> SEQUENCE: 253

Cys Val Lys Asp Asn Ile Ala Gly Arg Arg Gly Ser Phe Asp Ser Trp
1               5                   10                  15

<210> SEQ ID NO 254
<211> LENGTH: 26
<212> TYPE: PRT
<213> ORGANISM: Homo sapiens

<400> SEQUENCE: 254

Cys Ala Arg Asp Tyr Ile Arg Ala Thr Gly Ala Thr Pro Ser Lys Tyr
1               5                   10                  15

Phe Ile Tyr Tyr Tyr Gly Met Gly Val Trp
            20                  25

<210> SEQ ID NO 255
<211> LENGTH: 18
<212> TYPE: PRT
<213> ORGANISM: Homo sapiens

<400> SEQUENCE: 255

Cys Ala Arg Ala Arg Arg Val Thr Asn Ser Pro Asn Asn Trp Phe Asp
1               5                   10                  15

Pro Trp

<210> SEQ ID NO 256
<211> LENGTH: 21
<212> TYPE: PRT
<213> ORGANISM: Homo sapiens

<400> SEQUENCE: 256

Cys Ala Arg Ala Gly Glu Arg Ser Gly Ser Gly Ser Phe Val Leu Gly
1               5                   10                  15

Arg Phe Asp Phe Trp
            20

<210> SEQ ID NO 257
<211> LENGTH: 13
<212> TYPE: PRT
<213> ORGANISM: Homo sapiens

<400> SEQUENCE: 257

Cys Thr Asn Thr Ser Ser Leu Ala Val Ala Gly Asn Trp
1               5                   10

<210> SEQ ID NO 258
<211> LENGTH: 15
<212> TYPE: PRT
<213> ORGANISM: Homo sapiens

<400> SEQUENCE: 258

Cys Ala Arg Ile Pro Gln Gln Arg Val Asn Tyr Phe Asp Tyr Trp
1               5                   10                  15

<210> SEQ ID NO 259
<211> LENGTH: 15
<212> TYPE: PRT
<213> ORGANISM: Homo sapiens

<400> SEQUENCE: 259

Cys Ala Arg Leu Pro Gly Gln Arg Thr Thr Phe Phe Asp Tyr Trp
1               5                   10                  15

<210> SEQ ID NO 260
<211> LENGTH: 15
<212> TYPE: PRT
<213> ORGANISM: Homo sapiens

```
<400> SEQUENCE: 260

Cys Ala Arg Gly Arg Arg Phe Glu Asp Asp Ala Phe Asp Ile Trp
1               5                   10                  15

<210> SEQ ID NO 261
<211> LENGTH: 16
<212> TYPE: PRT
<213> ORGANISM: Homo sapiens

<400> SEQUENCE: 261

Cys Val Lys Asp Ser Val Ala Gly Arg Arg Gly Gly Phe Asp His Trp
1               5                   10                  15

<210> SEQ ID NO 262
<211> LENGTH: 11
<212> TYPE: PRT
<213> ORGANISM: Homo sapiens

<400> SEQUENCE: 262

Cys Ala Thr Arg Asp Gly Asp Phe Asp His Trp
1               5                   10

<210> SEQ ID NO 263
<211> LENGTH: 19
<212> TYPE: PRT
<213> ORGANISM: Homo sapiens

<400> SEQUENCE: 263

Cys Val Arg His Gly Thr Arg Tyr Ser Phe Gly Arg Ser Asp Ile Ile
1               5                   10                  15

Asp Ile Trp

<210> SEQ ID NO 264
<211> LENGTH: 18
<212> TYPE: PRT
<213> ORGANISM: Homo sapiens

<400> SEQUENCE: 264

Cys Thr Lys Thr Pro Ala Arg Gly Ala Tyr Gly Asp Tyr Ile Ser Gly
1               5                   10                  15

Ser Trp

<210> SEQ ID NO 265
<211> LENGTH: 16
<212> TYPE: PRT
<213> ORGANISM: Homo sapiens

<400> SEQUENCE: 265

Cys Ala Lys Ser Thr Lys Ala Val Arg Arg Gly Ser Phe Asp Tyr Trp
1               5                   10                  15

<210> SEQ ID NO 266
<211> LENGTH: 22
<212> TYPE: PRT
<213> ORGANISM: Homo sapiens

<400> SEQUENCE: 266

Cys Ala Arg Gly Gly Lys Leu Tyr Glu Gly Asn Gly Tyr Tyr Ser Phe
1               5                   10                  15

His Tyr Phe Asp Tyr Trp
                20
```

```
<210> SEQ ID NO 267
<211> LENGTH: 11
<212> TYPE: PRT
<213> ORGANISM: Homo sapiens

<400> SEQUENCE: 267

Cys Ala His Thr Glu Leu Ala Phe Asp Tyr Trp
1               5                   10

<210> SEQ ID NO 268
<211> LENGTH: 16
<212> TYPE: PRT
<213> ORGANISM: Homo sapiens

<400> SEQUENCE: 268

Cys Ala Arg Val Lys Gly Thr Gln Asn Tyr Tyr Gly Met Asp Val Trp
1               5                   10                  15

<210> SEQ ID NO 269
<211> LENGTH: 15
<212> TYPE: PRT
<213> ORGANISM: Homo sapiens

<400> SEQUENCE: 269

Cys His Tyr Tyr Asp Ser Thr Gly Tyr Tyr Val Ser Asp Phe Trp
1               5                   10                  15

<210> SEQ ID NO 270
<211> LENGTH: 16
<212> TYPE: PRT
<213> ORGANISM: Homo sapiens

<400> SEQUENCE: 270

Cys Ala Arg Gly Val Val Leu Ile Gln Thr Ile Leu Phe Asp Tyr Trp
1               5                   10                  15

<210> SEQ ID NO 271
<211> LENGTH: 17
<212> TYPE: PRT
<213> ORGANISM: Homo sapiens

<400> SEQUENCE: 271

Cys Ala Arg Thr Val Leu Asp Ser Gly Ala Tyr Ser Tyr Tyr Asp Ser
1               5                   10                  15

Arg

<210> SEQ ID NO 272
<211> LENGTH: 16
<212> TYPE: PRT
<213> ORGANISM: Homo sapiens

<400> SEQUENCE: 272

Cys Ala Arg Ser Arg Gly Ser Gln Asp Tyr Tyr Gly Met Asp Val Trp
1               5                   10                  15

<210> SEQ ID NO 273
<211> LENGTH: 22
<212> TYPE: PRT
<213> ORGANISM: Homo sapiens

<400> SEQUENCE: 273

Cys Ala Lys Leu Arg Asp Ser Ser Val Tyr Ser Ala Tyr Val Phe Arg
1               5                   10                  15

Val Ile Phe Asp Cys Trp
```

```
<210> SEQ ID NO 274
<211> LENGTH: 13
<212> TYPE: PRT
<213> ORGANISM: Homo sapiens

<400> SEQUENCE: 274

Cys Ala Thr Leu Thr Val Ala Ser Thr Tyr Asp Tyr Trp
1               5                   10

<210> SEQ ID NO 275
<211> LENGTH: 19
<212> TYPE: PRT
<213> ORGANISM: Homo sapiens

<400> SEQUENCE: 275

Cys Val Lys Asp Thr Val Ala Leu Leu Thr Ser Arg Gly Gly Cys Met
1               5                   10                  15

Asp Val Trp

<210> SEQ ID NO 276
<211> LENGTH: 12
<212> TYPE: PRT
<213> ORGANISM: Homo sapiens

<400> SEQUENCE: 276

Cys Ala His Ser Pro Pro His Gly Gly Asp Tyr Trp
1               5                   10

<210> SEQ ID NO 277
<211> LENGTH: 19
<212> TYPE: PRT
<213> ORGANISM: Homo sapiens

<400> SEQUENCE: 277

Cys Ala Lys Gly Leu Ser Gln Ala Leu Asn Tyr Tyr Gly Ser Gly Ser
1               5                   10                  15

Pro Phe Leu

<210> SEQ ID NO 278
<211> LENGTH: 19
<212> TYPE: PRT
<213> ORGANISM: Homo sapiens

<400> SEQUENCE: 278

Cys Ala Lys Asp Arg Gly Val Ser Ala Trp Tyr Pro Arg Asp Ala Phe
1               5                   10                  15

Asp Ile Trp

<210> SEQ ID NO 279
<211> LENGTH: 23
<212> TYPE: PRT
<213> ORGANISM: Homo sapiens

<400> SEQUENCE: 279

Cys Ala Arg Val Pro Leu Ile Glu Ala Gly Ile Thr Ile Phe Ala Lys
1               5                   10                  15

Ile Gly Ala Phe Asp Ile Trp
            20

<210> SEQ ID NO 280
```

```
<211> LENGTH: 15
<212> TYPE: PRT
<213> ORGANISM: Homo sapiens

<400> SEQUENCE: 280

Cys Ala Arg Gly Ser Pro Met Ile Lys Phe Tyr Phe Asp Tyr Trp
1               5                   10                  15

<210> SEQ ID NO 281
<211> LENGTH: 16
<212> TYPE: PRT
<213> ORGANISM: Homo sapiens

<400> SEQUENCE: 281

Cys Ala Arg Ala Thr Gly Ala Gly Arg Arg Asn Pro Leu Asp Tyr Trp
1               5                   10                  15

<210> SEQ ID NO 282
<211> LENGTH: 16
<212> TYPE: PRT
<213> ORGANISM: Homo sapiens

<400> SEQUENCE: 282

Cys Ala Arg Pro Tyr Arg Ser Tyr Ser Ser Pro Gln Asp Tyr Trp
1               5                   10                  15

<210> SEQ ID NO 283
<211> LENGTH: 15
<212> TYPE: PRT
<213> ORGANISM: Homo sapiens

<400> SEQUENCE: 283

Cys Ala Arg Tyr Tyr Tyr Ser Ser Gly Pro Lys Phe Asp Tyr Trp
1               5                   10                  15

<210> SEQ ID NO 284
<211> LENGTH: 17
<212> TYPE: PRT
<213> ORGANISM: Homo sapiens

<400> SEQUENCE: 284

Cys Ala Arg Asn Asn Arg Pro Leu Gly Ala Leu Phe Gly Met Asp Val
1               5                   10                  15

Trp

<210> SEQ ID NO 285
<211> LENGTH: 13
<212> TYPE: PRT
<213> ORGANISM: Homo sapiens

<400> SEQUENCE: 285

Cys Ala Arg Gly Gly Phe Asn Arg Leu Val Asp Pro Trp
1               5                   10

<210> SEQ ID NO 286
<211> LENGTH: 24
<212> TYPE: PRT
<213> ORGANISM: Homo sapiens

<400> SEQUENCE: 286

Cys Ala Arg Asn Thr Gly Ile Tyr Leu Gly Gly Ser Pro Gly Gly Thr
1               5                   10                  15

Arg Asn Asn Trp Phe Asp Pro Trp
            20
```

<210> SEQ ID NO 287
<211> LENGTH: 23
<212> TYPE: PRT
<213> ORGANISM: Homo sapiens

<400> SEQUENCE: 287

Cys Ala Arg Gln Gln Ala Lys Thr Leu Tyr Tyr Asp Ser Ser Gly Ser
1               5                   10                  15

Lys Ser Ala Phe Asp Ile Trp
            20

<210> SEQ ID NO 288
<211> LENGTH: 23
<212> TYPE: PRT
<213> ORGANISM: Homo sapiens

<400> SEQUENCE: 288

Cys Ala Arg Val Arg Gly Asn Ile Val Ala Thr Thr Ala Phe Tyr Tyr
1               5                   10                  15

Tyr Tyr Gly Leu Asp Ala Trp
            20

<210> SEQ ID NO 289
<211> LENGTH: 16
<212> TYPE: PRT
<213> ORGANISM: Homo sapiens

<400> SEQUENCE: 289

Cys Ala Lys Phe Asp Tyr Gly Glu Gly Ala Tyr His Phe Asp Phe Trp
1               5                   10                  15

<210> SEQ ID NO 290
<211> LENGTH: 17
<212> TYPE: PRT
<213> ORGANISM: Homo sapiens

<400> SEQUENCE: 290

Cys Ala Arg Asp Pro Ile Ala Leu Pro Gly Arg Gly Val Phe Asp Tyr
1               5                   10                  15

Trp

<210> SEQ ID NO 291
<211> LENGTH: 15
<212> TYPE: PRT
<213> ORGANISM: Homo sapiens

<400> SEQUENCE: 291

Cys Ser Ser Gly Tyr Tyr Phe Ala Gly Gly Glu Phe Asp Tyr Trp
1               5                   10                  15

<210> SEQ ID NO 292
<211> LENGTH: 22
<212> TYPE: PRT
<213> ORGANISM: Homo sapiens

<400> SEQUENCE: 292

Cys Thr Arg Asp Arg Gly Tyr Ser Asp His Thr Gly Leu Tyr Thr Arg
1               5                   10                  15

Phe Gly Phe Asp Ser Trp
            20

```
<210> SEQ ID NO 293
<211> LENGTH: 18
<212> TYPE: PRT
<213> ORGANISM: Homo sapiens

<400> SEQUENCE: 293

Cys Ala Arg Trp Arg Gly Gly Tyr Ser Gly Tyr Gly Asp Tyr Phe Asp
1               5                   10                  15

Ser Trp

<210> SEQ ID NO 294
<211> LENGTH: 25
<212> TYPE: PRT
<213> ORGANISM: Homo sapiens

<400> SEQUENCE: 294

Cys Ala Arg Asp Pro Gln Lys Pro Arg Gln His Leu Trp Pro Asn Pro
1               5                   10                  15

Tyr Tyr Tyr Ser Gly Met Asp Val Trp
            20                  25

<210> SEQ ID NO 295
<211> LENGTH: 14
<212> TYPE: PRT
<213> ORGANISM: Homo sapiens

<400> SEQUENCE: 295

Cys Ala Arg Gly Arg Ser Trp Arg Gly Tyr Leu Asp Tyr Trp
1               5                   10

<210> SEQ ID NO 296
<211> LENGTH: 21
<212> TYPE: PRT
<213> ORGANISM: Homo sapiens

<400> SEQUENCE: 296

Cys Ala Arg Asp Tyr Gly Asp Tyr Cys Gly Gly Asp Cys Pro Tyr Asp
1               5                   10                  15

Ala Phe Asp Ile Trp
            20

<210> SEQ ID NO 297
<211> LENGTH: 25
<212> TYPE: PRT
<213> ORGANISM: Homo sapiens

<400> SEQUENCE: 297

Cys Ala Arg Asp Lys Gly Glu Ser Asp Ile Asn Gly Trp Gln Thr Gly
1               5                   10                  15

Ala Phe Tyr Tyr Gly Met Asp Val Trp
            20                  25

<210> SEQ ID NO 298
<211> LENGTH: 20
<212> TYPE: PRT
<213> ORGANISM: Homo sapiens

<400> SEQUENCE: 298

Cys Ala Arg Ile Asp Ser Val Gly Trp Pro Ser Ser His Tyr Tyr Gly
1               5                   10                  15

Met Asp Val Trp
            20
```

```
<210> SEQ ID NO 299
<211> LENGTH: 19
<212> TYPE: PRT
<213> ORGANISM: Homo sapiens

<400> SEQUENCE: 299

Cys Ala Arg Asp Arg Ile Thr Gly Tyr Asp Ser Ser Gly His Ala Phe
1               5                   10                  15

Asp Ile Trp

<210> SEQ ID NO 300
<211> LENGTH: 22
<212> TYPE: PRT
<213> ORGANISM: Homo sapiens

<400> SEQUENCE: 300

Cys Ala Arg Gly Gly Lys Phe Cys Gly Ser Thr Ser Cys Phe Thr Glu
1               5                   10                  15

Gly Arg Leu Asp Tyr Trp
            20

<210> SEQ ID NO 301
<211> LENGTH: 22
<212> TYPE: PRT
<213> ORGANISM: Homo sapiens

<400> SEQUENCE: 301

Cys Ala Lys Asp Ser Gly Arg Tyr Ser Ser Leu Gly His Tyr Tyr Tyr
1               5                   10                  15

Tyr Gly Met Asp Val Trp
            20

<210> SEQ ID NO 302
<211> LENGTH: 20
<212> TYPE: PRT
<213> ORGANISM: Homo sapiens

<400> SEQUENCE: 302

Cys Ala Arg Gly Tyr Tyr Tyr Asp Thr Ser Gly Tyr Arg Pro Gly Ser
1               5                   10                  15

Phe Gln His Trp
            20

<210> SEQ ID NO 303
<211> LENGTH: 16
<212> TYPE: PRT
<213> ORGANISM: Homo sapiens

<400> SEQUENCE: 303

Cys Ala Arg Pro Leu Phe Tyr Gly Ala Gly Asp Ala Phe Asp Ile Trp
1               5                   10                  15

<210> SEQ ID NO 304
<211> LENGTH: 15
<212> TYPE: PRT
<213> ORGANISM: Homo sapiens

<400> SEQUENCE: 304

Cys Ala Asp Trp Val Val Gly Asn Tyr Asn Gly Leu Asp Val Trp
1               5                   10                  15

<210> SEQ ID NO 305
```

```
<211> LENGTH: 22
<212> TYPE: PRT
<213> ORGANISM: Homo sapiens

<400> SEQUENCE: 305

Cys Ala Arg Glu Gly Lys His Asp Phe Trp Arg Gly Tyr Phe Ser Pro
1               5                   10                  15

Leu Gly Met Asp Val Trp
            20

<210> SEQ ID NO 306
<211> LENGTH: 20
<212> TYPE: PRT
<213> ORGANISM: Homo sapiens

<400> SEQUENCE: 306

Cys Ala Thr Ala Arg Asn Ser Ser Asn Trp Tyr Glu Gly His Tyr Tyr
1               5                   10                  15

Leu Ala His Trp
            20

<210> SEQ ID NO 307
<211> LENGTH: 18
<212> TYPE: PRT
<213> ORGANISM: Homo sapiens

<400> SEQUENCE: 307

Cys Ala Asn Met Val Val Val Ala Thr Gln Pro Lys Asn Trp Phe Asp
1               5                   10                  15

Pro Trp

<210> SEQ ID NO 308
<211> LENGTH: 17
<212> TYPE: PRT
<213> ORGANISM: Homo sapiens

<400> SEQUENCE: 308

Cys Ala Ser Tyr Gly Ser Gly Met Gly Ser Glu Tyr Tyr Phe Gly His
1               5                   10                  15

Trp

<210> SEQ ID NO 309
<211> LENGTH: 17
<212> TYPE: PRT
<213> ORGANISM: Homo sapiens

<400> SEQUENCE: 309

Cys Gly Arg Val Gly Arg Glu Ala Phe Tyr Tyr Tyr Gly Met Asp Val
1               5                   10                  15

Trp

<210> SEQ ID NO 310
<211> LENGTH: 17
<212> TYPE: PRT
<213> ORGANISM: Homo sapiens

<400> SEQUENCE: 310

Cys Ala Arg Ala Ser Arg Arg Leu Thr Thr His Asn Tyr Phe Asp Gly
1               5                   10                  15

Trp
```

```
<210> SEQ ID NO 311
<211> LENGTH: 13
<212> TYPE: PRT
<213> ORGANISM: Homo sapiens

<400> SEQUENCE: 311

Cys Ala Arg Val Arg Gly Gly Arg Tyr Phe Asp Tyr Trp
1               5                   10

<210> SEQ ID NO 312
<211> LENGTH: 16
<212> TYPE: PRT
<213> ORGANISM: Homo sapiens

<400> SEQUENCE: 312

Cys Ala Ser Gly Ser Gly Tyr Asp Ser Tyr Tyr Asn Met Asp Val Trp
1               5                   10                  15

<210> SEQ ID NO 313
<211> LENGTH: 21
<212> TYPE: PRT
<213> ORGANISM: Homo sapiens

<400> SEQUENCE: 313

Cys Ala Arg Asp Ser Ser Thr Val Thr Gly Leu Met Thr Glu Tyr Asn
1               5                   10                  15

Trp Phe Asp Pro Trp
            20

<210> SEQ ID NO 314
<211> LENGTH: 17
<212> TYPE: PRT
<213> ORGANISM: Homo sapiens

<400> SEQUENCE: 314

Cys Ala Thr Glu Lys Gly Ser Gly Gly Asp Val Gly Lys Phe Asp Asn
1               5                   10                  15

Trp

<210> SEQ ID NO 315
<211> LENGTH: 13
<212> TYPE: PRT
<213> ORGANISM: Homo sapiens

<400> SEQUENCE: 315

Cys Ala Thr Gly Gln Gln Leu Tyr Ser Leu His Tyr Trp
1               5                   10

<210> SEQ ID NO 316
<211> LENGTH: 27
<212> TYPE: PRT
<213> ORGANISM: Homo sapiens

<400> SEQUENCE: 316

Cys Ala Arg Glu Gly Pro Gln Phe Tyr Tyr Asp Ser Gly Asp Tyr Tyr
1               5                   10                  15

Ser Ala His Ser Pro Gly Asp Phe Asp His Trp
            20                  25

<210> SEQ ID NO 317
<211> LENGTH: 11
<212> TYPE: PRT
<213> ORGANISM: Homo sapiens
```

```
<400> SEQUENCE: 317

Arg Ala Ser Gln Ser Val Arg Arg Ser Leu Ala
1               5                   10

<210> SEQ ID NO 318
<211> LENGTH: 11
<212> TYPE: PRT
<213> ORGANISM: Homo sapiens

<400> SEQUENCE: 318

Arg Ala Ser Gln Gly Ile Ser Asn Ser Leu Asn
1               5                   10

<210> SEQ ID NO 319
<211> LENGTH: 11
<212> TYPE: PRT
<213> ORGANISM: Homo sapiens

<400> SEQUENCE: 319

Arg Ala Ser Gln Ser Ile Ser Ile Trp Leu Ala
1               5                   10

<210> SEQ ID NO 320
<211> LENGTH: 11
<212> TYPE: PRT
<213> ORGANISM: Homo sapiens

<400> SEQUENCE: 320

Arg Ala Ser Gln Ser Ile Gly Asn Trp Leu Ala
1               5                   10

<210> SEQ ID NO 321
<211> LENGTH: 11
<212> TYPE: PRT
<213> ORGANISM: Homo sapiens

<400> SEQUENCE: 321

Gln Ala Ser Gln Asp Ile Ser Lys Tyr Leu Asn
1               5                   10

<210> SEQ ID NO 322
<211> LENGTH: 12
<212> TYPE: PRT
<213> ORGANISM: Homo sapiens

<400> SEQUENCE: 322

Arg Ala Ser Glu Ser Val Arg Ser Asn Tyr Leu Ala
1               5                   10

<210> SEQ ID NO 323
<211> LENGTH: 11
<212> TYPE: PRT
<213> ORGANISM: Homo sapiens

<400> SEQUENCE: 323

Arg Ala Ser Gln Ser Ile Ser Thr Tyr Leu Asn
1               5                   10

<210> SEQ ID NO 324
<211> LENGTH: 11
<212> TYPE: PRT
<213> ORGANISM: Homo sapiens

<400> SEQUENCE: 324
```

```
Gln Ala Ser Gln Asp Ile Lys Tyr Tyr Leu Asn
1               5                   10
```

<210> SEQ ID NO 325
<211> LENGTH: 16
<212> TYPE: PRT
<213> ORGANISM: Homo sapiens

<400> SEQUENCE: 325

```
Arg Ser Ser Lys Ser Leu Leu His Ser Asn Gly Tyr Asn Tyr Leu Asp
1               5                   10                  15
```

<210> SEQ ID NO 326
<211> LENGTH: 16
<212> TYPE: PRT
<213> ORGANISM: Homo sapiens

<400> SEQUENCE: 326

```
Arg Ser Ser Glu Ser Leu Val Asn Asn Asp Gly Asn Thr Tyr Leu Ser
1               5                   10                  15
```

<210> SEQ ID NO 327
<211> LENGTH: 11
<212> TYPE: PRT
<213> ORGANISM: Homo sapiens

<400> SEQUENCE: 327

```
Arg Ala Ser Gln Asn Ile Ser Asn Phe Leu Leu
1               5                   10
```

<210> SEQ ID NO 328
<211> LENGTH: 11
<212> TYPE: PRT
<213> ORGANISM: Homo sapiens

<400> SEQUENCE: 328

```
Arg Ala Ser Gln Ser Ile Asn Asn Tyr Leu Asn
1               5                   10
```

<210> SEQ ID NO 329
<211> LENGTH: 11
<212> TYPE: PRT
<213> ORGANISM: Homo sapiens

<400> SEQUENCE: 329

```
Arg Ala Ser Gln Ser Val Asp Arg Tyr Leu Ala
1               5                   10
```

<210> SEQ ID NO 330
<211> LENGTH: 11
<212> TYPE: PRT
<213> ORGANISM: Homo sapiens

<400> SEQUENCE: 330

```
Arg Ala Ser Gln Ser Ile Trp Thr Phe Leu Asn
1               5                   10
```

<210> SEQ ID NO 331
<211> LENGTH: 11
<212> TYPE: PRT
<213> ORGANISM: Homo sapiens

<400> SEQUENCE: 331

```
Arg Ala Ser Gln Ser Ile Ser Asn Trp Leu Ala
1               5                   10
```

```
<210> SEQ ID NO 332
<211> LENGTH: 11
<212> TYPE: PRT
<213> ORGANISM: Homo sapiens

<400> SEQUENCE: 332

Arg Ala Ser Gln Asp Ile Ser Asn Asp Leu Gly
1               5                   10

<210> SEQ ID NO 333
<211> LENGTH: 16
<212> TYPE: PRT
<213> ORGANISM: Homo sapiens

<400> SEQUENCE: 333

Arg Ser Ser Gln Ser Leu Val Tyr Ser Asp Gly Asn Thr Tyr Leu His
1               5                   10                  15

<210> SEQ ID NO 334
<211> LENGTH: 11
<212> TYPE: PRT
<213> ORGANISM: Homo sapiens

<400> SEQUENCE: 334

Arg Ala Ser Gln Gly Ile Gly Tyr Asp Leu Gly
1               5                   10

<210> SEQ ID NO 335
<211> LENGTH: 11
<212> TYPE: PRT
<213> ORGANISM: Homo sapiens

<400> SEQUENCE: 335

Arg Ala Ser Gln Ser Ile Ser Asn Tyr Leu Ser
1               5                   10

<210> SEQ ID NO 336
<211> LENGTH: 11
<212> TYPE: PRT
<213> ORGANISM: Homo sapiens

<400> SEQUENCE: 336

Arg Ala Ser Gln Ser Val Ser Ser Asn Leu Ala
1               5                   10

<210> SEQ ID NO 337
<211> LENGTH: 12
<212> TYPE: PRT
<213> ORGANISM: Homo sapiens

<400> SEQUENCE: 337

Arg Ala Ser Gln Ser Ile Ala Ser Ala Tyr Leu Ala
1               5                   10

<210> SEQ ID NO 338
<211> LENGTH: 16
<212> TYPE: PRT
<213> ORGANISM: Homo sapiens

<400> SEQUENCE: 338

Arg Ser Ser Gln Ser Leu Leu His Ser Asn Gly Tyr Asn Tyr Leu Asp
1               5                   10                  15
```

```
<210> SEQ ID NO 339
<211> LENGTH: 11
<212> TYPE: PRT
<213> ORGANISM: Homo sapiens

<400> SEQUENCE: 339

Gln Ala Ser His Asp Val Ser Asn Phe Leu Asn
1               5                   10

<210> SEQ ID NO 340
<211> LENGTH: 12
<212> TYPE: PRT
<213> ORGANISM: Homo sapiens

<400> SEQUENCE: 340

Arg Ala Ser Gln Ser Val Ser Ser Asn Tyr Ile Ala
1               5                   10

<210> SEQ ID NO 341
<211> LENGTH: 11
<212> TYPE: PRT
<213> ORGANISM: Homo sapiens

<400> SEQUENCE: 341

Arg Ala Ser Gln Ser Ile Arg Thr Tyr Leu Asn
1               5                   10

<210> SEQ ID NO 342
<211> LENGTH: 11
<212> TYPE: PRT
<213> ORGANISM: Homo sapiens

<400> SEQUENCE: 342

Arg Ala Ser Gln Thr Ile Ser Thr Tyr Leu Asn
1               5                   10

<210> SEQ ID NO 343
<211> LENGTH: 11
<212> TYPE: PRT
<213> ORGANISM: Homo sapiens

<400> SEQUENCE: 343

Arg Ala Ser Gln Gly Ile Ser Asn Tyr Leu Ala
1               5                   10

<210> SEQ ID NO 344
<211> LENGTH: 11
<212> TYPE: PRT
<213> ORGANISM: Homo sapiens

<400> SEQUENCE: 344

Arg Ala Ser Arg Ser Ile Ser Thr Tyr Leu Asn
1               5                   10

<210> SEQ ID NO 345
<211> LENGTH: 11
<212> TYPE: PRT
<213> ORGANISM: Homo sapiens

<400> SEQUENCE: 345

Arg Ala Ser Gln Ser Ile His Thr Tyr Leu Asn
1               5                   10

<210> SEQ ID NO 346
<211> LENGTH: 17
```

```
<212> TYPE: PRT
<213> ORGANISM: Homo sapiens

<400> SEQUENCE: 346

Lys Ser Ser Gln Ser Val Leu Tyr Ser Asn Asn Asn Asn Tyr Leu
1               5                   10                  15

Ala

<210> SEQ ID NO 347
<211> LENGTH: 11
<212> TYPE: PRT
<213> ORGANISM: Homo sapiens

<400> SEQUENCE: 347

Arg Ala Ser Gln Thr Ile Ser Thr Trp Leu Ala
1               5                   10

<210> SEQ ID NO 348
<211> LENGTH: 11
<212> TYPE: PRT
<213> ORGANISM: Homo sapiens

<400> SEQUENCE: 348

Arg Ala Ser Gln Ser Ile Ser Thr Trp Leu Ala
1               5                   10

<210> SEQ ID NO 349
<211> LENGTH: 11
<212> TYPE: PRT
<213> ORGANISM: Homo sapiens

<400> SEQUENCE: 349

Arg Ala Ser Gln Ser Ile Ser Asn Tyr Leu Asn
1               5                   10

<210> SEQ ID NO 350
<211> LENGTH: 11
<212> TYPE: PRT
<213> ORGANISM: Homo sapiens

<400> SEQUENCE: 350

Arg Ala Ser Leu Asn Ile Arg Asn Tyr Leu Asn
1               5                   10

<210> SEQ ID NO 351
<211> LENGTH: 11
<212> TYPE: PRT
<213> ORGANISM: Homo sapiens

<400> SEQUENCE: 351

Arg Ala Ser Gln Val Ile Gly Lys Tyr Leu Ala
1               5                   10

<210> SEQ ID NO 352
<211> LENGTH: 11
<212> TYPE: PRT
<213> ORGANISM: Homo sapiens

<400> SEQUENCE: 352

Arg Ala Ser Gln Gly Ile Arg Asn Asp Leu Gly
1               5                   10

<210> SEQ ID NO 353
<211> LENGTH: 11
```

```
<212> TYPE: PRT
<213> ORGANISM: Homo sapiens

<400> SEQUENCE: 353

Gln Ala Ser His Asp Ile Asn Lys Tyr Leu Asn
1               5                   10

<210> SEQ ID NO 354
<211> LENGTH: 11
<212> TYPE: PRT
<213> ORGANISM: Homo sapiens

<400> SEQUENCE: 354

Arg Ala Ser Gln Ser Ile Asn Asn Tyr Leu Asn
1               5                   10

<210> SEQ ID NO 355
<211> LENGTH: 11
<212> TYPE: PRT
<213> ORGANISM: Homo sapiens

<400> SEQUENCE: 355

Gln Ala Ser Gln Asp Ile Ser Asn Tyr Leu Asn
1               5                   10

<210> SEQ ID NO 356
<211> LENGTH: 11
<212> TYPE: PRT
<213> ORGANISM: Homo sapiens

<400> SEQUENCE: 356

Gln Ala Ser Gln Asp Ile Ser Phe Tyr Leu Asn
1               5                   10

<210> SEQ ID NO 357
<211> LENGTH: 11
<212> TYPE: PRT
<213> ORGANISM: Homo sapiens

<400> SEQUENCE: 357

Arg Ala Ser Gln Ser Ile Ser Ser Trp Leu Ala
1               5                   10

<210> SEQ ID NO 358
<211> LENGTH: 11
<212> TYPE: PRT
<213> ORGANISM: Homo sapiens

<400> SEQUENCE: 358

Arg Ala Ser Gln Asp Ile Ser Asn Tyr Leu Ala
1               5                   10

<210> SEQ ID NO 359
<211> LENGTH: 11
<212> TYPE: PRT
<213> ORGANISM: Homo sapiens

<400> SEQUENCE: 359

Arg Ala Ser Gln Ser Val Ser Thr Phe Leu Asn
1               5                   10

<210> SEQ ID NO 360
<211> LENGTH: 11
<212> TYPE: PRT
<213> ORGANISM: Homo sapiens
```

```
<400> SEQUENCE: 360

Arg Ala Ser Gln Asp Val Ser Pro Trp Leu Ala
1               5                   10

<210> SEQ ID NO 361
<211> LENGTH: 11
<212> TYPE: PRT
<213> ORGANISM: Homo sapiens

<400> SEQUENCE: 361

Arg Ala Ser Gln Gly Ile Ser Asp Trp Leu Ala
1               5                   10

<210> SEQ ID NO 362
<211> LENGTH: 11
<212> TYPE: PRT
<213> ORGANISM: Homo sapiens

<400> SEQUENCE: 362

Gln Ala Ser Gln Asp Ile Ser Asn Tyr Leu Asn
1               5                   10

<210> SEQ ID NO 363
<211> LENGTH: 16
<212> TYPE: PRT
<213> ORGANISM: Homo sapiens

<400> SEQUENCE: 363

Arg Ser Ser Gln Ser Val Val Tyr Ser Asp Gly Asn Ile Tyr Leu Asn
1               5                   10                  15

<210> SEQ ID NO 364
<211> LENGTH: 11
<212> TYPE: PRT
<213> ORGANISM: Homo sapiens

<400> SEQUENCE: 364

Arg Ala Ser Gln Asp Ile Ser Ser Trp Leu Ala
1               5                   10

<210> SEQ ID NO 365
<211> LENGTH: 11
<212> TYPE: PRT
<213> ORGANISM: Homo sapiens

<400> SEQUENCE: 365

Gln Ala Ser Gln Asp Ile Ser Asn Tyr Leu Asn
1               5                   10

<210> SEQ ID NO 366
<211> LENGTH: 12
<212> TYPE: PRT
<213> ORGANISM: Homo sapiens

<400> SEQUENCE: 366

Arg Ala Ser Gln Ser Val Ser Ser Leu Tyr Val Gly
1               5                   10

<210> SEQ ID NO 367
<211> LENGTH: 11
<212> TYPE: PRT
<213> ORGANISM: Homo sapiens

<400> SEQUENCE: 367
```

Arg Ala Ser Gln Ser Ile Ser Ser Phe Leu Asn
1               5                   10

<210> SEQ ID NO 368
<211> LENGTH: 12
<212> TYPE: PRT
<213> ORGANISM: Homo sapiens

<400> SEQUENCE: 368

Arg Ala Ser Gln Ser Val Ser Ser Tyr Leu Ala
1               5                   10

<210> SEQ ID NO 369
<211> LENGTH: 20
<212> TYPE: PRT
<213> ORGANISM: Homo sapiens

<400> SEQUENCE: 369

Arg Ala Ser Gln Ser Val Ser Ser Arg Ala Ser Gln Ser Val Ser Ser
1               5                   10                  15

Asn Tyr Leu Ala
            20

<210> SEQ ID NO 370
<211> LENGTH: 11
<212> TYPE: PRT
<213> ORGANISM: Homo sapiens

<400> SEQUENCE: 370

Arg Ala Ser Gln Thr Ile Arg Asn Tyr Leu Asn
1               5                   10

<210> SEQ ID NO 371
<211> LENGTH: 12
<212> TYPE: PRT
<213> ORGANISM: Homo sapiens

<400> SEQUENCE: 371

Arg Ala Ser Gln Ser Val Ser Asn Asn Asn Leu Ala
1               5                   10

<210> SEQ ID NO 372
<211> LENGTH: 11
<212> TYPE: PRT
<213> ORGANISM: Homo sapiens

<400> SEQUENCE: 372

Arg Ala Ser Gln Gly Ile Ser Asn Trp Leu Ala
1               5                   10

<210> SEQ ID NO 373
<211> LENGTH: 11
<212> TYPE: PRT
<213> ORGANISM: Homo sapiens

<400> SEQUENCE: 373

Arg Ala Ser Gln Gly Ile Gly Gly Ala Leu Ala
1               5                   10

<210> SEQ ID NO 374
<211> LENGTH: 12
<212> TYPE: PRT
<213> ORGANISM: Homo sapiens

```
<400> SEQUENCE: 374

Arg Ala Ser Gln Ser Val Ser Ser Asn Tyr Leu Ala
1               5                   10

<210> SEQ ID NO 375
<211> LENGTH: 11
<212> TYPE: PRT
<213> ORGANISM: Homo sapiens

<400> SEQUENCE: 375

Arg Ala Ser Gln Ser Ile Ser Arg His Leu Asn
1               5                   10

<210> SEQ ID NO 376
<211> LENGTH: 11
<212> TYPE: PRT
<213> ORGANISM: Homo sapiens

<400> SEQUENCE: 376

Arg Ala Ser Gln Ser Ile Ser Thr Tyr Leu Ala
1               5                   10

<210> SEQ ID NO 377
<211> LENGTH: 11
<212> TYPE: PRT
<213> ORGANISM: Homo sapiens

<400> SEQUENCE: 377

Arg Ala Ser Gln Gly Val Ser Asn Trp Val Ala
1               5                   10

<210> SEQ ID NO 378
<211> LENGTH: 11
<212> TYPE: PRT
<213> ORGANISM: Homo sapiens

<400> SEQUENCE: 378

Arg Ala Ser Gln Gly Ile Ser Thr Phe Leu Ala
1               5                   10

<210> SEQ ID NO 379
<211> LENGTH: 12
<212> TYPE: PRT
<213> ORGANISM: Homo sapiens

<400> SEQUENCE: 379

Arg Ala Ser Gln Ser Val Thr Ser Asn Tyr Leu Ala
1               5                   10

<210> SEQ ID NO 380
<211> LENGTH: 11
<212> TYPE: PRT
<213> ORGANISM: Homo sapiens

<400> SEQUENCE: 380

Arg Ala Ser Gln Gly Ile Ser Thr Trp Leu Ala
1               5                   10

<210> SEQ ID NO 381
<211> LENGTH: 16
<212> TYPE: PRT
<213> ORGANISM: Homo sapiens

<400> SEQUENCE: 381
```

```
Arg Ser Ser Gln Ser Leu Leu His Ser Asn Gly Tyr Asn Tyr Leu Asp
1               5                   10                  15
```

<210> SEQ ID NO 382
<211> LENGTH: 11
<212> TYPE: PRT
<213> ORGANISM: Homo sapiens

<400> SEQUENCE: 382

```
Arg Ala Ser Gln Ser Ile Ser Asn Tyr Leu Asn
1               5                   10
```

<210> SEQ ID NO 383
<211> LENGTH: 11
<212> TYPE: PRT
<213> ORGANISM: Homo sapiens

<400> SEQUENCE: 383

```
Arg Ala Ser Gln Ser Leu Asn Asn Trp Leu Ala
1               5                   10
```

<210> SEQ ID NO 384
<211> LENGTH: 12
<212> TYPE: PRT
<213> ORGANISM: Homo sapiens

<400> SEQUENCE: 384

```
Arg Ala Ser Gln Ser Val Ser Asn Asn Tyr Leu Ala
1               5                   10
```

<210> SEQ ID NO 385
<211> LENGTH: 11
<212> TYPE: PRT
<213> ORGANISM: Homo sapiens

<400> SEQUENCE: 385

```
Arg Ala Ser Gln Gly Ile Phe Asn Tyr Leu Ala
1               5                   10
```

<210> SEQ ID NO 386
<211> LENGTH: 11
<212> TYPE: PRT
<213> ORGANISM: Homo sapiens

<400> SEQUENCE: 386

```
Arg Ala Ser Gln Asn Ile Gly Asn Trp Leu Ala
1               5                   10
```

<210> SEQ ID NO 387
<211> LENGTH: 11
<212> TYPE: PRT
<213> ORGANISM: Homo sapiens

<400> SEQUENCE: 387

```
Arg Ala Ser Gln Asp Ile Ile Ser Trp Leu Ala
1               5                   10
```

<210> SEQ ID NO 388
<211> LENGTH: 11
<212> TYPE: PRT
<213> ORGANISM: Homo sapiens

<400> SEQUENCE: 388

```
Arg Ala Ser Gln Ser Ile Tyr Ile Trp Leu Ala
1               5                   10
```

<210> SEQ ID NO 389
<211> LENGTH: 11
<212> TYPE: PRT
<213> ORGANISM: Homo sapiens

<400> SEQUENCE: 389

Arg Ala Ser Gln Ser Ile Ser Arg Ser Leu Asn
1               5                   10

<210> SEQ ID NO 390
<211> LENGTH: 11
<212> TYPE: PRT
<213> ORGANISM: Homo sapiens

<400> SEQUENCE: 390

Arg Ala Ser Gln Pro Ile Ser Ser Phe Leu Asn
1               5                   10

<210> SEQ ID NO 391
<211> LENGTH: 11
<212> TYPE: PRT
<213> ORGANISM: Homo sapiens

<400> SEQUENCE: 391

Arg Ala Ser Gln Ser Ile Ser Ser Trp Leu Ala
1               5                   10

<210> SEQ ID NO 392
<211> LENGTH: 11
<212> TYPE: PRT
<213> ORGANISM: Homo sapiens

<400> SEQUENCE: 392

Arg Ala Ser Gln Ser Phe Asn Gly Tyr Leu Asn
1               5                   10

<210> SEQ ID NO 393
<211> LENGTH: 12
<212> TYPE: PRT
<213> ORGANISM: Homo sapiens

<400> SEQUENCE: 393

Arg Ala Ser Gln Thr Val Ile Ser Thr Tyr Leu Ala
1               5                   10

<210> SEQ ID NO 394
<211> LENGTH: 12
<212> TYPE: PRT
<213> ORGANISM: Homo sapiens

<400> SEQUENCE: 394

Arg Ala Ser Gln Ser Val Ser Ser Gly Ser Leu Asp
1               5                   10

<210> SEQ ID NO 395
<211> LENGTH: 11
<212> TYPE: PRT
<213> ORGANISM: Homo sapiens

<400> SEQUENCE: 395

Gln Ala Ser Gln Asp Ile Ser Asn Tyr Leu Asn
1               5                   10

```
<210> SEQ ID NO 396
<211> LENGTH: 11
<212> TYPE: PRT
<213> ORGANISM: Homo sapiens

<400> SEQUENCE: 396

Arg Ala Ser Gln Ser Ile Ser Ser Tyr Leu Asn
1               5                   10

<210> SEQ ID NO 397
<211> LENGTH: 11
<212> TYPE: PRT
<213> ORGANISM: Homo sapiens

<400> SEQUENCE: 397

Arg Ala Ser Gln Ser Ile Arg Ser Tyr Leu Asn
1               5                   10

<210> SEQ ID NO 398
<211> LENGTH: 11
<212> TYPE: PRT
<213> ORGANISM: Homo sapiens

<400> SEQUENCE: 398

Arg Ala Ser Gln Gly Ile Ser Ser Tyr Leu Val
1               5                   10

<210> SEQ ID NO 399
<211> LENGTH: 11
<212> TYPE: PRT
<213> ORGANISM: Homo sapiens

<400> SEQUENCE: 399

Arg Ala Ser Gln Ala Ile Ser Asn Tyr Leu Val
1               5                   10

<210> SEQ ID NO 400
<211> LENGTH: 12
<212> TYPE: PRT
<213> ORGANISM: Homo sapiens

<400> SEQUENCE: 400

Arg Ala Ser Gln Ser Val Ser Ser Thr Tyr Leu Ala
1               5                   10

<210> SEQ ID NO 401
<211> LENGTH: 11
<212> TYPE: PRT
<213> ORGANISM: Homo sapiens

<400> SEQUENCE: 401

Arg Ala Ser Gln Ser Ile Ser Asn His Leu Asn
1               5                   10

<210> SEQ ID NO 402
<211> LENGTH: 11
<212> TYPE: PRT
<213> ORGANISM: Homo sapiens

<400> SEQUENCE: 402

Arg Ala Ser Gln Ser Ile Ser Ser Tyr Leu Asn
1               5                   10

<210> SEQ ID NO 403
<211> LENGTH: 11
```

```
<212> TYPE: PRT
<213> ORGANISM: Homo sapiens

<400> SEQUENCE: 403

Arg Ala Asn Gln Ser Ile Asp Asp Tyr Leu His
1               5                   10

<210> SEQ ID NO 404
<211> LENGTH: 16
<212> TYPE: PRT
<213> ORGANISM: Homo sapiens

<400> SEQUENCE: 404

Arg Ser Ser Gln Ser Leu Val Tyr Ala Asp Gly Asp Thr His Leu Asn
1               5                   10                  15

<210> SEQ ID NO 405
<211> LENGTH: 11
<212> TYPE: PRT
<213> ORGANISM: Homo sapiens

<400> SEQUENCE: 405

Arg Ala Ser Gln Ser Ile Thr Asn Cys Leu Asn
1               5                   10

<210> SEQ ID NO 406
<211> LENGTH: 7
<212> TYPE: PRT
<213> ORGANISM: Homo sapiens

<400> SEQUENCE: 406

Asp Ala Ser Asn Arg Ala Thr
1               5

<210> SEQ ID NO 407
<211> LENGTH: 7
<212> TYPE: PRT
<213> ORGANISM: Homo sapiens

<400> SEQUENCE: 407

Gly Ala Ser Gly Leu Glu Ser
1               5

<210> SEQ ID NO 408
<211> LENGTH: 7
<212> TYPE: PRT
<213> ORGANISM: Homo sapiens

<400> SEQUENCE: 408

Lys Ala Ser Thr Leu Glu Ser
1               5

<210> SEQ ID NO 409
<211> LENGTH: 7
<212> TYPE: PRT
<213> ORGANISM: Homo sapiens

<400> SEQUENCE: 409

Asp Ala Ser Ser Leu Lys Ser
1               5

<210> SEQ ID NO 410
<211> LENGTH: 7
<212> TYPE: PRT
<213> ORGANISM: Homo sapiens
```

```
<400> SEQUENCE: 410

Asp Ala Ser Asn Leu Glu Thr
1               5

<210> SEQ ID NO 411
<211> LENGTH: 7
<212> TYPE: PRT
<213> ORGANISM: Homo sapiens

<400> SEQUENCE: 411

Gly Ala Ser Ser Arg Ala Thr
1               5

<210> SEQ ID NO 412
<211> LENGTH: 7
<212> TYPE: PRT
<213> ORGANISM: Homo sapiens

<400> SEQUENCE: 412

Ala Ala Ser Ser Leu Gln Ser
1               5

<210> SEQ ID NO 413
<211> LENGTH: 7
<212> TYPE: PRT
<213> ORGANISM: Homo sapiens

<400> SEQUENCE: 413

Asp Ala Ser Asn Leu Glu Thr
1               5

<210> SEQ ID NO 414
<211> LENGTH: 7
<212> TYPE: PRT
<213> ORGANISM: Homo sapiens

<400> SEQUENCE: 414

Leu Ala Ser Asn Arg Ala Ser
1               5

<210> SEQ ID NO 415
<211> LENGTH: 7
<212> TYPE: PRT
<213> ORGANISM: Homo sapiens

<400> SEQUENCE: 415

Lys Ile Ser Asn Arg Phe Ser
1               5

<210> SEQ ID NO 416
<211> LENGTH: 7
<212> TYPE: PRT
<213> ORGANISM: Homo sapiens

<400> SEQUENCE: 416

Ala Ala Ser Ser Leu Gln Ser
1               5

<210> SEQ ID NO 417
<211> LENGTH: 7
<212> TYPE: PRT
<213> ORGANISM: Homo sapiens

<400> SEQUENCE: 417
```

```
Ala Val Ser Ser Leu Gln Thr
1               5
```

<210> SEQ ID NO 418
<211> LENGTH: 7
<212> TYPE: PRT
<213> ORGANISM: Homo sapiens

<400> SEQUENCE: 418

```
Asp Ala Ser Asn Arg Asp Thr
1               5
```

<210> SEQ ID NO 419
<211> LENGTH: 7
<212> TYPE: PRT
<213> ORGANISM: Homo sapiens

<400> SEQUENCE: 419

```
Thr Ala Ser Ser Leu Gln Ser
1               5
```

<210> SEQ ID NO 420
<211> LENGTH: 7
<212> TYPE: PRT
<213> ORGANISM: Homo sapiens

<400> SEQUENCE: 420

```
Lys Ala Ser Asn Leu Glu Ser
1               5
```

<210> SEQ ID NO 421
<211> LENGTH: 7
<212> TYPE: PRT
<213> ORGANISM: Homo sapiens

<400> SEQUENCE: 421

```
Leu Ala Ser Ser Leu Gln Ser
1               5
```

<210> SEQ ID NO 422
<211> LENGTH: 7
<212> TYPE: PRT
<213> ORGANISM: Homo sapiens

<400> SEQUENCE: 422

```
Lys Val Ser Asn Arg Asp Ser
1               5
```

<210> SEQ ID NO 423
<211> LENGTH: 7
<212> TYPE: PRT
<213> ORGANISM: Homo sapiens

<400> SEQUENCE: 423

```
Ala Ala Ser Ser Leu Gln Ser
1               5
```

<210> SEQ ID NO 424
<211> LENGTH: 7
<212> TYPE: PRT
<213> ORGANISM: Homo sapiens

<400> SEQUENCE: 424

```
Ala Ala Ser Leu Leu Gln Thr
```

```
                        1               5

<210> SEQ ID NO 425
<211> LENGTH: 7
<212> TYPE: PRT
<213> ORGANISM: Homo sapiens

<400> SEQUENCE: 425

Gly Ala Ser Thr Arg Ala Thr
1               5

<210> SEQ ID NO 426
<211> LENGTH: 7
<212> TYPE: PRT
<213> ORGANISM: Homo sapiens

<400> SEQUENCE: 426

Gly Ala Ser Ser Arg Pro Thr
1               5

<210> SEQ ID NO 427
<211> LENGTH: 7
<212> TYPE: PRT
<213> ORGANISM: Homo sapiens

<400> SEQUENCE: 427

Leu Gly Ser Thr Arg Ala Ser
1               5

<210> SEQ ID NO 428
<211> LENGTH: 7
<212> TYPE: PRT
<213> ORGANISM: Homo sapiens

<400> SEQUENCE: 428

Asp Ala Ser Asn Leu Lys Thr
1               5

<210> SEQ ID NO 429
<211> LENGTH: 7
<212> TYPE: PRT
<213> ORGANISM: Homo sapiens

<400> SEQUENCE: 429

Gly Ala Ser Ser Arg Ala Thr
1               5

<210> SEQ ID NO 430
<211> LENGTH: 7
<212> TYPE: PRT
<213> ORGANISM: Homo sapiens

<400> SEQUENCE: 430

Ala Ala Ser Ser Leu Gln Ser
1               5

<210> SEQ ID NO 431
<211> LENGTH: 7
<212> TYPE: PRT
<213> ORGANISM: Homo sapiens

<400> SEQUENCE: 431

Ala Ala Ser Ser Leu Gln Ser
1               5
```

<210> SEQ ID NO 432
<211> LENGTH: 7
<212> TYPE: PRT
<213> ORGANISM: Homo sapiens

<400> SEQUENCE: 432

Gly Ala Ser Thr Leu Gln Ser
1               5

<210> SEQ ID NO 433
<211> LENGTH: 7
<212> TYPE: PRT
<213> ORGANISM: Homo sapiens

<400> SEQUENCE: 433

Ala Ala Ser Ser Leu Gln Ser
1               5

<210> SEQ ID NO 434
<211> LENGTH: 7
<212> TYPE: PRT
<213> ORGANISM: Homo sapiens

<400> SEQUENCE: 434

Thr Ala Ser Asn Leu Gln Ser
1               5

<210> SEQ ID NO 435
<211> LENGTH: 7
<212> TYPE: PRT
<213> ORGANISM: Homo sapiens

<400> SEQUENCE: 435

Trp Ala Ser Thr Arg Glu Ser
1               5

<210> SEQ ID NO 436
<211> LENGTH: 7
<212> TYPE: PRT
<213> ORGANISM: Homo sapiens

<400> SEQUENCE: 436

Asp Ala Ser Ser Leu Glu Ser
1               5

<210> SEQ ID NO 437
<211> LENGTH: 7
<212> TYPE: PRT
<213> ORGANISM: Homo sapiens

<400> SEQUENCE: 437

Asp Ala Ser Ser Leu Glu Ser
1               5

<210> SEQ ID NO 438
<211> LENGTH: 7
<212> TYPE: PRT
<213> ORGANISM: Homo sapiens

<400> SEQUENCE: 438

Gly Ala Ser Ser Leu Glu Ser
1               5

<210> SEQ ID NO 439

```
<211> LENGTH: 7
<212> TYPE: PRT
<213> ORGANISM: Homo sapiens

<400> SEQUENCE: 439

Ala Ala Ser Thr Leu Gln Ile
1               5

<210> SEQ ID NO 440
<211> LENGTH: 7
<212> TYPE: PRT
<213> ORGANISM: Homo sapiens

<400> SEQUENCE: 440

Ala Thr Ser Ile Leu Gln Ser
1               5

<210> SEQ ID NO 441
<211> LENGTH: 7
<212> TYPE: PRT
<213> ORGANISM: Homo sapiens

<400> SEQUENCE: 441

Ala Ala Ser Ser Leu Gln Ser
1               5

<210> SEQ ID NO 442
<211> LENGTH: 7
<212> TYPE: PRT
<213> ORGANISM: Homo sapiens

<400> SEQUENCE: 442

Asp Ala Ser Asn Leu Glu Thr
1               5

<210> SEQ ID NO 443
<211> LENGTH: 7
<212> TYPE: PRT
<213> ORGANISM: Homo sapiens

<400> SEQUENCE: 443

Ala Ala Ser Ser Leu His Ser
1               5

<210> SEQ ID NO 444
<211> LENGTH: 7
<212> TYPE: PRT
<213> ORGANISM: Homo sapiens

<400> SEQUENCE: 444

Asp Ala Ser His Leu Glu Thr
1               5

<210> SEQ ID NO 445
<211> LENGTH: 7
<212> TYPE: PRT
<213> ORGANISM: Homo sapiens

<400> SEQUENCE: 445

Asp Ala Ser Ile Leu Glu Thr
1               5

<210> SEQ ID NO 446
<211> LENGTH: 7
<212> TYPE: PRT
```

<213> ORGANISM: Homo sapiens

<400> SEQUENCE: 446

Lys Val Ser Ser Leu Glu Ser
1               5

<210> SEQ ID NO 447
<211> LENGTH: 7
<212> TYPE: PRT
<213> ORGANISM: Homo sapiens

<400> SEQUENCE: 447

Ala Ala Ser Ser Leu Leu Ser
1               5

<210> SEQ ID NO 448
<211> LENGTH: 7
<212> TYPE: PRT
<213> ORGANISM: Homo sapiens

<400> SEQUENCE: 448

Gly Val Ser Asn Leu Gln Ser
1               5

<210> SEQ ID NO 449
<211> LENGTH: 7
<212> TYPE: PRT
<213> ORGANISM: Homo sapiens

<400> SEQUENCE: 449

Lys Ala Ser Ser Leu Glu Ser
1               5

<210> SEQ ID NO 450
<211> LENGTH: 7
<212> TYPE: PRT
<213> ORGANISM: Homo sapiens

<400> SEQUENCE: 450

Lys Ala Ser Ser Leu Glu Ser
1               5

<210> SEQ ID NO 451
<211> LENGTH: 7
<212> TYPE: PRT
<213> ORGANISM: Homo sapiens

<400> SEQUENCE: 451

Asp Thr Ser Asn Leu Glu Thr
1               5

<210> SEQ ID NO 452
<211> LENGTH: 7
<212> TYPE: PRT
<213> ORGANISM: Homo sapiens

<400> SEQUENCE: 452

Gln Val Ser Asn Arg Asp Ser
1               5

<210> SEQ ID NO 453
<211> LENGTH: 7
<212> TYPE: PRT
<213> ORGANISM: Homo sapiens

```
<400> SEQUENCE: 453

Ala Ala Ser Ser Leu Gln Ser
1               5

<210> SEQ ID NO 454
<211> LENGTH: 7
<212> TYPE: PRT
<213> ORGANISM: Homo sapiens

<400> SEQUENCE: 454

Asp Ala Ser Asn Leu Glu Thr
1               5

<210> SEQ ID NO 455
<211> LENGTH: 7
<212> TYPE: PRT
<213> ORGANISM: Homo sapiens

<400> SEQUENCE: 455

Gly Thr Ser Ser Arg Ala Thr
1               5

<210> SEQ ID NO 456
<211> LENGTH: 7
<212> TYPE: PRT
<213> ORGANISM: Homo sapiens

<400> SEQUENCE: 456

Gly Ala Thr Thr Leu Gln Ser
1               5

<210> SEQ ID NO 457
<211> LENGTH: 7
<212> TYPE: PRT
<213> ORGANISM: Homo sapiens

<400> SEQUENCE: 457

Arg Ala Ser Ser Arg Ala Ala
1               5

<210> SEQ ID NO 458
<211> LENGTH: 7
<212> TYPE: PRT
<213> ORGANISM: Homo sapiens

<400> SEQUENCE: 458

Gly Ala Ser Thr Arg Ala Ala
1               5

<210> SEQ ID NO 459
<211> LENGTH: 7
<212> TYPE: PRT
<213> ORGANISM: Homo sapiens

<400> SEQUENCE: 459

Thr Ala Ser Ser Leu His Ser
1               5

<210> SEQ ID NO 460
<211> LENGTH: 7
<212> TYPE: PRT
<213> ORGANISM: Homo sapiens

<400> SEQUENCE: 460
```

```
Gly Ala Ser Ser Arg Ala Ala
1               5

<210> SEQ ID NO 461
<211> LENGTH: 7
<212> TYPE: PRT
<213> ORGANISM: Homo sapiens

<400> SEQUENCE: 461

Ala Ala Ser Ser Leu Gln Ser
1               5

<210> SEQ ID NO 462
<211> LENGTH: 7
<212> TYPE: PRT
<213> ORGANISM: Homo sapiens

<400> SEQUENCE: 462

Ala Ala Ser Thr Leu Gln Ser
1               5

<210> SEQ ID NO 463
<211> LENGTH: 7
<212> TYPE: PRT
<213> ORGANISM: Homo sapiens

<400> SEQUENCE: 463

Gly Ala Ser Ser Arg Ala Thr
1               5

<210> SEQ ID NO 464
<211> LENGTH: 7
<212> TYPE: PRT
<213> ORGANISM: Homo sapiens

<400> SEQUENCE: 464

Ala Ala Ser Ser Leu Gln Thr
1               5

<210> SEQ ID NO 465
<211> LENGTH: 7
<212> TYPE: PRT
<213> ORGANISM: Homo sapiens

<400> SEQUENCE: 465

Lys Ala Ser Ser Leu Glu Pro
1               5

<210> SEQ ID NO 466
<211> LENGTH: 7
<212> TYPE: PRT
<213> ORGANISM: Homo sapiens

<400> SEQUENCE: 466

Ala Ala Ser Ser Leu Gln Ser
1               5

<210> SEQ ID NO 467
<211> LENGTH: 7
<212> TYPE: PRT
<213> ORGANISM: Homo sapiens

<400> SEQUENCE: 467

Ala Ala Ser Ser Leu Gln Ser
1               5
```

<210> SEQ ID NO 468
<211> LENGTH: 7
<212> TYPE: PRT
<213> ORGANISM: Homo sapiens

<400> SEQUENCE: 468

Gly Ala Ser Asn Arg Ala Thr
1               5

<210> SEQ ID NO 469
<211> LENGTH: 7
<212> TYPE: PRT
<213> ORGANISM: Homo sapiens

<400> SEQUENCE: 469

Ala Ala Ser Thr Leu Gln His
1               5

<210> SEQ ID NO 470
<211> LENGTH: 7
<212> TYPE: PRT
<213> ORGANISM: Homo sapiens

<400> SEQUENCE: 470

Leu Gly Ser Asn Arg Ala Ser
1               5

<210> SEQ ID NO 471
<211> LENGTH: 7
<212> TYPE: PRT
<213> ORGANISM: Homo sapiens

<400> SEQUENCE: 471

Ala Ala Ser Arg Leu Gln Ser
1               5

<210> SEQ ID NO 472
<211> LENGTH: 7
<212> TYPE: PRT
<213> ORGANISM: Homo sapiens

<400> SEQUENCE: 472

Asp Ala Ser Ser Leu Gln Ser
1               5

<210> SEQ ID NO 473
<211> LENGTH: 7
<212> TYPE: PRT
<213> ORGANISM: Homo sapiens

<400> SEQUENCE: 473

Gly Ala Ser Ser Arg Ala Thr
1               5

<210> SEQ ID NO 474
<211> LENGTH: 7
<212> TYPE: PRT
<213> ORGANISM: Homo sapiens

<400> SEQUENCE: 474

Gly Ala Ser Thr Leu Arg Ser
1               5

```
<210> SEQ ID NO 475
<211> LENGTH: 7
<212> TYPE: PRT
<213> ORGANISM: Homo sapiens

<400> SEQUENCE: 475

Ser Ala Ser Ser Leu Gln Asn
1               5

<210> SEQ ID NO 476
<211> LENGTH: 7
<212> TYPE: PRT
<213> ORGANISM: Homo sapiens

<400> SEQUENCE: 476

Ala Ala Ser Ser Leu Gln Ser
1               5

<210> SEQ ID NO 477
<211> LENGTH: 7
<212> TYPE: PRT
<213> ORGANISM: Homo sapiens

<400> SEQUENCE: 477

Asp Ala Ser Ser Leu Glu Ser
1               5

<210> SEQ ID NO 478
<211> LENGTH: 7
<212> TYPE: PRT
<213> ORGANISM: Homo sapiens

<400> SEQUENCE: 478

Ala Ala Ser Thr Leu Gln Ser
1               5

<210> SEQ ID NO 479
<211> LENGTH: 7
<212> TYPE: PRT
<213> ORGANISM: Homo sapiens

<400> SEQUENCE: 479

Ala Ala Ser Ser Leu Gln Ser
1               5

<210> SEQ ID NO 480
<211> LENGTH: 7
<212> TYPE: PRT
<213> ORGANISM: Homo sapiens

<400> SEQUENCE: 480

His Ala Phe Ser Leu Glu Gly
1               5

<210> SEQ ID NO 481
<211> LENGTH: 7
<212> TYPE: PRT
<213> ORGANISM: Homo sapiens

<400> SEQUENCE: 481

Ala Ala Ser Thr Leu Gln Ser
1               5

<210> SEQ ID NO 482
<211> LENGTH: 7
```

<212> TYPE: PRT
<213> ORGANISM: Homo sapiens

<400> SEQUENCE: 482

Gly Ala Ser Ser Arg Ala Thr
1               5

<210> SEQ ID NO 483
<211> LENGTH: 7
<212> TYPE: PRT
<213> ORGANISM: Homo sapiens

<400> SEQUENCE: 483

Gly Ala Ser Asn Arg Ala Ser
1               5

<210> SEQ ID NO 484
<211> LENGTH: 7
<212> TYPE: PRT
<213> ORGANISM: Homo sapiens

<400> SEQUENCE: 484

Asp Ala Ser Asn Leu Glu Thr
1               5

<210> SEQ ID NO 485
<211> LENGTH: 7
<212> TYPE: PRT
<213> ORGANISM: Homo sapiens

<400> SEQUENCE: 485

Ala Ala Ser Ser Leu Gln Ser
1               5

<210> SEQ ID NO 486
<211> LENGTH: 7
<212> TYPE: PRT
<213> ORGANISM: Homo sapiens

<400> SEQUENCE: 486

Gly Ala Ser Ser Leu Gln Ser
1               5

<210> SEQ ID NO 487
<211> LENGTH: 7
<212> TYPE: PRT
<213> ORGANISM: Homo sapiens

<400> SEQUENCE: 487

Ala Ala Ser Thr Leu Glu Ser
1               5

<210> SEQ ID NO 488
<211> LENGTH: 7
<212> TYPE: PRT
<213> ORGANISM: Homo sapiens

<400> SEQUENCE: 488

Gly Ala Phe Ile Leu Glu Ser
1               5

<210> SEQ ID NO 489
<211> LENGTH: 7
<212> TYPE: PRT
<213> ORGANISM: Homo sapiens

```
<400> SEQUENCE: 489

Gly Ala Ser Asn Arg Ala Thr
1               5

<210> SEQ ID NO 490
<211> LENGTH: 7
<212> TYPE: PRT
<213> ORGANISM: Homo sapiens

<400> SEQUENCE: 490

Val Ala Ser Ser Leu Gln Gly
1               5

<210> SEQ ID NO 491
<211> LENGTH: 7
<212> TYPE: PRT
<213> ORGANISM: Homo sapiens

<400> SEQUENCE: 491

Ala Ala Ser Ser Leu Gln Ser
1               5

<210> SEQ ID NO 492
<211> LENGTH: 7
<212> TYPE: PRT
<213> ORGANISM: Homo sapiens

<400> SEQUENCE: 492

Asp Ala Ser Thr Leu His Ser
1               5

<210> SEQ ID NO 493
<211> LENGTH: 7
<212> TYPE: PRT
<213> ORGANISM: Homo sapiens

<400> SEQUENCE: 493

His Val Ser Asn Arg Asp Ala
1               5

<210> SEQ ID NO 494
<211> LENGTH: 7
<212> TYPE: PRT
<213> ORGANISM: Homo sapiens

<400> SEQUENCE: 494

Gly Ala Ser Thr Leu Gln Ser
1               5

<210> SEQ ID NO 495
<211> LENGTH: 11
<212> TYPE: PRT
<213> ORGANISM: Homo sapiens

<400> SEQUENCE: 495

Cys Leu Gln Arg Ser Asn Trp Pro Ile Thr Phe
1               5                   10

<210> SEQ ID NO 496
<211> LENGTH: 11
<212> TYPE: PRT
<213> ORGANISM: Homo sapiens

<400> SEQUENCE: 496
```

Cys Gln Gln Ser Tyr Arg Thr Leu Tyr Thr Phe
1               5                   10

<210> SEQ ID NO 497
<211> LENGTH: 12
<212> TYPE: PRT
<213> ORGANISM: Homo sapiens

<400> SEQUENCE: 497

Cys Gln Gln Tyr Asn Gly Tyr Ser Glu Val Thr Phe
1               5                   10

<210> SEQ ID NO 498
<211> LENGTH: 11
<212> TYPE: PRT
<213> ORGANISM: Homo sapiens

<400> SEQUENCE: 498

Cys Gln Gln Tyr Asp Thr Tyr Pro Ile Thr Phe
1               5                   10

<210> SEQ ID NO 499
<211> LENGTH: 11
<212> TYPE: PRT
<213> ORGANISM: Homo sapiens

<400> SEQUENCE: 499

Cys Gln Gln Tyr Asp Asn Leu Pro Pro Thr Phe
1               5                   10

<210> SEQ ID NO 500
<211> LENGTH: 11
<212> TYPE: PRT
<213> ORGANISM: Homo sapiens

<400> SEQUENCE: 500

Cys Gln Gln Tyr Gly Arg Ser Pro Leu Thr Phe
1               5                   10

<210> SEQ ID NO 501
<211> LENGTH: 11
<212> TYPE: PRT
<213> ORGANISM: Homo sapiens

<400> SEQUENCE: 501

Cys Gln Gln Ser Tyr Asn Thr Pro Ala Thr Phe
1               5                   10

<210> SEQ ID NO 502
<211> LENGTH: 11
<212> TYPE: PRT
<213> ORGANISM: Homo sapiens

<400> SEQUENCE: 502

Cys Gln Gln Tyr Glu Asn Val Pro Tyr Thr Phe
1               5                   10

<210> SEQ ID NO 503
<211> LENGTH: 11
<212> TYPE: PRT
<213> ORGANISM: Homo sapiens

<400> SEQUENCE: 503

Cys Met Gln Ala Leu Gln Ile Pro Arg Thr Phe

```
1               5                   10
```

<210> SEQ ID NO 504
<211> LENGTH: 11
<212> TYPE: PRT
<213> ORGANISM: Homo sapiens

<400> SEQUENCE: 504

```
Cys Met Gln Thr Thr His Ile Pro His Thr Phe
1               5                   10
```

<210> SEQ ID NO 505
<211> LENGTH: 11
<212> TYPE: PRT
<213> ORGANISM: Homo sapiens

<400> SEQUENCE: 505

```
Cys Gln Gln Thr Tyr Gly Asn Pro Leu Thr Phe
1               5                   10
```

<210> SEQ ID NO 506
<211> LENGTH: 11
<212> TYPE: PRT
<213> ORGANISM: Homo sapiens

<400> SEQUENCE: 506

```
Cys Gln Gln Ser Phe Arg Thr Pro His Thr Phe
1               5                   10
```

<210> SEQ ID NO 507
<211> LENGTH: 11
<212> TYPE: PRT
<213> ORGANISM: Homo sapiens

<400> SEQUENCE: 507

```
Cys Gln Gln Arg Ala Ile Trp Pro Pro Glu Phe
1               5                   10
```

<210> SEQ ID NO 508
<211> LENGTH: 11
<212> TYPE: PRT
<213> ORGANISM: Homo sapiens

<400> SEQUENCE: 508

```
Cys Gln Gln Ser Phe Thr Ser Trp Trp Thr Phe
1               5                   10
```

<210> SEQ ID NO 509
<211> LENGTH: 11
<212> TYPE: PRT
<213> ORGANISM: Homo sapiens

<400> SEQUENCE: 509

```
Cys Gln Gln Tyr Ser Asn Tyr Pro Ile Thr Phe
1               5                   10
```

<210> SEQ ID NO 510
<211> LENGTH: 10
<212> TYPE: PRT
<213> ORGANISM: Homo sapiens

<400> SEQUENCE: 510

```
Cys Leu Gln His Asn Ser Phe Leu Thr Phe
1               5                   10
```

<210> SEQ ID NO 511
<211> LENGTH: 11
<212> TYPE: PRT
<213> ORGANISM: Homo sapiens

<400> SEQUENCE: 511

Cys Met Gln Gly Thr His Trp Pro Pro Ala Phe
1               5                   10

<210> SEQ ID NO 512
<211> LENGTH: 11
<212> TYPE: PRT
<213> ORGANISM: Homo sapiens

<400> SEQUENCE: 512

Cys Leu Gln Leu His Thr Phe Pro Arg Thr Phe
1               5                   10

<210> SEQ ID NO 513
<211> LENGTH: 11
<212> TYPE: PRT
<213> ORGANISM: Homo sapiens

<400> SEQUENCE: 513

Cys Gln Gln Gly Tyr Ser Thr Pro Tyr Thr Phe
1               5                   10

<210> SEQ ID NO 514
<211> LENGTH: 12
<212> TYPE: PRT
<213> ORGANISM: Homo sapiens

<400> SEQUENCE: 514

Cys His Gln Tyr Asn Tyr Trp Pro Pro Leu Ala Phe
1               5                   10

<210> SEQ ID NO 515
<211> LENGTH: 11
<212> TYPE: PRT
<213> ORGANISM: Homo sapiens

<400> SEQUENCE: 515

Cys Gln Gln Tyr Gly Ile Ser Pro Arg Thr Phe
1               5                   10

<210> SEQ ID NO 516
<211> LENGTH: 11
<212> TYPE: PRT
<213> ORGANISM: Homo sapiens

<400> SEQUENCE: 516

Cys Met Gln Ala Leu Gln Thr Pro His Thr Phe
1               5                   10

<210> SEQ ID NO 517
<211> LENGTH: 11
<212> TYPE: PRT
<213> ORGANISM: Homo sapiens

<400> SEQUENCE: 517

Cys His Gln Tyr Asp Ser Leu Pro Phe Thr Phe
1               5                   10

<210> SEQ ID NO 518

```
<211> LENGTH: 12
<212> TYPE: PRT
<213> ORGANISM: Homo sapiens

<400> SEQUENCE: 518

Cys Gln Gln Phe Gly Tyr Ser Pro Arg Phe Thr Phe
1               5                   10

<210> SEQ ID NO 519
<211> LENGTH: 11
<212> TYPE: PRT
<213> ORGANISM: Homo sapiens

<400> SEQUENCE: 519

Cys Gln Gln Thr Tyr Ile Thr Pro Lys Ser Phe
1               5                   10

<210> SEQ ID NO 520
<211> LENGTH: 11
<212> TYPE: PRT
<213> ORGANISM: Homo sapiens

<400> SEQUENCE: 520

Cys Gln Gln Ser Tyr Arg Thr Pro Leu Thr Phe
1               5                   10

<210> SEQ ID NO 521
<211> LENGTH: 11
<212> TYPE: PRT
<213> ORGANISM: Homo sapiens

<400> SEQUENCE: 521

Cys Gln Lys Tyr Asp Ser Ala Pro Tyr Thr Phe
1               5                   10

<210> SEQ ID NO 522
<211> LENGTH: 11
<212> TYPE: PRT
<213> ORGANISM: Homo sapiens

<400> SEQUENCE: 522

Cys Gln Gln Thr Tyr Thr Ile Pro Leu Thr Phe
1               5                   10

<210> SEQ ID NO 523
<211> LENGTH: 11
<212> TYPE: PRT
<213> ORGANISM: Homo sapiens

<400> SEQUENCE: 523

Cys Gln Gln Ser Tyr Ser Thr Leu Arg Thr Phe
1               5                   10

<210> SEQ ID NO 524
<211> LENGTH: 11
<212> TYPE: PRT
<213> ORGANISM: Homo sapiens

<400> SEQUENCE: 524

Cys Gln Gln Tyr Tyr Lys Thr Pro Pro Thr Phe
1               5                   10

<210> SEQ ID NO 525
<211> LENGTH: 11
<212> TYPE: PRT
```

<213> ORGANISM: Homo sapiens

<400> SEQUENCE: 525

Cys Gln Gln Tyr Asn Ser Tyr Pro Leu Thr Phe
1               5                   10

<210> SEQ ID NO 526
<211> LENGTH: 10
<212> TYPE: PRT
<213> ORGANISM: Homo sapiens

<400> SEQUENCE: 526

Cys Gln Gln Tyr Asn Phe Tyr Gly Thr Phe
1               5                   10

<210> SEQ ID NO 527
<211> LENGTH: 11
<212> TYPE: PRT
<213> ORGANISM: Homo sapiens

<400> SEQUENCE: 527

Cys Gln Gln Ser Tyr Ser Ile Pro Arg Thr Phe
1               5                   10

<210> SEQ ID NO 528
<211> LENGTH: 13
<212> TYPE: PRT
<213> ORGANISM: Homo sapiens

<400> SEQUENCE: 528

Val Cys Gln Gln Ser Tyr Ser Met Ser Pro Tyr Thr Phe
1               5                   10

<210> SEQ ID NO 529
<211> LENGTH: 11
<212> TYPE: PRT
<213> ORGANISM: Homo sapiens

<400> SEQUENCE: 529

Cys Gln Gln Tyr Asn Ser Phe Pro Leu Thr Phe
1               5                   10

<210> SEQ ID NO 530
<211> LENGTH: 11
<212> TYPE: PRT
<213> ORGANISM: Homo sapiens

<400> SEQUENCE: 530

Cys Leu Gln Gln Asn Asn Tyr Pro Trp Thr Phe
1               5                   10

<210> SEQ ID NO 531
<211> LENGTH: 11
<212> TYPE: PRT
<213> ORGANISM: Homo sapiens

<400> SEQUENCE: 531

Cys Gln Gln Tyr Asp Asn Phe Pro Tyr Thr Phe
1               5                   10

<210> SEQ ID NO 532
<211> LENGTH: 11
<212> TYPE: PRT
<213> ORGANISM: Homo sapiens

```
<400> SEQUENCE: 532

Cys Gln Gln Thr Tyr Ile Ser Thr Arg Thr Phe
1               5                   10

<210> SEQ ID NO 533
<211> LENGTH: 10
<212> TYPE: PRT
<213> ORGANISM: Homo sapiens

<400> SEQUENCE: 533

Cys Gln Gln Tyr Asp Asn Leu Pro Leu Phe
1               5                   10

<210> SEQ ID NO 534
<211> LENGTH: 10
<212> TYPE: PRT
<213> ORGANISM: Homo sapiens

<400> SEQUENCE: 534

Cys Gln Gln Tyr Asp Asn Leu Ile Thr Phe
1               5                   10

<210> SEQ ID NO 535
<211> LENGTH: 11
<212> TYPE: PRT
<213> ORGANISM: Homo sapiens

<400> SEQUENCE: 535

Cys Gln Gln Tyr Glu Ser Asp Ile Phe Thr Phe
1               5                   10

<210> SEQ ID NO 536
<211> LENGTH: 11
<212> TYPE: PRT
<213> ORGANISM: Homo sapiens

<400> SEQUENCE: 536

Cys Gln Gln Tyr Gly Arg Tyr Pro Leu Thr Phe
1               5                   10

<210> SEQ ID NO 537
<211> LENGTH: 11
<212> TYPE: PRT
<213> ORGANISM: Homo sapiens

<400> SEQUENCE: 537

Cys Gln Gln Ser His Arg Thr Pro Tyr Thr Phe
1               5                   10

<210> SEQ ID NO 538
<211> LENGTH: 10
<212> TYPE: PRT
<213> ORGANISM: Homo sapiens

<400> SEQUENCE: 538

Cys Gln Gln Tyr Gln Thr Tyr Ser Thr Phe
1               5                   10

<210> SEQ ID NO 539
<211> LENGTH: 11
<212> TYPE: PRT
<213> ORGANISM: Homo sapiens

<400> SEQUENCE: 539
```

Cys Gln Gln Tyr Glu Ser Asp Ser Trp Thr Phe
1               5                   10

<210> SEQ ID NO 540
<211> LENGTH: 11
<212> TYPE: PRT
<213> ORGANISM: Homo sapiens

<400> SEQUENCE: 540

Cys Gln Gln Tyr Asp Asn Leu Pro Phe Thr Phe
1               5                   10

<210> SEQ ID NO 541
<211> LENGTH: 11
<212> TYPE: PRT
<213> ORGANISM: Homo sapiens

<400> SEQUENCE: 541

Cys Met Gln Gly Thr His Trp Pro Tyr Ser Phe
1               5                   10

<210> SEQ ID NO 542
<211> LENGTH: 11
<212> TYPE: PRT
<213> ORGANISM: Homo sapiens

<400> SEQUENCE: 542

Cys Gln Gln Ala Tyr Ser Phe Pro Trp Thr Phe
1               5                   10

<210> SEQ ID NO 543
<211> LENGTH: 10
<212> TYPE: PRT
<213> ORGANISM: Homo sapiens

<400> SEQUENCE: 543

Cys Gln Gln Tyr Asp Asn Leu Pro Thr Phe
1               5                   10

<210> SEQ ID NO 544
<211> LENGTH: 11
<212> TYPE: PRT
<213> ORGANISM: Homo sapiens

<400> SEQUENCE: 544

Cys Gln Gln Tyr Gly Thr Ser Pro Trp Thr Phe
1               5                   10

<210> SEQ ID NO 545
<211> LENGTH: 11
<212> TYPE: PRT
<213> ORGANISM: Homo sapiens

<400> SEQUENCE: 545

Cys His Gln Ser Tyr Ser Leu Pro Phe Thr Phe
1               5                   10

<210> SEQ ID NO 546
<211> LENGTH: 11
<212> TYPE: PRT
<213> ORGANISM: Homo sapiens

<400> SEQUENCE: 546

Cys Gln Gln Tyr Val Ala Ser Pro Phe Thr Phe
1               5                   10

<210> SEQ ID NO 547
<211> LENGTH: 11
<212> TYPE: PRT
<213> ORGANISM: Homo sapiens

<400> SEQUENCE: 547

Cys His Gln Tyr Gly Thr Ser Pro Arg Thr Phe
1               5                   10

<210> SEQ ID NO 548
<211> LENGTH: 11
<212> TYPE: PRT
<213> ORGANISM: Homo sapiens

<400> SEQUENCE: 548

Cys Gln Gln Ser Tyr Ile Thr Pro Tyr Thr Phe
1               5                   10

<210> SEQ ID NO 549
<211> LENGTH: 11
<212> TYPE: PRT
<213> ORGANISM: Homo sapiens

<400> SEQUENCE: 549

Cys Gln Gln Tyr Gly Ser Ser Pro Tyr Thr Phe
1               5                   10

<210> SEQ ID NO 550
<211> LENGTH: 11
<212> TYPE: PRT
<213> ORGANISM: Homo sapiens

<400> SEQUENCE: 550

Cys Gln Gln Ala Asn Ser Phe Pro Phe Thr Phe
1               5                   10

<210> SEQ ID NO 551
<211> LENGTH: 11
<212> TYPE: PRT
<213> ORGANISM: Homo sapiens

<400> SEQUENCE: 551

Cys Gln Gln Leu Asp Thr Tyr Pro Leu Thr Phe
1               5                   10

<210> SEQ ID NO 552
<211> LENGTH: 11
<212> TYPE: PRT
<213> ORGANISM: Homo sapiens

<400> SEQUENCE: 552

Cys Gln Gln Tyr Ala Ser Ser Pro Tyr Thr Phe
1               5                   10

<210> SEQ ID NO 553
<211> LENGTH: 11
<212> TYPE: PRT
<213> ORGANISM: Homo sapiens

<400> SEQUENCE: 553

Cys Gln His Ser Ser Lys Thr Pro Phe Thr Phe
1               5                   10

```
<210> SEQ ID NO 554
<211> LENGTH: 10
<212> TYPE: PRT
<213> ORGANISM: Homo sapiens

<400> SEQUENCE: 554

Cys Gln Gln Tyr Ser Ser Tyr Leu Ser Phe
1               5                   10

<210> SEQ ID NO 555
<211> LENGTH: 11
<212> TYPE: PRT
<213> ORGANISM: Homo sapiens

<400> SEQUENCE: 555

Cys Gln Gln Ala Asn Gly Phe Leu Trp Thr Phe
1               5                   10

<210> SEQ ID NO 556
<211> LENGTH: 11
<212> TYPE: PRT
<213> ORGANISM: Homo sapiens

<400> SEQUENCE: 556

Cys Gln Gln Ala His Ser Phe Pro Val Thr Phe
1               5                   10

<210> SEQ ID NO 557
<211> LENGTH: 11
<212> TYPE: PRT
<213> ORGANISM: Homo sapiens

<400> SEQUENCE: 557

Cys Gln Gln Tyr Gly Ser Ser Pro Leu Thr Phe
1               5                   10

<210> SEQ ID NO 558
<211> LENGTH: 11
<212> TYPE: PRT
<213> ORGANISM: Homo sapiens

<400> SEQUENCE: 558

Cys Gln Gln Ala Asn Ser Phe Pro Arg Thr Phe
1               5                   10

<210> SEQ ID NO 559
<211> LENGTH: 10
<212> TYPE: PRT
<213> ORGANISM: Homo sapiens

<400> SEQUENCE: 559

Cys Met Gln Ser Leu Gln Thr Val Thr Phe
1               5                   10

<210> SEQ ID NO 560
<211> LENGTH: 12
<212> TYPE: PRT
<213> ORGANISM: Homo sapiens

<400> SEQUENCE: 560

Cys Gln His Ser Tyr Glu Thr Pro Pro Tyr Thr Phe
1               5                   10

<210> SEQ ID NO 561
<211> LENGTH: 11
```

<212> TYPE: PRT
<213> ORGANISM: Homo sapiens

<400> SEQUENCE: 561

Cys Gln Gln Tyr Asn Phe Tyr Pro Trp Thr Phe
1               5                   10

<210> SEQ ID NO 562
<211> LENGTH: 11
<212> TYPE: PRT
<213> ORGANISM: Homo sapiens

<400> SEQUENCE: 562

Cys Gln Gln Tyr Gly Gly Ser Pro Gln Thr Phe
1               5                   10

<210> SEQ ID NO 563
<211> LENGTH: 11
<212> TYPE: PRT
<213> ORGANISM: Homo sapiens

<400> SEQUENCE: 563

Cys Gln Lys Tyr Asn Ser Ala Pro Leu Thr Phe
1               5                   10

<210> SEQ ID NO 564
<211> LENGTH: 11
<212> TYPE: PRT
<213> ORGANISM: Homo sapiens

<400> SEQUENCE: 564

Cys Gln Gln Ala Asn Ser Phe Pro Val Thr Phe
1               5                   10

<210> SEQ ID NO 565
<211> LENGTH: 12
<212> TYPE: PRT
<213> ORGANISM: Homo sapiens

<400> SEQUENCE: 565

Cys Gln Gln Thr His Ser Phe Pro Pro Trp Thr Phe
1               5                   10

<210> SEQ ID NO 566
<211> LENGTH: 11
<212> TYPE: PRT
<213> ORGANISM: Homo sapiens

<400> SEQUENCE: 566

Cys Gln Gln Tyr His His Tyr Ser Pro Thr Phe
1               5                   10

<210> SEQ ID NO 567
<211> LENGTH: 11
<212> TYPE: PRT
<213> ORGANISM: Homo sapiens

<400> SEQUENCE: 567

Cys Gln Gln Ser Tyr Ser Thr Leu Arg Thr Phe
1               5                   10

<210> SEQ ID NO 568
<211> LENGTH: 11
<212> TYPE: PRT
<213> ORGANISM: Homo sapiens

<400> SEQUENCE: 568

Cys Gln Gln Gly Tyr Ser Thr Pro Pro Thr Phe
1               5                   10

<210> SEQ ID NO 569
<211> LENGTH: 11
<212> TYPE: PRT
<213> ORGANISM: Homo sapiens

<400> SEQUENCE: 569

Cys Gln Gln Tyr Asp Ser Tyr Pro Tyr Thr Phe
1               5                   10

<210> SEQ ID NO 570
<211> LENGTH: 11
<212> TYPE: PRT
<213> ORGANISM: Homo sapiens

<400> SEQUENCE: 570

Cys Gln Gln Ser Tyr Ser Thr Pro Arg Thr Phe
1               5                   10

<210> SEQ ID NO 571
<211> LENGTH: 10
<212> TYPE: PRT
<213> ORGANISM: Homo sapiens

<400> SEQUENCE: 571

Cys Gln Gln Tyr Ser Asp Ser Leu Thr Phe
1               5                   10

<210> SEQ ID NO 572
<211> LENGTH: 11
<212> TYPE: PRT
<213> ORGANISM: Homo sapiens

<400> SEQUENCE: 572

Cys His Gln Tyr Gly Gly Ala Gln Gly Thr Phe
1               5                   10

<210> SEQ ID NO 573
<211> LENGTH: 12
<212> TYPE: PRT
<213> ORGANISM: Homo sapiens

<400> SEQUENCE: 573

Cys Gln Gln Tyr Asp Thr Leu Pro Pro Ile Thr Phe
1               5                   10

<210> SEQ ID NO 574
<211> LENGTH: 11
<212> TYPE: PRT
<213> ORGANISM: Homo sapiens

<400> SEQUENCE: 574

Cys Gln Gln Ser His Ser Ser Pro Trp Thr Phe
1               5                   10

<210> SEQ ID NO 575
<211> LENGTH: 11
<212> TYPE: PRT
<213> ORGANISM: Homo sapiens

<400> SEQUENCE: 575

Cys Gln Gln Ser Tyr Leu Ala Pro Trp Thr Phe
1               5                   10

<210> SEQ ID NO 576
<211> LENGTH: 11
<212> TYPE: PRT
<213> ORGANISM: Homo sapiens

<400> SEQUENCE: 576

Cys Gln Gln Phe Asn Asn Tyr Pro Tyr Thr Phe
1               5                   10

<210> SEQ ID NO 577
<211> LENGTH: 11
<212> TYPE: PRT
<213> ORGANISM: Homo sapiens

<400> SEQUENCE: 577

Cys Gln Gln Tyr His Thr Tyr Pro Phe Thr Phe
1               5                   10

<210> SEQ ID NO 578
<211> LENGTH: 12
<212> TYPE: PRT
<213> ORGANISM: Homo sapiens

<400> SEQUENCE: 578

Cys Gln Lys Tyr Gly Arg Ser Pro Thr Trp Thr Phe
1               5                   10

<210> SEQ ID NO 579
<211> LENGTH: 11
<212> TYPE: PRT
<213> ORGANISM: Homo sapiens

<400> SEQUENCE: 579

Cys Gln Gln Gly Phe Thr Thr Pro Ile Thr Phe
1               5                   10

<210> SEQ ID NO 580
<211> LENGTH: 11
<212> TYPE: PRT
<213> ORGANISM: Homo sapiens

<400> SEQUENCE: 580

Cys Gln Gln Ser Tyr Ser Thr Pro Tyr Thr Phe
1               5                   10

<210> SEQ ID NO 581
<211> LENGTH: 12
<212> TYPE: PRT
<213> ORGANISM: Homo sapiens

<400> SEQUENCE: 581

Cys Gln Gln Ser Tyr Thr Ile Pro Leu Trp Thr Phe
1               5                   10

<210> SEQ ID NO 582
<211> LENGTH: 11
<212> TYPE: PRT
<213> ORGANISM: Homo sapiens

<400> SEQUENCE: 582

Cys Met Gln Gly Thr His Trp Pro Pro Thr Phe

```
                        1               5                      10
```

<210> SEQ ID NO 583
<211> LENGTH: 11
<212> TYPE: PRT
<213> ORGANISM: Homo sapiens

<400> SEQUENCE: 583

Cys Gln Gln Ser Asp Ser Thr Pro Tyr Thr Phe
1               5                   10

<210> SEQ ID NO 584
<211> LENGTH: 263
<212> TYPE: PRT
<213> ORGANISM: Vaccinia virus

<400> SEQUENCE: 584

Met Lys Val Glu Ser Val Thr Phe Leu Thr Leu Leu Gly Ile Gly Cys
1               5                   10                  15

Val Leu Ser Cys Cys Thr Ile Pro Ser Arg Pro Ile Asn Met Lys Phe
                20                  25                  30

Lys Asn Ser Val Glu Thr Asp Ala Asn Ala Asn Tyr Asn Ile Gly Asp
            35                  40                  45

Thr Ile Glu Tyr Leu Cys Leu Pro Gly Tyr Arg Lys Gln Lys Met Gly
    50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly Gln
                85                  90                  95

Leu Asp Ile Gly Gly Val Asp Phe Gly Ser Ser Ile Thr Tyr Ser Cys
            100                 105                 110

Asn Ser Gly Tyr His Leu Ile Gly Glu Ser Lys Ser Tyr Cys Glu Leu
        115                 120                 125

Gly Ser Thr Gly Ser Met Val Trp Asn Pro Glu Ala Pro Ile Cys Glu
    130                 135                 140

Ser Val Lys Cys Gln Ser Pro Pro Ser Ile Ser Asn Gly Arg His Asn
145                 150                 155                 160

Gly Tyr Glu Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asp Pro Pro Thr Cys Gln Ile Val Lys Cys Pro His
        195                 200                 205

Pro Thr Ile Ser Asn Gly Tyr Leu Ser Ser Gly Phe Lys Arg Ser Tyr
    210                 215                 220

Ser Tyr Asn Asp Asn Val Asp Phe Lys Cys Lys Tyr Gly Tyr Lys Leu
225                 230                 235                 240

Ser Gly Ser Ser Ser Ser Thr Cys Ser Pro Gly Asn Thr Trp Lys Pro
                245                 250                 255

Glu Leu Pro Lys Cys Val Arg
            260

<210> SEQ ID NO 585
<211> LENGTH: 265
<212> TYPE: PRT
<213> ORGANISM: Camelpox virus

<400> SEQUENCE: 585

```
Met Lys Val Glu Ser Val Thr Phe Leu Thr Leu Leu Gly Ile Val Cys
1               5                   10                  15

Val Leu Ser Cys Cys Thr Ile Pro Ser Arg Pro Ile Asn Met Lys Phe
            20                  25                  30

Lys Asn Ser Val Glu Thr Tyr Ala Asn Thr Asn Thr Asn Tyr Asn Ile
        35                  40                  45

Gly Asp Thr Ile Glu Tyr Leu Cys Leu Pro Gly Tyr Arg Lys Gln Lys
    50                  55                  60

Met Gly Pro Ile Tyr Ala Lys Cys Thr Gly Thr Gly Trp Thr Leu Phe
65                  70                  75                  80

Asn Gln Cys Ile Lys Arg Arg Cys Pro Ser Pro Arg Asp Ile Asp Asn
                85                  90                  95

Gly Gln Leu Asp Ile Gly Gly Val Asp Phe Gly Ser Ser Ile Thr Tyr
            100                 105                 110

Ser Cys Asn Ser Gly Tyr His Leu Ile Gly Glu Ser Lys Ser Tyr Cys
            115                 120                 125

Glu Leu Gly Ser Thr Gly Ser Met Val Trp Asn Pro Glu Ala Pro Ile
        130                 135                 140

Cys Glu Ser Val Lys Cys Gln Ser Pro Pro Ser Ile Ser Asn Gly Arg
145                 150                 155                 160

His Asn Gly Tyr Asp Asn Phe Tyr Thr Asp Gly Ser Val Val Thr Tyr
                165                 170                 175

Ser Cys Asn Ser Gly Tyr Ser Leu Ile Gly Asn Ser Gly Val Leu Cys
            180                 185                 190

Ser Gly Gly Glu Trp Ser Asp Pro Pro Thr Cys Gln Ile Val Lys Cys
        195                 200                 205

Pro His Pro Thr Ile Ser Asn Gly Tyr Leu Ser Ser Gly Phe Lys Arg
    210                 215                 220

Ser Tyr Ser Tyr Asn Asp Asn Val Asp Phe Thr Cys Lys Tyr Gly Tyr
225                 230                 235                 240

Lys Leu Ser Gly Ser Ser Ser Ser Thr Cys Ser Pro Gly Asn Thr Trp
                245                 250                 255

Gln Pro Glu Leu Pro Lys Cys Val Arg
            260                 265

<210> SEQ ID NO 586
<211> LENGTH: 263
<212> TYPE: PRT
<213> ORGANISM: Variola virus

<400> SEQUENCE: 586

Met Lys Val Glu Arg Val Thr Phe Leu Thr Leu Leu Gly Ile Gly Cys
1               5                   10                  15

Val Leu Ser Cys Cys Thr Ile Pro Ser Arg Pro Ile Asn Met Lys Phe
            20                  25                  30

Lys Asn Ser Val Glu Thr Asp Ala Asn Ala Asn Tyr Asn Ile Gly Asp
        35                  40                  45

Thr Ile Glu Tyr Leu Cys Leu Pro Gly Tyr Arg Lys Gln Lys Met Gly
    50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly His
                85                  90                  95

Leu Asp Ile Gly Gly Val Asp Phe Gly Ser Ser Ile Thr Tyr Ser Cys
```

```
            100                 105                 110
Asn Ser Gly Tyr Tyr Leu Ile Gly Glu Tyr Lys Ser Tyr Cys Lys Leu
            115                 120                 125
Gly Ser Thr Gly Ser Met Val Trp Asn Pro Lys Ala Pro Ile Cys Glu
            130                 135                 140
Ser Val Lys Cys Gln Leu Pro Pro Ser Ile Ser Asn Gly Arg His Asn
145                 150                 155                 160
Gly Tyr Asn Asp Phe Tyr Thr Asp Gly Ser Val Val Thr Tyr Ser Cys
                    165                 170                 175
Asn Ser Gly Tyr Ser Leu Ile Gly Asn Ser Gly Val Leu Cys Ser Gly
            180                 185                 190
Gly Glu Trp Ser Asn Pro Pro Thr Cys Gln Ile Val Lys Cys Pro His
            195                 200                 205
Pro Thr Ile Leu Asn Gly Tyr Leu Ser Ser Gly Phe Lys Arg Ser Tyr
            210                 215                 220
Ser Tyr Asn Asp Asn Val Asp Phe Thr Cys Lys Tyr Gly Tyr Lys Leu
225                 230                 235                 240
Ser Gly Ser Ser Ser Thr Cys Ser Pro Gly Asn Thr Trp Gln Pro
                    245                 250                 255
Glu Leu Pro Lys Cys Val Arg
            260

<210> SEQ ID NO 587
<211> LENGTH: 263
<212> TYPE: PRT
<213> ORGANISM: Cowpox virus

<400> SEQUENCE: 587

Met Lys Val Glu Ser Val Thr Phe Leu Thr Leu Leu Gly Ile Gly Cys
1               5                   10                  15
Val Leu Ser Cys Cys Thr Ile Pro Ser Arg Pro Ile Asn Met Lys Phe
            20                  25                  30
Lys Asn Ser Val Gly Thr Asp Ala Asn Ala Asn Tyr Asn Ile Gly Asp
            35                  40                  45
Thr Ile Glu Tyr Leu Cys Leu Pro Gly Tyr Arg Lys Gln Lys Met Gly
50                  55                  60
Pro Ile Tyr Ala Lys Cys Thr Gly Thr Gly Trp Thr Leu Phe Asn Gln
65                  70                  75                  80
Cys Ile Lys Arg Lys Cys Pro Ser Pro Arg Asp Ile Asp Asn Gly Gln
            85                  90                  95
Ile Asp Ile Gly Gly Val Glu Phe Gly Ser Ser Ile Thr Tyr Ser Cys
            100                 105                 110
Asn Ser Gly Tyr Gln Leu Ile Gly Glu Ser Lys Ser Tyr Cys Glu Leu
            115                 120                 125
Gly Tyr Thr Gly Ser Met Val Trp Asn Pro Glu Ala Pro Ile Cys Glu
            130                 135                 140
Ser Val Lys Cys Pro Ser Pro Pro Ser Val Thr Asn Gly Arg His Asn
145                 150                 155                 160
Gly Tyr Glu Asp Phe Tyr Thr Asp Gly Ser Val Val Thr Tyr Ser Cys
                    165                 170                 175
Asn Ser Gly Tyr Ser Leu Ile Gly Asn Ser Gly Ile Val Cys Ser Gly
            180                 185                 190
Gly Glu Trp Ser Asp Pro Pro Thr Cys Gln Ile Val Lys Cys Pro His
            195                 200                 205
```

```
Pro Ser Ile Thr Asn Gly Tyr Leu Ser Ser Gly Phe Lys Arg Ser Tyr
    210                 215                 220

Ser His Asn Asp Asn Val Asp Phe Lys Cys Arg His Gly Tyr Lys Leu
225                 230                 235                 240

Ser Gly Ser Ser Ser Thr Cys Ser Pro Gly Asn Thr Trp Gln Pro
                245                 250                 255

Glu Leu Pro Lys Cys Val Arg
            260

<210> SEQ ID NO 588
<211> LENGTH: 216
<212> TYPE: PRT
<213> ORGANISM: Monkeypox virus

<400> SEQUENCE: 588

Met Lys Val Glu Ser Val Thr Phe Leu Thr Leu Leu Gly Ile Gly Cys
1               5                   10                  15

Val Leu Ser Tyr Cys Thr Ile Pro Ser Arg Pro Ile Asn Met Lys Phe
            20                  25                  30

Lys Asn Ser Val Glu Thr Asp Ala Asn Tyr Asn Ile Gly Asp Thr Ile
        35                  40                  45

Glu Tyr Leu Cys Leu Pro Gly Tyr Arg Lys Gln Lys Met Gly Pro Ile
50                  55                  60

Tyr Ala Lys Cys Thr Gly Thr Gly Trp Thr Leu Phe Asn Gln Cys Ile
65                  70                  75                  80

Lys Arg Arg Cys Pro Ser Pro Arg Asp Ile Asp Asn Gly Gln Leu Asp
                85                  90                  95

Ile Gly Gly Val Asp Phe Gly Ser Ser Ile Thr Tyr Ser Cys Asn Ser
            100                 105                 110

Gly Tyr His Leu Ile Gly Glu Ser Lys Ser Tyr Cys Glu Leu Gly Ser
        115                 120                 125

Thr Gly Ser Met Val Trp Asn Pro Glu Ala Pro Ile Cys Glu Ser Val
130                 135                 140

Lys Cys Gln Ser Pro Pro Ser Ile Ser Asn Gly Arg His Asn Gly Tyr
145                 150                 155                 160

Glu Asp Phe Tyr Ile Asp Gly Ser Ile Val Thr Tyr Ser Cys Asn Ser
                165                 170                 175

Gly Tyr Ser Leu Ile Gly Asn Ser Gly Val Met Cys Ser Gly Gly Glu
            180                 185                 190

Trp Ser Asn Pro Pro Thr Cys Gln Ile Val Lys Cys Pro His Pro Ile
        195                 200                 205

Ser Asn Gly Lys Leu Leu Ala Ala
    210                 215

<210> SEQ ID NO 589
<211> LENGTH: 255
<212> TYPE: PRT
<213> ORGANISM: Artificial sequence
<220> FEATURE:
<223> OTHER INFORMATION: Consensus sequence
<220> FEATURE:
<221> NAME/KEY: misc_feature
<222> LOCATION: (102)..(102)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
```

```
<222> LOCATION: (162)..(163)
<223> OTHER INFORMATION: Xaa can be any naturally occurring amino acid
<220> FEATURE:
<221> NAME/KEY: misc_feature
<222> LOCATION: (170)..(170)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid

<400> SEQUENCE: 589

Met Lys Val Glu Ser Val Thr Phe Leu Thr Leu Leu Gly Ile Gly Cys
1               5                   10                  15

Val Leu Ser Cys Cys Thr Ile Pro Ser Arg Pro Ile Asn Met Lys Phe
            20                  25                  30

Lys Asn Ser Val Glu Thr Asp Ala Asn Asn Tyr Asn Ile Gly Asp Thr
        35                  40                  45

Ile Glu Tyr Leu Cys Leu Pro Gly Tyr Arg Lys Gln Lys Met Gly Pro
    50                  55                  60

Ile Tyr Ala Lys Cys Thr Gly Thr Gly Trp Thr Leu Phe Asn Gln Cys
65                  70                  75                  80

Ile Lys Arg Arg Cys Pro Ser Pro Arg Asp Ile Asp Asn Gly Gln Leu
                85                  90                  95

Asp Ile Gly Gly Val Xaa Phe Gly Ser Ser Ile Thr Tyr Ser Cys Asn
            100                 105                 110

Ser Gly Tyr His Leu Ile Gly Glu Ser Lys Ser Tyr Cys Glu Leu Gly
        115                 120                 125

Ser Thr Gly Ser Met Val Trp Asn Pro Glu Ala Pro Ile Cys Glu Ser
    130                 135                 140

Val Lys Cys Gln Ser Pro Pro Ser Xaa Ser Asn Gly Arg His Asn Gly
145                 150                 155                 160

Tyr Xaa Xaa Phe Tyr Thr Asp Gly Ser Xaa Val Thr Tyr Ser Cys Asn
                165                 170                 175

Ser Gly Tyr Ser Leu Ile Gly Asn Ser Gly Xaa Cys Ser Gly Gly Glu
            180                 185                 190

Trp Ser Xaa Pro Pro Thr Cys Gln Ile Val Lys Cys Pro His Pro Ile
        195                 200                 205

Ser Asn Gly Tyr Leu Ser Ser Gly Phe Lys Arg Ser Tyr Ser Asn Asp
    210                 215                 220

Asn Val Asp Phe Cys Gly Tyr Lys Leu Ser Gly Ser Ser Ser Ser Thr
225                 230                 235                 240

Cys Ser Pro Gly Asn Thr Trp Pro Glu Leu Pro Lys Cys Val Arg
                245                 250                 255
```

ANTI-ORTHOPOXVIRUS RECOMBINANT POLYCLONAL ANTIBODY

CROSS REFERENCE TO RELATED APPLICATIONS

This application claims the benefit of Danish Application No. PA 2005 01720, filed Dec. 5, 2005, herein incorporated by reference.

REFERENCE TO A SEQUENCE LISTING SUBMITTED ON A COMPACT DISC

This application includes a "Sequence Listing," which is provided as an electronic document on a compact disc (CD-R). This compact disc contains the file "Sequence Listing ASCII_2488.0020000.txt" (116 kilobytes, created on Mar. 16, 2007), which is hereby incorporated by reference in its entirety.

BACKGROUND OF THE INVENTION

1. Field of the Invention

The present invention relates to a recombinant polyclonal anti-orthopoxvirus antibody (anti-orthopoxvirus rpAb), in particular a recombinant polyclonal anti-vaccinia virus antibody (anti-VV rpAb). The invention also relates to polyclonal expression cell lines producing anti-orthopoxvirus rpAb or anti-VV rpAb. Further, the application describes diagnostic and pharmacological compositions comprising anti-orthopoxvirus rpAb or anti-VV rpAb and their use in prevention, and treatment of adverse effects of vaccination, or diagnosis and treatment of orthopoxvirus infections.

2. Background Art

Smallpox is caused by airway infection with the orthopoxvirus, variola. The threat of smallpox outbreaks as a result of bioterrorism and the emergence of related viruses such as monkeypox, have revived the need for anti-orthopoxvirus therapeutics and vaccination. Vaccinia virus vaccination mediates moderate to severe adverse reactions in approximately one in every 1000. These are currently treated with anti-vaccinia virus immunoglobulin (VIG) isolated from donors with a high antibody titer. However, the estimated incidence of adverse effects resulting from a general vaccination program using live attenuated vaccinia virus exceeds the current production capacity of VIG, thereby preventing vaccination as an approach for public protection against smallpox. Furthermore, VIG has a very low specific activity resulting in a need for injection of large volumes. There is also the risk of transmission of viral diseases from serum derived VIG products, as well as problems with batch-to-batch variations. Therefore, investigations of possible alternatives for providing protecting against vaccinia virus adverse effects or infections by other orthopoxviruses have been conducted.

Orthopoxviruses produces two types infectious particles, namely the Intracellular Mature Virions (EMV) and the Extracellular Enveloped Virions (EEV). IMV plays a predominant role in host-to-host transmission and EEV plays a major role in virus propagation within the host. The IMV particle is assembled in the cytoplasm of infected cells and consists of a virally induced membrane surrounding the genome containing a homogenous core particle. EEV particles are generated by wrapping of IMV particles in a host cell-derived membrane followed by egress of the EEV particle. At a later stage the vaccinia virus infection results in cell death and release of the infectious IMV particles. Viral proteins presented at the surface of IMV or EEV particles are potential targets for antibodies, a total of five IMV-specific proteins and two EEV-specific proteins have been reported to elicit virus neutralizing and/or protective effects when used for immunization or vaccination. Additionally, neutralizing and protective effects have been observed for the passive administration of antibodies which specifically bind these proteins (summarized in Table 1).

TABLE 1

| Antigen | Virion | Antibody effect | Immunization/vaccination effect |
|---|---|---|---|
| A27L (P14) | IMV | + neutralize[11,12,15] (+) protective[11] − protective[15] | DNA: + neutralize + protective[6] Protein: + neutralize + protective[1,8] |
| A17L (P21) | IMV | + neutralize[13] | |
| L1R (P25-29) | IMV | + neutralize[10,14,15] + protective[10,15] | DNA: + neutralize (+) protective[5] Protein: + neutralize + protective[2] |
| D8L (P32) | IMV | + neutralize[15] + protective[15] | Protein: + neutralize + protective[1] |
| H3L (P35) | IMV | + neutralize[4,9] | |
| A33R (Gp23-28) | EEV | + neutralize[10,15] + protective[10,15,16] | DNA: + neutralize + protective[3,5] Protein: + neutralize + protective[2] |
| B5R (Gp42) | EEV | + neutralize[7] + protective[10,16] | DNA: + neutralize (+) protective[3,6] Protein: + neutralize + protective[2,3] |

The column "antibody effect" summarizes results from references describing the effect of an antibody reactive with the named antigen either in in vitro neutralization assays or by in vivo challenging assays to measure protectiveness. The column "immunization/vaccination effect" summarizes results from references where the antigen has been injected into animals either in protein form or as DNA. The neutralizing effect is analyzed by assessing the neutralization titer of the injected animals and the protective effect by challenging the immunized/vaccinated animals with vaccinia virus.

1. Demkowicz et al. 1992, J. Virol. 66:386-98.
2. Fogg et al. 2004, J. Virol. 78:10230-7. This reference also describes increased protection when immunization was performed with the following protein combinations B5R+A33R+L1R>A33R+L1R>A33R+B5R>B5R+L1R
3. Galmiche et al, 1999, Virology 254:71-80.
4. Gordon et al. 1991, Virology 181:671-86
5. Hooper et al. 2000, Virology 266:329-39. This reference also describes increased protection when vaccination was performed with both L1R and A33R encoding DNA.

6. Hooper et al. 2003, Virology 306:181-95. This reference also describes increased protection when vaccination was performed with the following DNA combinations: B5R+A33R+L1R+A27L and B5R+A27L, where the first combination showed better protection than the second combination.
7. Law et al. 2001, Virology 280:132-42.
8. Lai et al. 1991, J. Virol. 65:5631-5.
9. Lin et al. 2000, J. Virol. 74:3353-3365.
10. Lustig et al 2005, J. Virol. 79:13454-13462. This reference also shows enhanced protection when monoclonal antibodies against L1R, A33R and B5R were combined.
11. Ramirez et al. 2002, J. Gen. Virol. 83:1059-1067.
12. Rodriguez et al. 1985, J. Virol. 56:482-488.
13. Wallengren et al. 2001, Virology 290:143-52.
14. Wolffe et al. 1995, Virology 211:53-63.
15. U.S. Pat. No. 6,451,309 illustrates increased protection when monoclonal antibodies against L1R and A33R were combined. Further, L1R and A33R mAbs combined with at least one mAb directed against H3L, D8L, B5R, A27L and A17L is suggested, but there is no evidence of the effect of such a combination.
16. WO 03/068151 suggests individual or combinations of fully human antibodies which binds an EEV protein, in particular B5R, A33R or B7R, where B7R is a variola ortholog of B5R and shares 92.7% identity with it. The application does not contain any evidence of the neutralizing or protective effect of such compositions.

Some of the studies cited in table 1 have revealed that protection against virus challenge is generally increased when protein/DNA combinations targeting both IMV and EEV virion proteins are used for immunization/vaccination (ref. 2, 5, 6 and 10). Similarly, U.S. Pat. No. 6,451,309 illustrated that the combination anti-L1R and anti-A33R mAbs administered to mice prior to a vaccinia virus challenge had an increased protective effect compared to the individual mAbs. This correlates with early observations that vaccination with inactivated IMV particles elicited antibody responses, but did not confer protection to virus challenge in animal experiments (Boulter and Appleyard, 1973, Prog. Med. Virol. 16, 86-108).

The fact that a combination of antibodies is better than a single monoclonal antibody is further supported by the observations by Gordon et al. 1991, Virology 181:671-86, where it was shown that when comparing the neutralizing capability of a single mAb with an anti-VV envelope serum which has been purified with respect to the same antigen specificity as the mAb, or a non-purified polyclonal anti-VV envelope serum, both the purified and non-purified polyclonal anti-envelope serum was much more effective than the monoclonal antibody. Thus, both the binding of antibodies to more than one epitope on the same antigen as well as the binding of several antigens on different proteins is likely to be relevant when neutralizing vaccinia virus.

DISCLOSURE OF CONTRIBUTION

The present invention provides an alternative anti-VV immunoglobulin product which, although it is recombinantly produced, shows reactivity to multiple antigens and epitopes of the orthopoxvirus.

DESCRIPTION OF THE INVENTION

The present invention provides a smallpox countermeasure and an alternative to the serum derived VIG product, in the form of a polyclonal antibody which is capable of binding to multiple antigens and potentially multiple epitopes on individual antigens related to orthopoxvirus infections. In contrast to serum derived VIG, a polyclonal antibody of the present invention does not contain antibody molecules, which bind to non-orthopoxvirus antigens. Thus, the polyclonal antibody of the present invention is essentially free from immunoglobulin molecules that do not bind to orthopoxvirus antigens. Currently, mixtures of three monoclonal antibodies produced in mice (anti-L1R, anti-A33R and anti-B5R) or mixtures of serum derived polyclonal antibodies from rabbits immunized with a particular antigen (L1R, B5R or A33R) are known (Lustig et al 2005, J. Virol. 79: 13454-13462 and U.S. Pat. No. 6,451,309). The rationale behind selecting antibodies against exactly these three antigens was that they are directed against the IMV and EEV particles. However, since the biology of the orthopoxviruses is complex and not completely understood, it is highly likely that there are other antigens in addition to these three antigens which are important for virus neutralization and/or protection and thereby alternative compositions may provide the same or better effects. Further, it has been shown that affinity purified serum has a greater neutralizing effect than a single monoclonal antibody (Gordon et al. 1991, Virology 181:671-86). This is likely to be due to several antibodies binding to different epitopes on the antigen, thereby increasing the complement activation and removal of the antigen.

The present invention provides a polyclonal anti-orthopoxvirus antibody. Preferably, the polyclonal anti-orthopoxvirus antibody is a recombinant polyclonal antibody (anti-orthopoxvirus rpAb), in particular an anti-VV rpAb which is directed against multiple IMV and/or EEV particle proteins and preferably also against multiple epitopes on individual IMV/EEV proteins. Further, antibodies with reactivity against orthopoxvirus related regulators of complement activation (RCA) are a desired component of an anti-orthopoxvirus rpAb of the present invention.

Further, the present invention provides pharmaceutical compositions where the active ingredient is an anti-orthopoxvirus polyclonal antibody, as well as uses of such compositions. For example can an anti-VV rpAb of the present invention serve as replacement of the presently used serum derived VIG and facilitate anti-variola activity for the treatment of smallpox as an anti-terror countermeasure.

The present invention further provides screening procedures suitable for selecting a broad diversity of anti-orthopoxvirus antibodies, and in particular procedures for mirroring the humeral immune response raised upon challenge with an orthopoxvirus, by isolating the original $V_H$ and $V_L$ gene pairs from such challenged individuals, and producing antibodies maintaining this original paring.

DEFINITIONS

The term "antibody" describes a functional component of serum and is often referred to either as a collection of molecules (antibodies or immunoglobulin) or as one molecule (the antibody molecule or immunoglobulin molecule). An antibody molecule is capable of binding to or reacting with a specific antigenic determinant (the antigen or the antigenic epitope), which in turn may lead to induction of immunological effector mechanisms. An individual antibody molecule is usually regarded as monospecific, and a composition of antibody molecules may be monoclonal (i.e., consisting of identical antibody molecules) or polyclonal (i.e., consisting of different antibody molecules reacting with the same or different epitopes on the same antigen or on distinct, different antigens). Each antibody molecule has a unique structure that enables it to bind specifically to its corresponding antigen, and all natural antibody molecules have the same overall basic structure of two identical light chains and two identical heavy chains. Antibodies are also known collectively as immunoglobulin. The terms antibody or antibodies as used herein is used in the broadest sense and covers intact antibodies, chimeric, humanized, fully human and single chain antibodies, as well as binding fragments of antibodies, such as Fab, Fv fragments or scFv fragments, as well as multimeric forms such as dimeric IgA molecules or pentavalent IgM.

The term "anti-orthopoxvirus recombinant polyclonal antibody" or "anti-orthopoxvirus rpAb" describes a composition of recombinantly produced diverse antibody molecules, where the individual members are capable of binding to at least one epitope on a virus belonging to the genus orthopoxvirus. Preferably, an anti-orthopoxvirus rpAb composition is reactive to more than one virus species or strain belonging to the genus orthopoxvirus. Preferably, the composition is produced from a single manufacturing cell line, but may also be a mixture of monoclonal antibodies or any combination of an anti-orthopoxvirus rpAb composition and one or more monoclonal antibodies. The diversity of the polyclonal antibody is located in the variable regions ($V_H$ and $V_L$ regions), in particular in the CDR1, CDR2 and CDR3 regions.

The term "anti-VV recombinant polyclonal antibody" or "anti-VV rpAb" describes a composition of recombinantly produced diverse antibody molecules, where the individual members are capable of binding to at least one epitope on a vaccinia virus species or strain. Preferably, an anti-VV rpAb composition is reactive to at least one IMV and at least one EEV specific antigen, where the reactivity is characterized by distinct members reactive to either an IMV or an EEV specific antigen. Preferably, the composition is produced from a single manufacturing cell line, but it may also be a mixture of monoclonal antibodies. The diversity of the polyclonal antibody is located in the variable regions ($V_H$ and $V_L$ regions), in particular in the CDR1, CDR2 and CDR3 regions.

The term "the polyclonal antibody of the present invention is essentially free from immunoglobulin molecules that do not bind to orthopoxvirus antigens" means that more than 80% of the antibodies, preferably more than 90%, more preferably more than 95% and most preferably more than 99%, bind to one of the orthopoxvirus antigens.

The term "cognate $V_H$ and $V_L$ coding pair" describes an original pair of $V_H$ and $V_L$ coding sequences contained within or derived from the same cell. Thus, a cognate $V_H$ and $V_L$ pair represents the $V_H$ and $V_L$ pairing originally present in the donor from which such a cell is derived. The term "an antibody expressed from a $V_H$ and $V_L$ coding pair" indicates that an antibody or an antibody fragment is produced from a vector, plasmid or similar containing the $V_H$ and $V_L$ coding sequence. When a cognate $V_H$ and $V_L$ coding pair is expressed, either as a complete antibody or as a stable fragment thereof, they preserve the binding affinity and specificity of the antibody originally expressed from the cell they are derived from. A library of cognate pairs is also termed a repertoire or collection of cognate pairs, and may be kept individually or pooled.

The terms "a distinct member of a recombinant polyclonal antibody" denotes an individual antibody molecule of the recombinant polyclonal antibody composition, comprising one or more stretches within the variable regions, which are characterized by differences in the amino acid sequence compared to the other individual members of the polyclonal protein. These stretches are in particular located in the CDR1, CDR2 and CDR 3 regions.

The term "epitope" is commonly used to describe a site on a larger molecule (e.g. antigen) to which the antibody will bind. An antigen is a substance that stimulates an immune response, e.g. toxin, virus, bacteria, proteins or DNA. An antigen often has more than one epitope, unless they are very small. Antibodies binding to different epitopes on the same antigen can have varying effects on the activity of the antigen they bind depending on the location of the epitope. An antibody binding to an epitope in an active site of the antigen may block the function of the antigen completely, whereas another antibody binding at a different epitope may have no or little effect on the activity of the antigen. Such antibodies, may however still activate complement and thereby result in the elimination of the antigen.

The term "fully human" used for example in relation to DNA, RNA or protein sequences describes sequences which are between 98 to 100% human.

The term "immunoglobulin" commonly is used as a collective designation of the mixture of antibodies found in blood or serum, but may also be used to designate a mixture of antibodies derived from other sources.

The term "mirrors the humeral immune response" when used in relation to a polyclonal antibody refers to an antibody composition where the nucleic acid sequences encoding the individual antibody members are derived from a donor who either has been subject to vaccination with an orthopoxvirus or who is recovering from an infection with an orthopoxvirus. In order to mirror the affinity and specificity of antibodies raised in a donor upon challenge, the sequences encoding the variable heavy chain ($V_H$) and the variable light chain ($V_L$) should be maintained in the gene pairs or combinations originally present in the donor (cognate pairs) when they are isolated. In order to mirror the diversity of a humeral immune response in a donor all the sequences encoding antibodies which bind to an orthopoxvirus are selected based on a screening procedure. The isolated sequences are analyzed with respect to diversity of the variable regions, in particular the CDR regions, but also with respect to the $V_H$ and $V_L$ family. Based on these analyses a population of cognate pairs representing the overall diversity of the orthopoxvirus binding antibodies are selected. Such a polyclonal antibody typically have at least 8, 10, 20, 30, 40, 50, 100, 1000 or $10^4$ distinct members.

The term "orthopoxvirus" refers to a virus species or strain belonging to the genus orthopoxvirus. Known viruses include Buffalopox, California vole pox, camelpox, cowpox, ectromelia, monkeypox, rabbitpox, raccoon pox, tatera pox, Uasin Gishu pox, vaccinia, variola, and vole pox virus.

A composition is said to be "pharmacologically acceptable" if its administration can be tolerated by a recipient patient.

The term "unit dose form" refers to a ready-to-administer form comprising a therapeutically effective amount of the active ingredient.

The term "polyclonal antibody" describes a composition of different (diverse) antibody molecules which is capable of binding to or reacting with several different specific antigenic determinants on the same or on different antigens. Usually, the variability of a polyclonal antibody is located in the so-called variable regions of the polyclonal antibody, in particular in the CDR regions. In the present invention a polyclonal antibody may either be produced in one pot from a polyclonal cell line, or it may be a mixture of different polyclonal antibodies. A mixture of monoclonal antibodies is not as such considered a polyclonal antibody, since they are produced in individual batches and not necessarily form the same cell line which will result in e.g. post translational modification differences. However, if a mixture of monoclonal antibodies provide the same antigen/epitope coverage as a polyclonal antibody of the present invention it will be considered as an equivalent of the polyclonal antibody. When stating that a member of a polyclonal antibody binds to an antigen, it is herein meant a binding having binding constant that is below 100 nM, preferably below 10 nM, even more preferred below 1 nM.

The term "recombinant antibody" is used to describe an antibody molecule or several molecules that is/are expressed from a cell or cell line transfected with an expression vector comprising the coding sequence of the antibody which is not naturally associated with the cell. If the antibody molecules in a recombinant antibody composition are diverse or different, the term "recombinant polyclonal antibody" or "rpAb" applies in accordance with the definition of a polyclonal antibody.

The term "recombinant polyclonal cell line" or "polyclonal cell line" refers to a mixture/population of protein expressing cells that are transfected with a repertoire of variant nucleic acid sequences (e.g. a repertoire of antibody encoding nucleic acid sequences). Preferably, the transfection is performed such that the individual cells, which together constitute the recombinant polyclonal cell line, each carry a transcriptionally active copy of a single distinct nucleic acid sequence of interest, which encodes one member of the recombinant polyclonal antibody of interest. Even more preferred, only a single copy of the distinct nucleic acid sequence is integrated at a specific site in the genome. The cells constituting the recombinant polyclonal cell line are selected for their ability to retain the integrated copy of the distinct nucleic acid sequence of interest, for example by antibiotic selection. Cells which can constitute such a polyclonal cell line can be for example bacteria, fungi, eukaryotic cells, such as yeast, insect cells, plant cells or mammalian cells, especially immortal mammalian cell lines such as CHO cells, COS cells, BHK cells, myeloma cells (e.g., Sp2/0 cells, NS0), NIH 3T3, YB2/0 and immortalized human cells, such as HeLa cells, HEK 293 cells, or PER.C6.

The terms "sequences encoding $V_H$ and $V_L$ pairs" or "$V_H$ and $V_L$ encoding sequence pairs" indicate nucleic acid molecules, where each molecule comprise a sequence that code for the expression of a variable heavy chain and a variable light chain, such that these can be expressed as a pair from the nucleic acid molecule if suitable promoter and/or IRES regions are present and operably linked to the sequences. The nucleic acid molecule may also code for part of the constant regions or the complete constant region of the heavy chain and/or the light chain, allowing for the expression of a Fab fragment, a full-length antibody or other antibody fragments if suitable promoter and/or IRES regions are present and operably linked to the sequences.

A recombinant polyclonal antibody is said to be administered in a "therapeutically effective amount" if the amount administered is physiologically significant, e.g. prevents or attenuates an orthopoxvirus infection in an animal or human.

DESCRIPTION OF THE DRAWINGS

FIG. 1: Alignment of amino acid sequences of known orthopoxvirus related regulators of complement activation (RCA), including a consensus sequence.

FIG. 2: Schematic outline of the multiplex overlap-extension RT-PCR (A) and the cloning steps (B). (A) Two sets of primers, CH+VH 1-8 and VK1-6+CK1, specific for $V_H$ and Vκ gene families, respectively, were used for the first PCR step. A homologous region between the $V_H$ or Vκ primers results in the generation of an overlap PCR product. In the second step this product is amplified in the nested PCR. The primers also include recognition sites for restriction enzymes that facilitate cloning. (B) The generated cognate linked $V_H$ and Vκ coding pairs are pooled and inserted into a Fab expression vector by the use of the flanking XhoI and NotI restriction sites. Subsequently a bi-directional promoter is inserted into the AscI-NheI restriction site between the linked $V_H$ and Vκ coding sequences to facilitate Fab expression. PCR primers used are indicated by horizontal arrows. CH1: heavy chain constant domain 1, CL: constant domain, LC: light chain; Ab: antibody; P1-P2: bi-directional promoters.

FIG. 3: Schematic presentations of suitable Fab expression vectors. A) Shows JSK301, an *E. coli* Fab expression vector with NotI/XhoI restriction sites for insertion of linked $V_H$ and $V_L$ coding pairs. The vector comprises the following elements: Amp and Amp pro=ampicillin resistance gene and its promoter. pUC19 Ori=origin of replication. Human CH1=sequence encoding human immunoglobulin gamma 1 heavy chain domain 1. Stuffer=an irrelevant sequence insert which is cut out upon insertion of the overlap-extension fragments. tac P and lac Z=bacterial promoters which can be excised at the NheI and AscI restriction sites and substituted with other promoter pairs. B) Shows a mammalian Fab expression vector with NotI/XhoI restriction sites for insertion of linked $V_H$ and $V_L$ coding pairs. The vector comprises the following elements: Amp and Amp pro=ampicillin resistance gene and its promoter. pUC origin=origin of replication. Rabbit B-globin A=rabbit beta-globin polyA sequence. IgG1 CH1=sequence encoding human immunoglobulin gamma 1 heavy chain domain 1. $V_H$=sequence encoding variable heavy chain. HC leader=A genomic human heavy chain leader. P1=mammalian promoter driving the expression of the light chain. P2=mammalian promoter driving the expression of the heavy chain. Kappa leader=A murine genomic kappa chain leader. LC=light chain encoding sequence. SV40 term=Simian virus 40 terminator sequence. Neo=Neomycin resistance gene. SV40 PolyA=Simian virus 40 poly A signal sequence.

FIG. 4: A schematic presentation of a mammalian full-length antibody expression vector 00-VP-530. The vector comprises the following elements: Amp and Amp pro=ampicillin resistance gene and its promoter. pUC origen=pUC origin of replication. P1=mammalian promoter driving the expression of the light chain. P2=mammalian promoter driving the expression of the heavy chain. Leader IGHV=genomic human heavy chain leader. $V_H$=heavy chain variable region encoding sequence. IgG1=Sequence encoding for genomic immunoglobulin isotype G1 heavy chain constant region. Rabbit B-globin A=rabbit beta-globin polyA sequence. Kappa leader=sequence encoding for murine kappa leader. LC=Sequence encoding light chain encoding sequence. SV40 term=Simian virus 40 terminator sequence. FRT=A Flp recognition target site. Neo=neomycin resistance gene. SV40 poly A=Simian virus 40 poly A signal sequence FIG. 5: Representative Western blots of the identified antigen groups. Virus particles or recombinant antigens were separated by SDS-PAGE, and blotted. The Western blots were probed with the indicated antibody identified by its clone number. The identified antigens are indicated above each blot. The antigen group assigned A did not give any detectable band in Western blot. M indicates the marker. The size of the marker is 20 kDa, 30 kDa, 40 kDa, 50 kDa, 60 kDa, 80 kDa, 100 kDa, 120 kDa.

FIG. 6: Flow chart illustrating the antibody screening process. The Fab fragments or full length antibodies (Abs) were screened against inactivated vaccinia virus strains and recombinant vaccinia virus associated protein in a first round of screening generating primary hits. The primary hits were then subjected to a second round of screening. Generally the first round of screening was performed using FLISA and the second round of screening was performed with FLISA and/or ELISA. The figure exemplifies EEV or non-particle associated proteins as recombinant vaccinia virus associated proteins. However recombinant IMV specific proteins such as L1R can also be used.

FIG. 7: Anti-vaccinia virus reactivity in 10 donors (indicated by D-001 to D-011). Antibody titers against recombinant antigens A27L, A33R, B5R, L1R, and VCP and virus particles from different strains (Lister, IHD-W, IHD-J) were determined as the minimum dilution producing a signal 4-fold above background in ELISA.

FIG. 8: Anti-vaccinia virus reactivity of the Mini-H and Mini-V compositions compared to the serum derived SymVIG. The binding was detected by ELISA using inactivated Lister strain particles as antigen and the negative control was anti-RhD polyclonal antibody.

FIG. 11: Vaccinia virus binding of the three anti-VV rpAb batches and the two VIG products, SymVIG and Cangene VIG (VIG). The binding was tested in ELISA against the antigens indicated at the top of each plot.

DETAILED DESCRIPTION OF THE INVENTION

Target Antigens and Polyclonal Antibody Compositions

Figure 4:
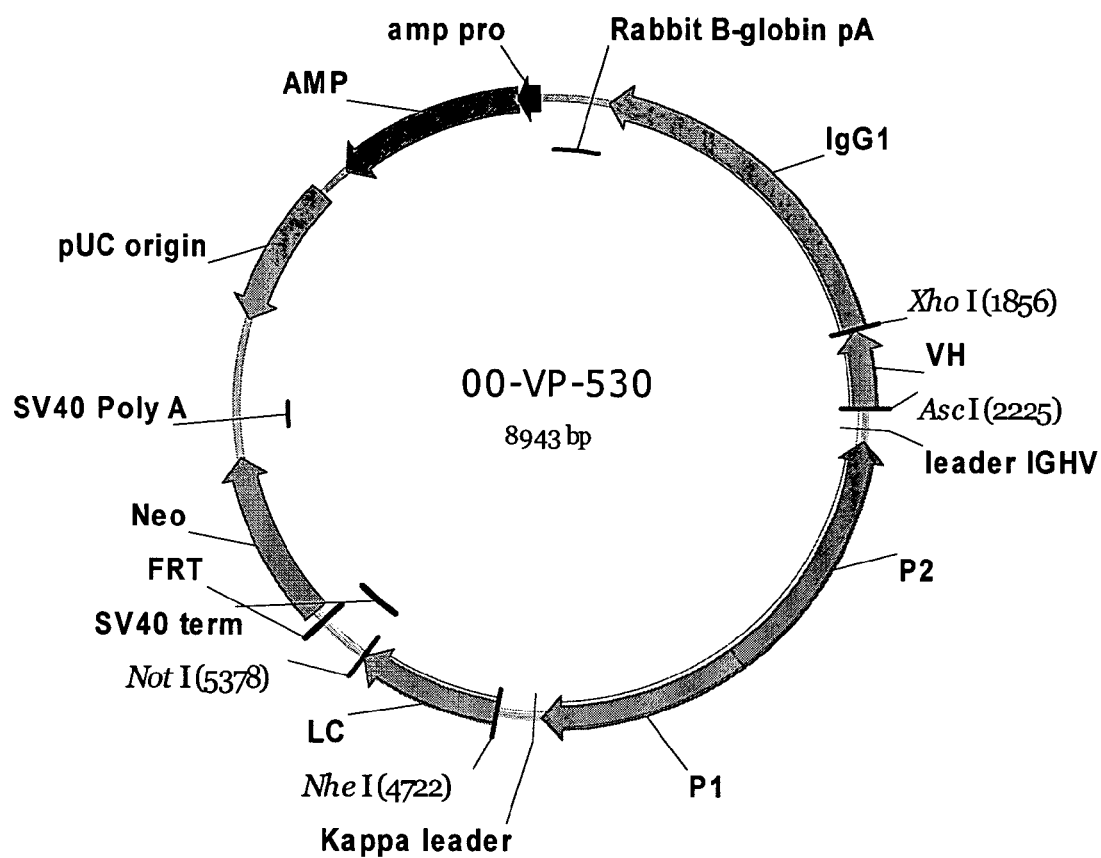
Figure 5:
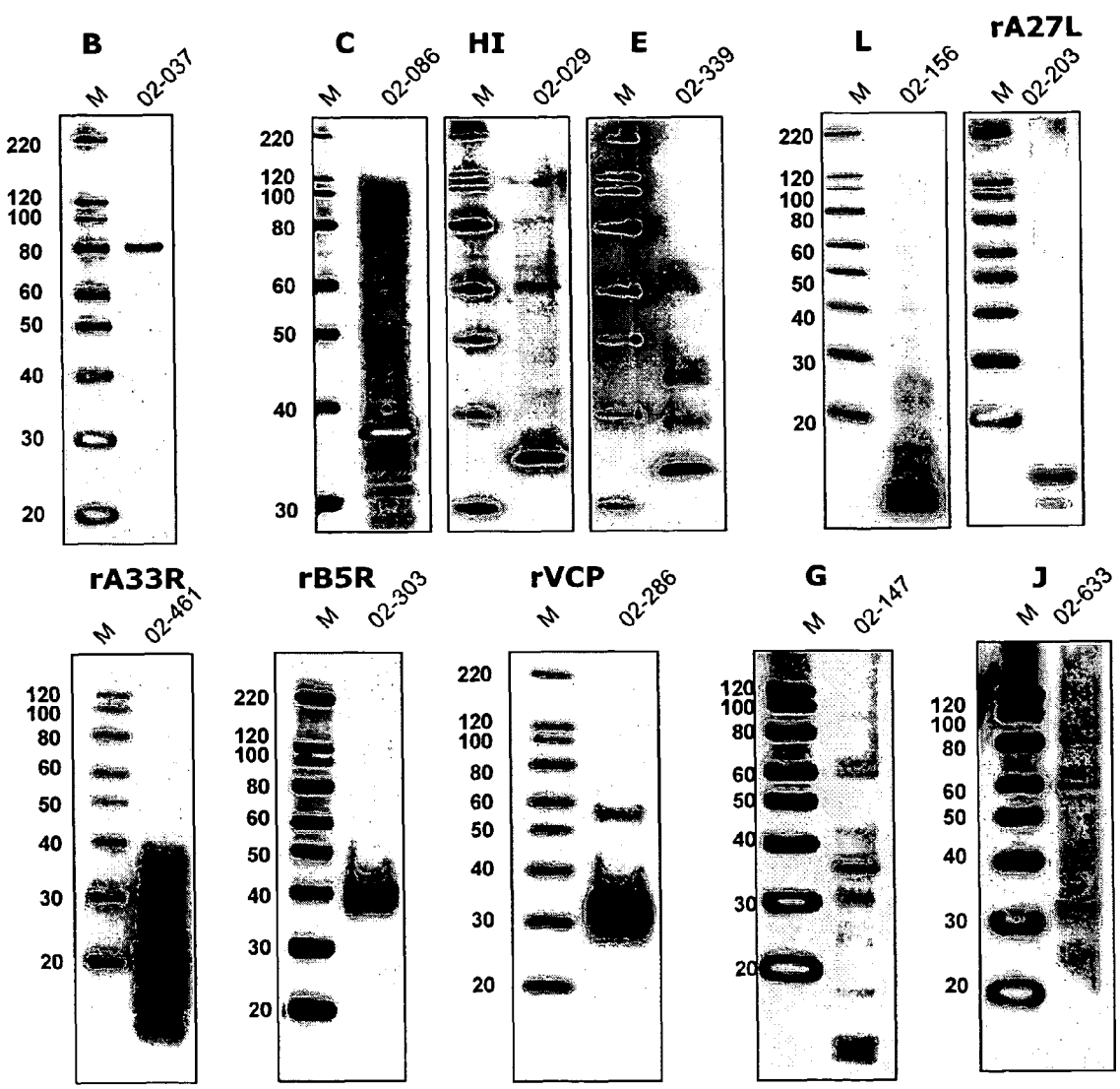

A polyclonal antibody of the present invention is composed of a number of distinct antibody molecules in the same composition. Each molecule is selected based on its ability to bind an orthopoxvirus associated antigen. Preferably, the distinct members of a polyclonal anti-orthopoxvirus antibody of the present invention are capable of binding at least three orthopoxvirus related antigens in union. Further, it is preferred that each distinct antibody of the polyclonal antibody binds an epitope which is not bound by any of the other members of the polyclonal antibody. An antibody of the polyclonal antibody composition may bind an epitope which overlaps epitopes of other distinct antibodies of the composition and still be considered a distinct antibody. An additional feature of an anti-orthopoxvirus polyclonal antibody of the present invention is the capability of binding at least two distinct epitopes on the same orthopoxvirus related antigen, thereby supplementing the binding to at least three different orthopoxvirus associated antigens. Such a polyclonal antibody is, hence, composed of at least 4 distinct antibody members. A polyclonal antibody of the present invention comprises binding reactivity corresponding to the compiled binding reactivity of the distinct antibody molecules constituting the polyclonal antibody composition. Preferably, a polyclonal antibody of the present invention is produced as a single batch or a few batches from a polyclonal cell line which is not naturally expressing antibody molecules (also termed a recombinant polyclonal antibody). One of the advantages of producing a recombinant polyclonal antibody compared to mixing monoclonal antibodies, is the ability to produce an principally unlimited number of distinct antibody molecules at the same time (at a cost similar to that of producing a single monoclonal antibody). Thus, it is possible to include antibodies with reactivity towards a large number of orthopoxvirus associated antigens, known as well as unknown, without increasing the cost of the end product significantly. In particular with a target as complex as the orthopoxviruses where the biology is not completely understood, individual antibodies which have not been shown to neutralize or protect against orthopoxviruses alone, may when combined with other antibodies induce a synergistic effect. Thus, it can be an advantage to include distinct antibodies in a polyclonal antibody composition, where the only criterion is that the individual antibody binds to an orthopoxvirus antigen.

One way to acquire potentially relevant antibodies that bind orthopoxvirus target antigens which have not been verified as relevant antigens, but none the less may be so, is to generate a polyclonal antibody composition which is composed of individual antibodies raised by the immune response of a donor which has been vaccinated or infected with an orthopoxvirus (full immune response). In addition to broadly obtaining antibodies derived from a full immune response against othopoxviruses, a positive selection for antibodies binding to antigens that are likely to be of particular relevance in the protection, neutralization, and/or elimination of orthopoxvirus infections or in the protection against adverse effects from vaccina virus vaccination, can be performed. Further, if antibodies to a particular antigen, which is known to be of relevance in the protection, neutralization and/or elimination of orthopoxvirus are not identified in the full immune response of the donor, such antibodies may be raised by immunization/vaccination of a donor with that particular antigen (selected immune response). Generally, neutralization is assessed by in vitro neutralization assays such as plaque reduction neutralization assays (PRNT assay) using either IMV or EEV preparations, by comet assay, EEV neutralization assay (EEV specific) (Law et al. 2001, Virology 280:132-42) or by flow cytometric detection of green fluorescent protein (Earl et al. 2003 J. Virol. 77:10684-88). Protection is generally assessed by in vivo challenging experiments such as the mouse tail lesion model, lethal dose challenge or footpad measurements. The in vivo challenging experiments can either be performed in a prophylactic fashion, where the antibodies are administered prior to the viral challenge or as a treatment, where the antibodies are administered after viral challenge or as a combination of both.

A polyclonal antibody composition of the present invention can be composed of antibodies capable of binding an orthopoxvirus antigen which is not necessarily known, but where the antibodies are acquired from a full immune response to an orthopoxvirus, e.g. by obtaining nucleic acid sequences encoding the distinct antibodies from one or more donors vaccinated with an orthopoxvirus, or recovering from an orthopoxvirus infection. Secondly, antibodies from the same full immune response, which have been selected based on their ability to bind a particular antigen and/or epitope, can be included in a polyclonal antibody of the present invention. Thirdly, distinct antibodies encoded from $V_H$ and $V_L$ pairs obtained from one or more donors which have been immunized/vaccinated with a particular orthopoxvirus related antigen thereby raising a "selected" immune response in these donors, can be included in a polyclonal antibody composition of the present invention. Thus, antibodies derived by any of the mentioned techniques in the present invention may be combined into a single polyclonal antibody. Preferably the nucleic acids encoding the antibodies of the present invention are obtained from human donors and the antibodies produced are fully human antibodies.

The motivation behind the polyclonal antibody compositions of the present invention is: if a donor immunized or infected with an orthopoxvirus, raises an humeral immune response against an antigen, these antibodies are likely at least to some extend to contribute to viral clearance, and thereby qualify for inclusion in a polyclonal antibody product.

One embodiment of the present invention is an anti-orthopoxvirus rpAb wherein the composition of distinct antibody members mirrors the humeral immune response with respect to diversity, affinity and specificity against antigens associated with one or more orthopoxviruses, in particular vaccinia virus, variola virus and/or monkeypox virus. Preferably, the mirror of the humeral response is established by ensuring that one or more of the following are fulfilled i) the nucleic acid sequences coding for the $V_H$ and $V_L$ regions of the individual antibody members in such an anti-orthopoxyirsus rpAb are derived from a donor(s) who has raised a humeral immune response against an orthopoxvirus, for example following vaccination with vaccinia virus or an *orthopox* virus infection from which the donor is recovering; ii) the $V_H$ and $V_L$ coding sequences are isolated from the donor(s) such that the original pairing of the $V_H$ and $V_L$ coding sequences present in the donor(s) is maintained, iii) the $V_H$ and $V_L$ pairs, coding for the individual members of the rpAb, are selected such that the CDR regions are as diverse as possible; or iv) the specificity of the individual members of the anti-orthopoxvirus rpAb are selected such that the antibody composition collectively binds antigens that elicit significant antibody responses in mammals. Preferably, the antibody composition collectively binds antigens which produce significant antibody titers in a serum sample from said donor(s).

The antigens of relevance to the present invention are any orthopoxvirus derived protein, polypeptide or nucleic acid, towards which a humeral immune response or a selected immune response can be raised. The relevant antigens can be selected from viral proteins presented at the surface of IMV and/or EEV particles. At least twelve different viral proteins, (here referred to by the vaccinia virus variants) A14.5L, E10R, 15L, A13L, A27L, A17L, L1R, L5R, D8L, H3L, A14L and A17L, are inserted in the IMV outer membrane and may be relevant antigens according to the present invention. Further, at least six other proteins, A33R, A34R, F13L, B5R, A56R, F12L and A36R, are present at the surface membrane of the EEV particle and may likewise be relevant antigens according to the present invention.

In an additional embodiment of the present invention the anti-orthopoxvirus rpAb comprises binding reactivity against antigens selected from the group of viral proteins associated with IMV and/or EEV particles, in particular proteins presented on the surface of these particles. In a preferred embodiment of the present invention the anti-orthopoxvirus rpAb comprises binding reactivity against antigens selected among the viral proteins A27L, A17L, D8L and H3L, and against antigens selected among the viral proteins A33R and B5R. Additionally, the first group can constitute the viral proteins L1R and the second group can constitute the viral protein A56R.

Further, additional orthopoxvirus proteins have shown immunoreactivity in humans, macaques and/or mice following vaccination with vaccinia virus. These include the vaccinia virus ortholog A10L, A11R, D13L, H5R, A26L, E3L, L4R, H7R, P4A and A4L (Davies et al. 2005, PNAS 102: 547-552 and Demkowicz et al. 1992, J. Virol. 66:386-98), and are also considered as potentially relevant antigens to which individual members of a polyclonal antibody according to the present invention can bind. In a further embodiment of the present invention, the polyclonal antibody comprises binding reactivity against one or more of the antigens selected from the following group of viral proteins, represented as the vaccinia virus ortholog A14.5L, E10R, 15L, A13L, A27L, A17L, L1R, D8L, H3L, A14L, A17L, A33R, A34R, F13L, B5R, A56R, F12L, A36R, A10L, A11R, D13L, H5R, A26L, E3L, L4R, H7R, P4A and A4L.

The viral proteins mentioned above are, however, not the only viral proteins with potential relevance in the protection, neutralization and/or elimination of orthopoxvirus infections or prevention of adverse effects due to vaccination with vaccinia virus. The orthopoxviruses encode regulators of complement activation (RCA), that contain four tandem short consensus repeats (SCRs), allowing them to evade the consequences of complement activation in the host (reviewed in Mullick et al. 2003, Trends Immunol. 24:500-7). Several RCA proteins have been identified in the group of orthopoxviruses, namely vaccinia virus complement control protein (VCP), smallpox inhibitor of complement enzyme (SPICE) and inflammatory modulatory protein (IMP), from vaccinia virus, variola virus and cowpox, respectively. Certain monkeypox viral strains also have an ortholog of the VCP, which may be responsible for the violence of these particular strains, compared to other monkeypox strains (Chen et al. 2005, Virology 340:46-63). Further, a sequence relating to a VCP protein from camelpox virus has also been identified under NCBI accession number AAL73730. FIG. 1 shows an alignment of the mentioned RCA proteins, including an orthopoxvirus RCA protein consensus sequence. U.S. 2005/0129700 describes the generation of anti-VCP and anti-SPICE antibodies, preferably with reactivity to both antigens. The monoclonal antibodies are used to pre-inject animals which are subjected to vaccinia virus vaccination, there are however no indication whether the antibodies are protective or not. Further, a series of monoclonal mouse antibodies against VCP has been generated in order to map the SCR domains involved in abolishing complement-enhanced neutralization. Antibodies binding to the SCR2, SCR4 or the junction between the SCR3 and 4 domains blocked the interaction of VCP with complement (Isaacs et al. 2003, J. Virol. 77:8256-62).

In further embodiments of the present invention the above mentioned polyclonal antibody compositions additionally comprise binding reactivity against an RCA encoded by an orthopoxvirus. In particular a polyclonal anti-orthopoxvirus composition comprising binding reactivity against IMV, EEV and RCA specific antigens is desired. A further anti-orthopoxvirus polyclonal antibody of the present invention comprises binding reactivity against antigens selected among the viral proteins (vaccinia virus orthologs) A27L, A17L, D8L, H3L, A33R, B5R and VCP. Additionally, the group can constitute the viral proteins L1R and/or A56R. In any of the embodiments of the present invention relating to RCA specific antibody members, the RCA binding specificity is preferably directed against a protein selected from the group VCP, SPICE, IMP, MPXV-VCP and CMLV-VCP. In a preferred embodiment the rpAb compositions of the present invention comprises individual members with binding reactivity against the orthopoxvirus RCA protein consensus sequence. In an even more preferred embodiment the RCA related binding reactivity is directed to an epitope located in the SCR2, SCR4 and/or the junction between the SCR3 and 4 domains of one of the mentioned RCA proteins or the RCA protein consensus sequence. Preferably the VCP reactivity is directed against the SCR2, SCR4 and/or the junction between the SCR3 and 4 domains.

The present invention has identified a series of $V_H$ and $V_L$ pairs that can be expressed as full-length antibodies, Fab fragment or other antibody fragments that have binding specificity to an vaccinia virus associated antigen. The specific $V_H$ and $V_L$ pairs are identified by clone number in Table 5 in Example 2. An antibody containing a $V_H$ and $V_L$ pair as identified in Table 5 is preferably a fully human antibody. However, if desired chimeric antibodies may also be produced.

A preferred anti-orthopoxvirus recombinant polyclonal antibody of the present invention is composed of distinct members comprising heavy chain and light chain CDR1, CDR2 and CDR3 regions selected from the group of $V_H$ and $V_L$ pairs listed in Table 5. Preferably, the CDR regions are maintained in the pairing indicated in Table 5 and inserted into a desired framework. Alternatively CDR regions from the heavy chain (CDRH) of a first clone are combined with the CDR regions from the light chain (CDRL) of a second clone (scrambling of $V_H$ and $V_L$ pairs). The CDR regions may also be scrambled within the light chain or heavy chain, for example by combining the CDRL1 region from a first clone with the CDRL2 and CDRL3 region from a second clone. Such scrambling is preferably performed among clones that bind the same antigen. The CDR regions of the present invention may also be subjected to affinity maturation, e.g. by point mutations.

An even more preferred anti-orthopoxvirus recombinant polyclonal antibody of the present invention is comprised of distinct members with heavy chain and light chain CDR1, CDR2 and CDR3 regions corresponding to clone numbers 02-029, 02-037, 02-058, 02-086, 02-147, 02-186, 02-188, 02-195, 02-197, 02-203, 02-211, 02-229, 02-235, 02-286, 02-295, 02-303, 02-339, 02-461, 02-482, 02-488, 02-526, 02-551, 02-586, 02-589, 02-607 and 02-633.

In a further embodiment, the above composition, comprising 26 individual members, additionally comprise the following two distinct members with heavy chain and light chain CDR1, CDR2 and CDR3 regions corresponding to clone numbers 02-113 and 02-225.

A further aspect of the present invention is the individual antibodies, identified by the method of the present invention, which bind previously unidentified epitopes of an orthopoxvirus, in particular vaccinia virus and/or variola virus.

In addition to the antigens mentioned above, individual antibodies with binding specificity towards unidentified antigens can be identified by for example Western blot analysis using inactivated orthopoxvirus particles as antigen source. These unidentified antigens may correspond to known antigens, but they may also correspond to unknown antigens. The identity of an antigen toward which an antibody of the present invention binds, can be assessed by analyzing binding specificity of the identified antibodies to recombinant proteins of known antigens. Alternatively, competition assays against antibodies with a known specificity can be performed. Such competition assays does, however, not exclude that the identified antibody binds to the same antigen as the known antibody, since it may bind to a different epitope.

The present invention has identified antibodies against the following antigens from the Lister strain by Western blotting: B (~82 kDa), C (35-40 kDa), D (Three band appearance ~65, ~72, ~95 kDa), E (32-35 kDA), G (Three band appearance 80 kDa, 60 kDa, 31-33 kDa), HI (~35 Da), J (35-38 kDa) and L (<20 kDa). Antibodies against the known antigen VCP, B5R, A27L and A33R have also been verified by Western blotting. By using in vitro translated proteins the HI antigen was shown to correspond to antigen H3L, the E antigen to D8L, the D antigen to A56R, the remaining antigens does not correspond to VCP, B5R, A27L, A33R or H3L, D8L, A56R and the antibodies binding to these unidentified antigens may potentially bind to previously unknown orthopoxvirus antigens or epitopes.

An embodiment of the present invention is an antibody binding antigen B of the Lister strain at the same epitope as an antibody comprising three heavy chain CDRs and three light-chain CDRs derivable from clone nr. 02-037, 02-089 and/or 02-058.

An embodiment of the present invention is an antibody binding antigen C of the Lister strain at the same epitope as an antibody comprising three heavy chain CDRs and three light-chain CDRs derivable from clone nr. 02-243.

An embodiment of the present invention is an antibody binding antigen D or A56R of the Lister strain at the same epitope as an antibody comprising three heavy chain CDRs and three light-chain CDRs derivable from clone nr. 02-628, 02-431, 002-516 and/or 02-551.

An embodiment of the present invention is an antibody binding antigen E or D8L of the Lister strain at the same epitope as an antibody comprising three heavy chain CDRs and three light-chain CDRs derivable from clone nr. 02-339.

An embodiment of the present invention is an antibody binding antigen G of the Lister strain at the same epitope as an antibody comprising three heavy chain CDRs and three light-chain CDRs derivable from clone nr. 02-147.

An embodiment of the present invention is an antibody binding antigen J of the Lister strain at the same epitope as an antibody comprising three heavy chain CDRs and three light-chain CDRs derivable from clone nr. 02-640 and/or 02-633.

An embodiment of the present invention is an antibody binding antigen L of the Lister strain at the same epitope as an antibody comprising three heavy chain CDRs and three light-chain CDRs derivable from clone nr. 02-589, 02-156, and/or 02-225.

Isolation and Selection of Variable Heavy Chain and Variable Light Chain Coding Pairs The process of generating an anti-orthopoxvirus recombinant polyclonal antibody composition involves the isolation of sequences coding for variable heavy chains ($V_H$) and variable light chains ($V_L$) from a suitable source, thereby generating a repertoire of $V_H$ and $V_L$ coding pairs. Generally, a suitable source for obtaining $V_H$ and $V_L$ coding sequences are lymphocyte containing cell fractions such as blood, spleen or bone marrow samples from an animal or human immunized/vaccinated with an orthopoxvirus strain or proteins or DNA derived from such a strain. Preferably, lymphocyte containing fractions are collected from humans or transgenic animals with human immunoglobulin genes, which have been vaccinated with a vaccinia virus strain, such a strain can for example be selected from a group of strains comprising Connaught, IHD-J, IHD-W, Brighton, WT, Lister, NYCBOH, Copenhagen, Ankara, Dairen I, L-IPV, LC16MO, LIVP, Tian Tan, WR 65-16, and Wyeth or proteins or DNA derived from such a strain. Patients recovering from an infection with an orthopoxvirus strain can also be used as source for the $V_H$ and $V_L$ gene isolation. The collected lymphocyte containing cell fraction may be enriched further to obtain a particular lymphocyte population, e.g. cells of the B lymphocyte lineage. Preferably, the enrichment is performed using magnetic bead cell sorting (MACS) and/or fluorescence activated cell sorting (FACS), taking advantage of lineage-specific cell surface marker proteins for example for B cells and/or plasma cells. Preferably, the lymphocyte containing cell fraction is enriched with respect to B cells and/or plasma cells. Even more preferred cells with high CD19 and CD38 expression and intermediate CD45 expression are isolated from blood. These cells are sometimes termed circulating plasma cells, early plasma cells or plasmablasts, for ease, they are just termed plasma cells in the present invention.

The isolation of $V_H$ and $V_L$ coding sequences can either be performed in the classical way where the $V_H$ and $V_L$ coding sequences are combined randomly in a vector to generate a combinatorial library of $V_H$ and $V_L$ coding sequences pairs. However, in the present invention it is preferred to mirror the diversity, affinity and specificity of the antibodies produced in a humeral immune response upon challenge with an orthopoxvirus. This involves the maintenance of the $V_H$ and $V_L$ pairing originally present in the donor, thereby generating a repertoire of sequence pairs where each pair encodes a variable heavy chain ($V_H$) and a variable light chain ($V_L$) corresponding to a $V_H$ and $V_L$ pair originally present in an antibody produced by the donor from which the sequences are isolated. This is also termed a cognate pair of $V_H$ and $V_L$ encoding sequences and the antibody is termed a cognate antibody. Preferably, the $V_H$ and $V_L$ coding pairs of the present invention, combinatorial or cognate, are obtained from human donors, and therefore the sequences are completely human.

There are several different approaches for the generation of cognate pairs of $V_H$ and $V_L$ encoding sequences, one approach involves the amplification and isolation of $V_H$ and $V_L$ encoding sequences from single cells sorted out from a lymphocyte-containing cell fraction. The $V_H$ and $V_L$ encoding sequences may be amplified separately and paired in a second step or they may be paired during the amplification (Coronella et al. 2000 Nucleic Acids Res. 28: E85; Babcook et al 1996 PNAS 93: 7843-7848 and WO 05/042774). An alternative approach involves in-cell amplification and pairing of the $V_H$ and $V_L$ encoding sequences (Embleton et al. 1992. Nucleic Acids Res. 20: 3831-3837; Chapal et al. 1997 BioTechniques 23: 518-524). In order to obtain a repertoire of $V_H$ and $V_L$ encoding sequence pairs which resemble the diversity of $V_H$ and $V_L$ sequence pairs in the donor, a high-throughput method with as little scrambling (random combination) of the $V_H$ and $V_L$ pairs as possible, is preferred, e.g. as described in WO 05/042774 (hereby incorporated by reference).

In a preferred embodiment of the present invention a repertoire of $V_H$ and $V_L$ coding pairs, where the member pairs mirror the gene pairs responsible for the humeral immune response upon challenge with an orthopoxvirus, is generated according to a method comprising the steps i) providing a lymphocyte-containing cell fraction from a donor vaccinated with an orthopoxvirus or recovering from an orthopoxvirus infection; ii) optionally enriching B cells or plasma cells from said cell fraction; iii) obtaining a population of isolated single cells, comprising distributing cells from said cell fraction individually into a plurality of vessels; iv) amplifying and effecting linkage of the $V_H$ and $V_L$ coding pairs, in a multiplex overlap extension RT-PCR procedure, using a template derived from said isolated single cells and v) optionally performing a nested PCR of the linked $V_H$ and $V_L$ coding pairs. Preferably the isolated cognate $V_H$ and $V_L$ coding pairs are subjected to a screening procedure as described below.

Once the $V_H$ and $V_L$ sequence pairs have been generated a screening procedure to identify sequences encoding $V_H$ and $V_L$ pairs with binding reactivity towards an orthopoxvirus associated antigen is performed. If the $V_H$ and $V_L$ sequence pairs are combinatorial a phage display procedure can be applied to enrich for $V_H$ and $V_L$ pairs coding for antibody fragments binding to orthopoxvirus prior to screening.

In order to mirror the diversity, affinity and specificity of the antibodies produced in a humeral immune response upon challenge with an orthopoxvirus, the present invention has developed a screening procedure for the cognate pairs, in order to obtain the broadest diversity possible. For screening purposes the repertoire of cognate $V_H$ and $V_L$ coding pairs are expressed individually either as antibody fragments (e.g. scFv or Fab) or as full-length antibodies using either a bacterial or mammalian screening vector transfected into a suitable host cell. The repertoire of Fabs/antibodies is first screened for reactivity to one or more orthopoxvirus strains. In parallel the Fabs/antibodies, are screened against selected antigens. These antigens are selected based on the knowledge of the orthopoxvirus biology and the expected neutralizing and/or protective effect antibodies capable of binding to these antigens potentially can provide. This screening procedure can likewise be applied to a combinatorial phage display library.

Figure 6:
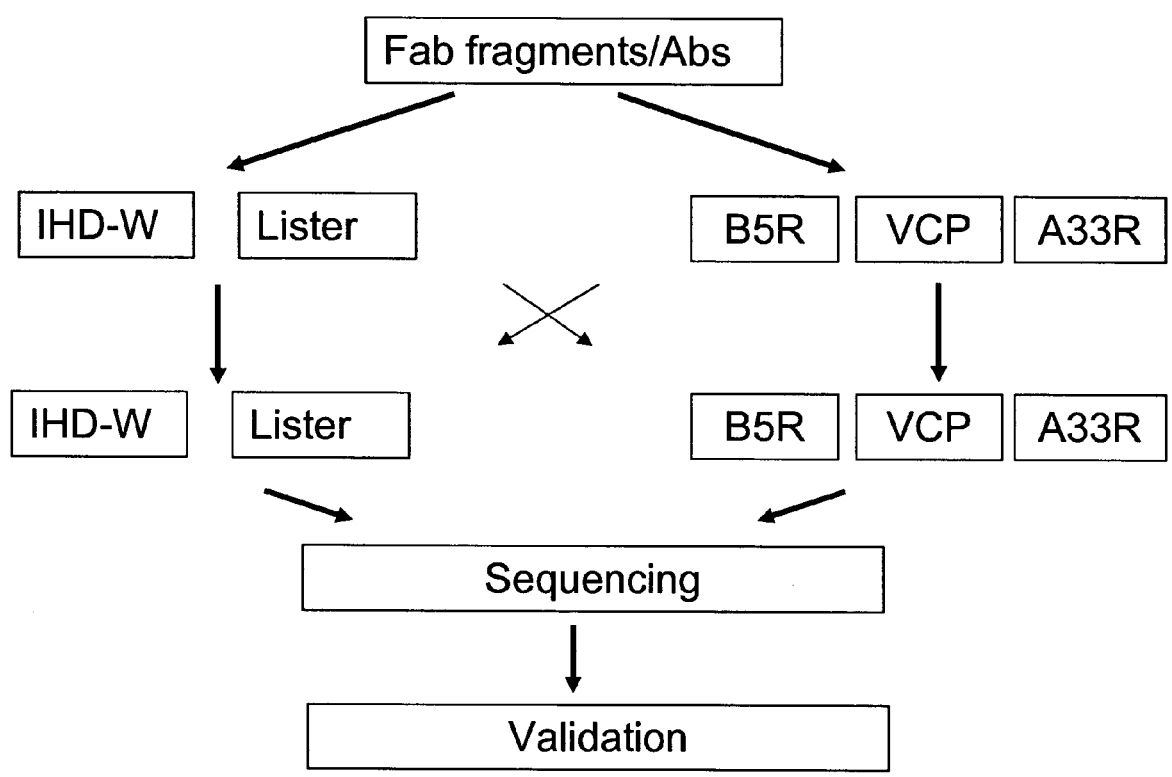
Figure 9:
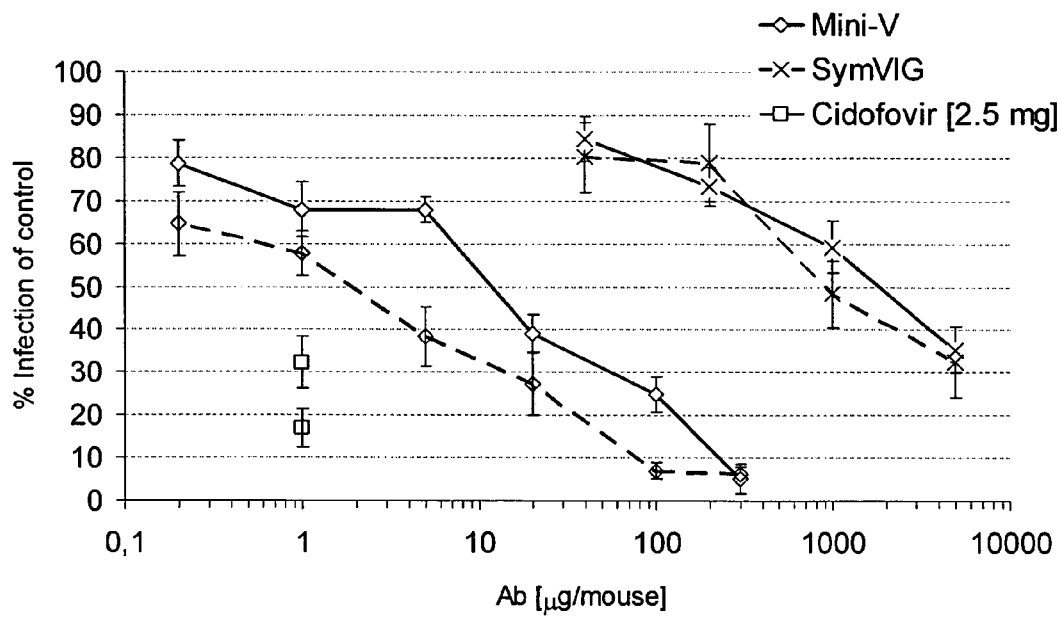
FIG. 9: In vivo inhibition of vaccinia virus replication by Mini-V in the mouse tail lesion vaccinia virus replication model. The indicated amount of Mini-V or SymVIG was injected intraperitoneally 24 hours after viral challenge. Either the Lister strain (dashed) or the NYCBOH strain (solid) was used for challenge. Results are percentages of lesions compared with the control group treated with an irrelevant recombinant polyclonal antibody (anti-RhD rpAb). The small molecule drug Cidofovir was included as positive control and administered intramuscularly (i.m.).
Figure 10:
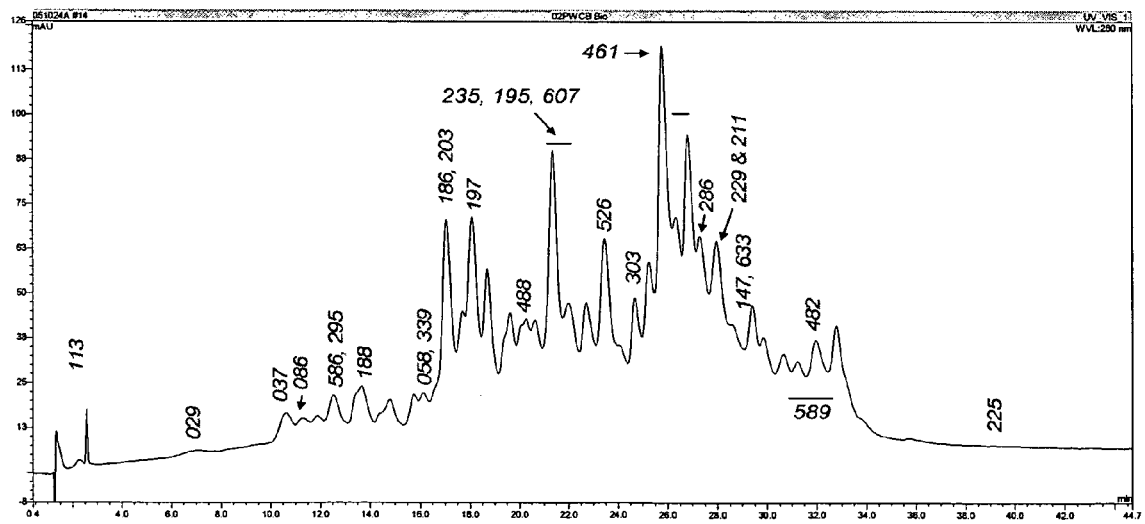
FIG. 10: IEX profile of anti-VV rpAb compound. The individual clones identified by the clone numbers given in Table 5 are assigned to the individual peaks. Cell lines expressing 02-113 and 02-225 were included in the polyclonal cell line but were not found in the anti-VV rpAb.

In an embodiment of the present invention the screening procedure for selecting $V_H$ and $V_L$ sequence pairs capable of encoding a broad diversity of anti-orthopoxvirus antibodies is performed as follows: an antibody or antibody fragments is expressed from a host cell transfected with a screening vector containing a distinct member of the repertoire of $V_H$ and $V_L$ coding pairs. The antibody or antibody fragment is screened against at least two different vaccinia virus strains in conjunction with a parallel screening against one or more of the following antigens A27L, A17L, D8L, H3L, L1R, A33R, B5R and VCP by contacting the antibody or fragment with these strains/antigens. This process is performed for each member of the repertoire of $V_H$ and $V_L$ coding pairs, and sequences encoding $V_H$ and $V_L$ pairs that bind to either the whole virus and/or one of the specific antigens are selected from the host cells containing them (also termed clones). Preferably a second screening is performed, in order to ensure that none of the selected sequences encode false positives. In the second screening all the vaccinia virus/antigen binding $V_H$ and $V_L$ pairs identified in the first screening are screened again against both the virus strains and the selected antigens. The screening procedure is illustrated in FIG. 6, exemplified with some of the antigens mentioned above. Generally, immunological assays are suitable for the screening performed in the present invention. Such assays are well know in the art and constitute for example ELISPOTS, ELISA, FLISA, membrane assays (e.g. Western blots), arrays on filters, and FACS. The assays can either be performed without any prior enrichment steps, utilizing polypeptides produced from the sequences encoding the $V_H$ and $V_L$ pairs. In the event that the repertoire of $V_H$ and $V_L$ coding pairs are cognate pairs no enrichment by e.g. phage display is needed prior to the screening. However, in the screening of combinatorial libraries, the immunoassays is preferably performed in combination with or following enrichment methods such as phage display, ribosome display, bacterial surface display, yeast display, eukaryotic virus display, RNA display or covalent display (reviewed in FitzGerald, K., 2000. Drug Discov. Today 5, 253-258).

The $V_H$ and $V_L$ pair encoding sequences selected in the screening are generally subjected to sequencing, and analyzed with respect to diversity of the variable regions. In particular the diversity in the CDR regions is of interest, but also the $V_H$ and $V_L$ family representation is of interest. Based on these analyses, sequences encoding $V_H$ and $V_L$ pairs representing the overall diversity of the orthopoxvirus binding antibodies isolated from one or more donors are selected. Preferably, sequences with differences in all the CDR regions (CDRH1, CDRH2, CDRH3 and CDRL1, CDRL2 and CDRL3) are selected. If there are sequences with one or more identical or very similar CDR regions which belong to different $V_H$ or $V_L$ families, these are also selected. The selection of $V_H$ and $V_L$ sequence pairs can also be performed based on the diversity of the CDR3 region of the variable heavy chain. During the priming and amplification of the sequences, mutations may occur in the framework regions of the variable region. Preferably, such errors are corrected in order to ensure that the sequences correspond completely to those of the donor, e.g. such that the sequences are completely human in all conserved regions such as the framework regions of the variable region.

When it is ensured that the overall diversity of the collection of selected sequences encoding $V_H$ and $V_L$ pairs is highly representative of the diversity seen at the genetic level in a humeral response to an orthopoxvirus challenge, it is expected that the overall specificity of antibodies expressed from a collection of selected $V_H$ and $V_L$ coding pairs, also are representative with respect to the specificity of the antibodies produced in the challenged donors. An indication of whether the specificity of the antibodies expressed from a collection of selected $V_H$ and $V_L$ coding pairs, are representative of the specificity of the antibodies raised by challenged donors can be obtained by comparing the antibody titers towards the virus strains as well as the selected antigens of the donor blood with the specificity of the antibodies expressed from a collection of selected $V_H$ and $V_L$ coding pairs. Additionally, the specificity of the antibodies expressed from a collection of selected $V_H$ and $V_L$ coding pairs can be analyzed further. The degree of specificity correlates with the number of different antigens towards which binding reactivity can be detected. In a further embodiment of the present invention the specificity of the individual antibodies expressed from a collection of selected $V_H$ and $V_L$ coding pairs are analyzed by Western blot. Briefly, the antigens from an orthopoxvirus strain are resolved on polyacrylamide gel, under reducing conditions. The antibodies are analyzed individually in a Western blot procedure, identifying the protein antigens to which they bind. The binding pattern of the individual antibodies is analyzed and compared to the other antibodies expressed from a collection of selected $V_H$ and $V_L$ coding pairs. Preferably, individual members to be comprised in an anti-orthopoxvirus rpAb of the present invention are selected such that the specificity of the antibody composition collectively covers all the antigens which have produced significant antibody titers in a serum sample from the donor(s). Even more preferred, anti- bodies with different binding pattern in the Western blot analysis are selected to constitute an anti-orthopoxvirus rpAb of the present invention.

Production of a Recombinant Polyclonal Antibody from Selected $V_H$ and $V_L$ Coding Pairs A polyclonal antibody of the present invention is produced from a polyclonal expression cell line in one or a few bioreactors or equivalents thereof. Following this approach the anti-orthopoxvirus rpAb can be purified from the reactor as a single preparation without having to separate the individual members constituting the anti-orthopoxvirus rpAb during the process. If the polyclonal antibody is produced in more than one bioreactor, the supernatants from each bioreactor can be pooled prior to the purification, or the purified anti-orthopoxvirus rpAb can be obtained by pooling the antibodies obtained from individually purified supernatants from each bioreactor.

One way of producing a recombinant polyclonal antibody is described in WO 04/061104 and PCT/DK2005/000501 (these references are hereby incorporated by reference). The method described therein, is based on site-specific integration of the antibody coding sequence into the genome of the individual host cells, ensuring that the $V_H$ and $V_L$ protein chains are maintained in their original pairing during production. Further, the site-specific integration minimizes position effects and therefore the growth and expression properties of the individual cells in the polyclonal cell line are expected to be very similar. Generally, the method involves the following: i) a host cell with one or more recombinase recognition sites; ii) an expression vector with at least one recombinase recognition site compatible with that of the host cell; iii) generation of a collection of expression vectors by transferring the selected $V_H$ and $V_L$ coding pairs from the screening vector to an expression vector such that a full-length antibody or antibody fragment can be expressed from the vector; iv) transfection of the host cell with the collection of expression vectors and a vector coding for a recombinase capable of combining the recombinase recognition sites in the genome of the host cell with that in the vector; v) obtaining/generating a polyclonal cell line from the transfected host cell and vi) expressing and collecting the polyclonal antibody from the polyclonal cell line.

Preferably mammalian cells such as CHO cells, COS cells, BHK cells, myeloma cells (e.g., Sp2/0 or NS0 cells), fibroblasts such as NIH 3T3, and immortalized human cells, such as HeLa cells, HEK 293 cells, or PER.C6, are used. However, non-mammalian eukaryotic or prokaryotic cells, such as plant cells, insect cells, yeast cells, fingi, E. coli etc., can also be employed. A suitable host cell comprises one or more suitable recombinase recognition sites in its genome. The host cell should also contain a mode of selection which is operably linked to the integration site, in order to be able to select for integrants, (i.e., cells having an integrated copy of an anti-orthopoxvirus Ab expression vector or expression vector fragment in the integration site). The preparation of cells having an FRT site at a pre-determined location in the genome was described in e.g. U.S. Pat. No. 5,677,177. Preferably, a host cell only has a single integration site, which is located at a site allowing for high expression of the integrant (a hot-spot).

A suitable expression vector comprises a recombination recognition site matching the recombinase recognition site(s) of the host cell. Preferably the recombinase recognition site is linked to a suitable selection gene different from the selection gene used for construction of the host cell. Selection genes are well known in the art, and include glutamine synthetase gene (GS) and neomycin. The vector may also contain two different recombinase recognition sites to allow for recombinase-mediated cassette exchange (RMCE) of the antibody coding sequence instead of complete integration of the vector. RMCE is described in Langer et al 2002, Nucleic Acids Res. 30, 3067-3077; Schlake and Bode 1994, Biochemistry 33, 12746-12751 and Belteki et al 2003, Nat. biotech. 21, 321-324. Suitable recombinase recognition sites are well known in the art, and include FRT, 10× and attP/attB sites. Preferably the integrating vector is an isotype-encoding vector, where the constant regions (preferably including introns) are present in the vector prior to transfer of the $V_H$ and $V_L$ coding pair from the screening vector. The constant regions present in the vector can either be the entire heavy chain constant region ($CH_1$ to $CH_3$ or to $CH_4$) or the constant region encoding the Fc part of the antibody ($CH_2$ to $CH_3$ or to $CH_4$). The light chain Kappa or Lambda constant region may also be present prior to transfer. The choice of the number of constant regions present, if any, depends on the screening and transfer system used. The heavy chain constant regions can be selected from the isotypes IgG1, IgG2, IgG3, IgG4, IgA1, IgA2, IgM, IgD and IgE. Preferred isotypes are IgG1 and/or IgG3. Further, the expression vector for site-specific integration of the anti-orthopoxvirus antibody coding nucleic acid contains suitable promoters or equivalent sequences directing high levels of expression of each of the $V_H$ and $V_L$ chains. FIG. 4 illustrates one possible way to design the expression vector, although numerous other designs are possible.

The transfer of the selected $V_H$ and $V_L$ coding pairs from the screening vector can be performed by conventional restriction enzyme cleavage and ligation, such that each expression vector molecule contain one $V_H$ and $V_L$ coding pair. Preferably, the $V_H$ and $V_L$ coding pairs are transferred individually, they may, however, also be transferred in-mass if desired. When all the selected $V_H$ and $V_L$ coding pairs are transferred to the expression vector a collection or a library of expression vectors is obtained. Alternative ways of transfer may also be used if desired.

Methods for transfecting a nucleic acid sequence into a host cell are known in the art. To ensure site-specific integration a suitable recombinase must be provided to the host cell as well. This is preferably assured by co-transfection of a plasmid encoding the recombinase. Suitable recombinases are for example Flp, Cre or phage ΦC31 integrase, when used together with a host cell/vector system with the corresponding recombinase recognition sites. The host cell can either be transfected in bulk, meaning that the library of expression vectors is transfected into the cell line in one single reaction thereby obtaining a polyclonal cell line. Alternatively, the collection of expression vectors can be transfected individually into the host cell, thereby generating a collection of individual cell lines (producing monoclonal antibodies). The cell lines generated upon transfection (monoclonal or polyclonal) are then selected for site specific integrants, and adapted to grow in suspension and serum free media, if they did not already do this prior to transfection. If the transfection was performed individually, the individual cell lines are analyzed further with respect to their grow properties and antibody production. Preferably cell lines with similar proliferation rates and antibody expression levels are selected for the generation of the polyclonal cell line. The polyclonal cell line is then generated by mixing the individual cell lines in a predefined ratio. Generally, a polyclonal master cell bank (pMCB) and/or a polyclonal working cell bank (PWCB) is laid down from the polyclonal cell line.

One embodiment of the present invention is a polyclonal cell line capable of expressing a recombinant polyclonal anti-orthopoxvirus antibody of the present invention.

A further embodiment of the present invention is a polyclonal cell line wherein each individual cell is capable of expressing a single $V_H$ and $V_L$ coding pair, and the polyclonal cell line as a whole is capable of expressing a collection of $V_H$ and $V_L$ coding pairs, where each $V_H$ and $V_L$ coding pair encode an anti-orthopoxvirus antibody of the present invention. Preferably the collection of $V_H$ and $V_L$ coding pairs are cognate pairs generated according to the methods of the present invention.

The recombinant polyclonal antibody is then expressed by culturing one ampoule from the pWCB in an appropriate medium for a period of time allowing for sufficient expression of antibody and where the polyclonal cell line remains stable (The window is approximately between 15 days and 50 days). Culturing methods such as fed batch or perfusion may be used. The recombinant polyclonal antibody is obtained from the culture medium and purified by conventional purification techniques. Affinity chromatography combined with subsequent purification steps such as ion-exchange chromatography, hydrophobic interactions and gel filtration has frequently been used for the purification of IgG. Following purification, the presence of all the individual members in the polyclonal antibody composition is assessed, for example by ion-exchange chromatography. The characterization of a polyclonal antibody composition is described in detail in PCT/DK2005/000504 (hereby incorporated by reference).

An alternatively method of expressing a mixture of antibodies in a recombinant host is described in WO 04/009618, this method produces antibodies with different heavy chains associated with the same light chain from a single cell line. This approach may be applicable if the anti-orthopoxvirus rpAb is produced from a combinatorial library.

Therapeutic Compositions

Another aspect of the invention is a pharmaceutical composition comprising as an active ingredient anti-orthopoxvirus rpAb or anti-orthopoxvirus recombinant polyclonal Fab or another anti-orthopoxvirus recombinant polyclonal fragment. Preferably, the active ingredient of such a composition is an anti-orthopoxvirus recombinant polyclonal antibody as claimed by the present invention. Such compositions are intended for prevention, and treatment of adverse effects of vaccination with vaccinia virus or treatment of orthopoxvirus infections, in particular infections with variola virus or monkeypoxvirus. Preferably, the treatment is administered to a human a domestic animal or a pet.

The pharmaceutical composition further comprises a pharmaceutically acceptable excipient.

In further embodiments of the present invention, any of the previously described anti-orthopoxvirus Ab compositions (polyclonal or monoclonal) may additionally be combined with other compositions for the treatment of an orthopoxvirus infection, such as Cidofovir, STI-571 (Reeves et al. 2005, Nature Med. 11:731-739) and/or ST-246 (Yang et al. 2005, J. Virol. 79:13139-13149).

Anti-orthopoxvirus rpAb or polyclonal fragments thereof may be administered within a pharmaceutically-acceptable diluent, carrier, or excipient, in unit dose form. Conventional pharmaceutical practice may be employed to provide suitable formulations or compositions to administer to individuals being vaccinated with an orthopoxvirus or patients showing adverse effects following vaccination or patients infected with an orthopoxvirus. In a preferred embodiment the administration is prophylactic. Any appropriate route of administration may be employed, for example, administration may be parenteral, intravenous, intra-arterial, subcutaneous, intramuscular, intraperitoneal, intranasal, aerosol, suppository, or oral administration. For example, therapeutic formulations may be in the form of, liquid solutions or suspensions; for oral administration, formulations may be in the form of tablets or capsules chewing gum or pasta, and for intranasal formulations, in the form of powders, nasal drops, or aerosols.

The pharmaceutical compositions of the present invention are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (20th ed.), ed. A. R. Gennaro, 2000, Lippincott Williams & Wilkins, Philadelphia, Pa. and Encyclopedia of Pharmaceutical Technology, eds. J. Swarbrick and J. C. Boylan, 1988-1999, Marcel Dekker, New York, N.Y.).

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, pills, or capsules, which may be coated with shellac, sugar or both. It is also possible for them to be incorporated into plastics carriers that allow the active ingredients to diffuse or be released in measured amounts.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

Therapeutic Uses of the Compositions According to the Invention

The pharmaceutical compositions according to the present invention may be used for the treatment, amelioration or prophylaxis of a disease in a mammal. Conditions that can be treated or prevented with the present pharmaceutical compositions include prevention, and treatment of adverse effects of vaccination with vaccinia virus or other orthopoxvirus and treatment of individuals infected with an orthopoxvirus, in particular variola virus, monkeypox virus and camelpox virus infections.

One embodiment of the present invention is a method for treatment or prophylaxis of an orthopoxvirus infection in a human or animal, wherein an effective amount of an anti-orthopoxvirus recombinant polyclonal of the present invention is administered to said human or animal.

A further embodiment of the present invention is a method for treatment, or prevention of adverse side effects of vaccination with vaccinia virus in a human or an animal, wherein an effective amount of an anti-orthopoxvirus recombinant polyclonal of the present invention administered to said human or animal.

A further embodiment of the present invention is the use of an anti-orthopoxvirus recombinant polyclonal antibody of the present invention for the preparation of a composition for the treatment, or prevention of adverse side effects of vaccination with vaccinia virus, or for treatment or prophylaxis of orthopoxvirus infections.

Diagnostic Use and Environmental Detection Use

Another embodiment of the invention is directed to diagnostic kits. Kits according to the present invention comprise an anti-orthopoxvirus rpAb prepared according to the invention which protein may be labeled with a detectable label or non-labeled for non-label detection. The kit may be used to identify individuals infected with orthopoxvirus.

EXAMPLES

Example 1

This example is a collection of the methods applied to illustrate the present invention.

a. Sorting of Plasma Cells from Donor Blood

The peripheral blood mononuclear cells (PBMC) were isolated from blood drawn from donors using Lymphoprep (Axis Shield) and gradient centrifugation according to the manufactures instructions. The isolated PBMC were either cryopreserved in FCS; 10% DMSO at −150° C. or used directly. The B cell fraction was labeled with anti-CD19 antibody and isolated from the PBMC fraction using magnetic cell sorting (MACS). The PBMC ($1\times10^6$ cells) were incubated with anti-CD19-FITC conjugated antibody (BD Pharmingen) for 20 minutes at 4° C. Cells were washed twice in, and resuspended in MACS buffer (Miltenyi Biotec). Anti-FITC MicroBeads (Miltenyi Biotec) were mixed with the labeled cells and incubated for 15 minutes at 4° C. The washing procedure was repeated before the cell-bead suspension was applied to a LS MACS column (Miltenyi Biotec). The CD19 positive cell fraction was eluted from the column according to the manufactures instructions and either stored in FCS-10% DMSO, or proceeded directly to single cell sorting.

Plasma blasts or circulating plasma cells (hereafter plasma cells) were selected from the CD19$^+$ B cell fraction by fluorescence activated cell sorting (FACS) based on the expression profile of CD19, CD38, and CD45 cell surface proteins.

CD19 is a B-cell marker that is also expressed on early plasma cells, while CD38 is highly expressed on plasma cells. The plasma cells apparently, have a somewhat lower expression of CD45 than the rest of the CD19+ cells, which allow separation of a discrete population. The MACS purified cells were thawed or used directly. The cells were washed in FACS buffer (PBS; 1% BSA) and stained for 20 minute with CD19-FITC, CD38-PE, CD45-PerCP (BD Pharmingen). The cells were washed and re-suspended in FACS buffer.

The flow rate of the cells during the FACS was set at 200 events/sec and the cell concentration was $5 \times 10^5$/ml to obtain a high plasma cells rescue. The following set of gates, were used. Each gate is a daughter of the former.

Gate 1: FSC/SSC gate. The lymphocyte population having the highest FSC is selected ensuring sorting of living cells.
Gate 2: SSCh/SSCw. This gate ensures sorting of single cells.
Gate 3: CD19+ cells. In the FL1-FL2 dot plot, only the CD19 positive cells are selected.
Gate 4: In the FL2-FL3 dot plot, a discrete population should be visible, which is CD38high and CD45intermediate.

The resulting population that fulfills these four criteria was single-cell sorted into 96-well PCR plates containing a sorting buffer (see section c). The cell containing plates were stored at −80° C.

b. ELISpot

ELISpot was used to estimate the percentages of plasma cells expressing anti-vaccinia virus antibodies in obtained cell samples i.e. PBMC, MACS purified CD19+ cells, or a population of FACS sorted plasma cells. 96-well plates with a nitrocellulose surface (Millipore) were coated with a solution of 20 µg/ml inactivated vaccinia virus particles of either Lister strain of IHD-W strain (AutogenBioclear, UK). The wells were blocked by incubation with RPMI, 10% FCS at 4° C. over night. The plasma cell containing cell sample was added in RPMI culture medium to each well followed by incubation at standard tissue culture conditions for 24 hours. The secreted vaccinia virus specific antibodies will bind to the immobilized virus particles surrounding the antibody producing plasma cell. The cells were removed by washing three times in PBS; 0.01% Tween20 and three times in PBS. HRP-conjugated anti-human IgG (H+L) (CalTag) and HRP-conjugated anti-human IgA (SeroTech) were added and allowed to react with the immobilized antibodies for 1 hour at 37° C. The washing procedure was repeated and the chromogen substrate (3-amino-9-ethylcarbazole solubilized in N,N-DMF (di-methyl formamide) was added. The color development was terminated after 4 minutes by addition of $H_2O$. Red spots were identified at the sites where antigen specific plasma cells had been located.

c. Linkage of Cognate $V_H$ and $V_L$ Pairs

The linkage of $V_H$ and $V_L$ coding sequences was performed on the single cells obtained as described in section a), facilitating cognate pairing of the $V_H$ and $V_L$ coding sequences. The procedure was a two step PCR procedure based on a one-step multiplex overlap-extension RT-PCR followed by a nested PCR. The primer mixes used in the present example only amplify Kappa light chains. Primers capable of amplifying Lambda light chains could, however, be added to the multiplex primer mix and nested PCR primer mix if desired. The principle is illustrated in FIG. 2.

The 96-well PCR plates from produced in step a) were thawed. The single cell served as template for the multiplex overlap-extension RT-PCR. Sorting buffer containing reaction buffer (Phusion HF buffer; Finnzymes), primers for RT-PCR (see Table 2) and RNase inhibitor (RNasin, Promega) was already added to each well before the single-cell sorting. The following was added to each well to obtain the given final concentration: dNTP mix (200 µM each), RNAse inhibitor (20 U/µl), Sensiscript Reverse Transcriptase (320× dilution; Qiagen) and Phusion DNA Polymerase (0.4 U; Finnzymes).

The plates were incubated for 1 hour at 37° C. to allow reverse transcription of the RNA from each cell. Following the RT, the plates were subjected to the following PCR cycle: 30 sec. at 98° C., 30×(20 sec. at 98° C., 30 sec. at 60° C., 45 sec. at 72° C.), 45 sec. at 72° C.

The PCR reactions were performed in H20BIT Thermal cycler with Peel Seal Basket for 24×96-well plates (ABgene), to facilitate a high-throughput. The PCR plates were stored at −20° C. after cycling.

TABLE 2

RT-PCR multiplex overlap-extension primer mix

| Primer name | Final Conc. µM | Sequence | SEQ ID |
|---|---|---|---|
| VH set | | | |
| CH-IgG | 0.2 | GACSGATGGGCCCTTGGTGG | |
| CH-IgA | 0.2 | GAGTGGCTCCTGGGGAAGA | |
| VH-1 | 0.04 | TATTCCCATGGCGCGCCCAG RTGCAGCTGGTGCART | |
| VH-2 | 0.04 | TATTCCCATGGCGCGCCSAG GTCCAGCTGGTRCAGT | |
| VH-3 | 0.04 | TATTCCCATGGCGCGCCCAG RTCACCTTGAAGGAGT | |
| VH-4 | 0.04 | TATTCCCATGGCGCGCCSAG GTGCAGCTGGTGGAG | |
| VH-5 | 0.04 | TATTCCCATGGCGCGCCCAG GTGCAGCTACAGCAGT | |
| VH-6 | 0.04 | TATTCCCATGGCGCGCCCAG STGCAGCTGCAGGAGT | |
| VH-7 | 0.04 | TATTCCCATGGCGCGCCGAR GTGCAGCTGGTGCAGT | |
| VH-8 | 0.04 | TATTCCCATGGCGCGCCCAG GTACAGCTGCAGCAGTC | |
| LC set | | | |
| CK1 | 0.2 | ATATATATGCGGCCGCTTAT TAACACTCTCCCCTGTTG | |
| VL-1 | 0.04 | GGCGCGCCATGGGAATAGCT AGCCGACATCCAGWTGACCC AGTCT | |
| VL-2 | 0.04 | GGCGCGCCATGGGAATAGCT AGCCGATGTTGTGATGACTC AGTCT | |
| VL-3 | 0.04 | GGCGCGCCATGGGAATAGCT AGCCGAAATTGTGWTGACRC AGTCT | |
| VL-4 | 0.04 | GGCGCGCCATGGGAATAGCT AGCCGATATTGTGATGACCC ACACT | |
| VL-5 | 0.04 | GGCGCGCCATGGGAATAGCT AGCCGAAACGACACTCACGC AGT | |

TABLE 2-continued

RT-PCR multiplex overlap-extension primer mix

| Primer name | Final Conc. µM | Sequence | SEQ ID |
|---|---|---|---|
| VL-6 | 0.04 | GGCGCGCCATGGGAATAGCT AGCCGAAATTGTGCTGACTC AGTCT | |

W = A/T, R = A/G, S = G/C

For the nested PCR step, 96-well PCR plates were prepared with the following mixture in each well to obtain the given final concentration: 1× FastStart buffer (Roche), dNTP mix (200 µM each), nested primer mix (see Table 3), Phusion DNA Polymerase (0.08 U, Finnzymes) and FastStart High Fidelity Enzyme blend (0.8 U; Roche). As template for the nested PCR, 1 µl was transferred from the multiplex overlap-extension PCR reactions. The nested PCR plates were subjected to the following PCR cycle: 35×(30 sec. at 95° C., 30 sec. at 60° C., 90 sec. at 72° C.), 600 sec. at 72° C.

Selected reactions were analyzed on a 1% agarose gel to verify the presence of an overlap-extension fragment of approximately 1070 bp.

The plates were stored at −20° C. until further processing of the PCR fragments.

TABLE 3

Nested primer set

| Primer name | Final Conc. µM | Sequence | SEQ ID |
|---|---|---|---|
| CK2 | 0.2 | ACCGCCTCCACCGGCGGCCGCTTATTAACA CTCTCCCCTGTTGAAGCTCTT | |
| PJ 1-2 | 0.2 | GGAGGCGCTCGAGACGGTGACCAGGGTGCC | |
| PJ 3 | 0.2 | GGAGGCGCTCGAGACGGTGACCATTGTCCC | |
| PJ 4-5 | 0.2 | GGAGGCGCTCGAGACGGTGACCAGGGTTCC | |
| PJ 6 | 0.2 | GGAGGCGCTCGAGACGGTGACCGTGGTCCC | | d. Insertion of cognate VH and VL coding pairs into a screening vector

In order to identify antibodies with binding specificity to vaccinia virus particles, the $V_H$ and $V_L$ coding sequences were expressed either as Fabs or full-length antibodies. This involved insertion of the repertoire of $V_H$ and $V_L$ coding pairs into a screening vector and transformation into a host cell.

A two-step cloning procedure was employed for generation of a repertoire of screening vectors containing the $V_H$ and $V_L$ coding pairs. Statistically, if the repertoire of screening vectors contain ten times as many recombinant plasmids as the number of cognate paired $V_H$ and $V_L$ PCR products used for generation of the screening repertoire, there is 99% likelihood that all unique gene pairs are represented. Thus, if 400 overlap-extension V-gene fragments were obtained in section c) a repertoire of at least 4000 clones was generated for screening.

Briefly, the repertoire of linked $V_H$ and $V_L$ coding pairs from the nested PCR in section c) were pooled (without mixing pairs from different donors). The PCR fragments were cleaved with XhoI and NotI DNA endonucleases at the recognition sites introduced into the termini of PCR products. The cleaved and purified fragments were ligated into an XhoI/NotI digested Fab-expression vector by standard ligation procedures. Suitable vectors were for example the bacterial or mammalian expression vectors illustrated in FIG. 3. The ligation mix was electroporated into E. coli and added to 2×YT plates containing the appropriated antibiotic and incubated at 37° C. over night. The amplified repertoire of vectors was purified from cells recovered from the plates using standard DNA purification methods (Qiagen). The plasmids were prepared for insertion of promoter-leader fragments by cleavage using AscI and NheI endonucleases. The restriction sites for these enzymes were located between the $V_H$ and $V_L$ coding gene pairs. Following purification of the vector, an AscI-NheI digested bi-directional promoter-leader fragment was inserted into the AscI and NheI restriction sites by standard ligation procedures. The ligated vector was amplified in E. coli and the plasmid was purified using standard methods. Where a bacterial screening vector was used the bi-directional promoters were bacterial promoters, and where the mammalian screening vector was used the bi-directional promoters were mammalian promoters. The generated repertoire of screening vectors was transformed into E. coli for by conventional procedures. Colonies obtained were consolidated into 384-well master plates and stored. The number of arrayed colonies exceeded the number of input PCR products by at least 3 fold, thus giving 95% percent likelihood for presence of all unique V-gene pairs obtained in section c).

e. Screening

The screening strategy is presented in FIG. 6. Fab expression was performed by inoculation of the colonies from the master plate into a 384-well plate. In cases where Fab expression was performed from E. coli the plates contained 0.9 ml 2×YT, 0.1% glucose, 50 µg/ml Carbencilin and the colonies were incubated with vigorous shaking at 37° C. until the cell density detected as OD600 reached ~1. The Fab expression was induced by addition of 0.1 ml 2×YT, 0.1 M IPTG, 50 µg/ml Carbenicillin and the temperature decreased to 30° C. The Fab-containing supernatants were cleared by centrifugation and stored for screening reactions. The Fab-containing supernatants were cleared by centrifugation and stored for screening reactions. In cases where Fab expression was performed from mammalian vectors, DNA for transfection was prepared from the E. coli master plates. CHO cells were seeded into 384-well cell culture plates (3000 cells per well) in F12-HAM medium with 10% fetal calf serum (FCS) and after an overnight incubation the cells were transfected with the DNA using Fugene 6 as transfection agent. After 2-3 days in cell culture the Fab-containing supernatants were harvested and stored for screening reactions.

Screening of individual clones was performed using a fluorescence-linked immunosorbent assay (FLISA) based on the fluorometric microvolume assay technology (FMAT) (Swartzman et al. 1999, Anal. Biochem. 271:143-151). Briefly, inactivated virus particles of the Lister strain, IHD-W strain, and the recombinant protein antigens B5R, VCP and A33R were immobilized individually on polystyrene beads (6.79 µm diameter, Spherotech Inc.) by incubating 16.5 µg protein or 20 µg virus particles with 100 µL 5% w/v beads. The supernatant containing Fab-fragments were screened against all five populations of coated beads. The coated beads, a secondary fluorescently-labeled anti-human antibody (Alexa Dye 647, Molecular Probes) and supernatant containing Fab-fragments were mixed in 384-well plates. Wells containing Fabs with reactivity against the coated antigen resulted in an increased fluorescence at the bead surface, which were detected using FLISA reader (8200 Cellular Detection System; Applied Biosystems). In principle, the assay is equivalent to ELISA but since no washing steps are included, the procedure has a high throughput. Cut-off was set at as low as 50 detected fluorescent beads (counts) during the primary screen in order to minimize losses and to identify as many clones reactive with viral particles or antigen as possible. From the original master plates, the primary hits were retrieved and collected in wells of 96-well plates. The generated primary hit plates were handled as master plates, including storage and re-expression of these primary hits. These re-expressed Fab molecules were tested in a secondary screening using the same antigens in both FLISA and standard ELISA. Clones which produced Fabs with reactivity in both FLISA and ELISA in the secondary screen were submitted for DNA sequencing of the V-gene region.

The obtained sequences were aligned based on the amino acid sequence of the CDR3 region and grouped into clusters of clones expressing identical Fabs, some of the clusters only contained a single clone (a singleton). Large scale batches of Fab-fragments of representative clones from each cluster were prepared for validation of the anti-vaccinia virus reactivity. These studies consisted of binding analyses by ELISA using inactivated IHD-W, inactivated IHD-J, inactivated Lister strain VV particles, and the recombinant antigens, A27L, L1R, B5R, VCP, and A33R. Clones producing Fab-fragments which were positive to an inactivated vaccinia virus strain and/or one of the recombinant antigens were termed validated f. Transfer of Selected Clones to Mammalian Expression Vector When using a multiplex PCR approach as described in section c), a certain degree of intra-V-gene family cross-priming and inter-V-gene family cross-priming is expected due to the high degree of homology. The cross-priming introduces non-natural occurring amino acids into the sequences with several potential consequences e.g. structural changes and increased immunogenicity, all resulting in a decreased therapeutic activity.

In order to eliminate these drawbacks and to ensure that selected clones mirror the natural humeral immune response such cross-priming mutations were corrected during the transfer of the $V_H$ and $V_L$ coding pairs (in the form of the complete light chain linked to the variable heavy chain) from the screening vector to the mammalian expression vector. Either all clones, mutations or not, or just the clones with mutations were subjected to the two-step transfer procedure.

In the first step of the repair transfer procedure, the $V_H$ sequence was PCR amplified with a primer set containing the sequence corresponding to the originating $V_H$-gene family thereby reverse mutating any cross-priming introduced changes. The PCR fragment was digested with XhoI and AscI and ligated into the XhoI/AscI digested mammalian expression vector (FIG. 3) using conventional ligation procedures. The ligated vector was amplified in $E. coli$ and the plasmid was purified using standard methods. The $V_H$ sequence was sequenced to verify the correction. The vector was digested with NheI/NotI, to prepare it for insertion of the light chain.

In the second step the complete light chain was PCR amplified with a primer set containing the sequence corresponding to the originating $V_L$-gene thereby reverse mutating any cross-priming changes. The PCR fragment was digested with NheI/NotI and ligated into the $V_H$ containing vector prepared above. The ligation product was amplified in $E. coli$ and the plasmid was purified. The light chain was sequenced to verify the correction.

If clones did not need correction of the $V_H$ and $V_L$ coding pair, they could optionally be transferred directly as a pair in a single step using the XhoI/NheI restriction sites in a conventional cloning procedure. In that event a promoter change was necessary if the screening vector was a bacterial vector. This was performed as described in section d). If the transfer was performed from a mammalian screening vector no promoter exchange was necessary.

g. Generation of a Polyclonal Cell Line

The generation of a polyclonal expression cell line producing a recombinant polyclonal antibody is a multi-step procedure involving the generation of individual expression cell lines (monoclonal cell lines) which each express a unique antibody. The polyclonal cell line is obtained by mixing the individual cell lines thereby generating a polyclonal master cell bank (PMCB) from which a polyclonal working cell bank (PWCB) can be generated simply by continuing amplification.

h. Transfection and Selection of Mammalian Cell Lines

The Flp-In CHO cell line (Invitrogen) was used as starting cell line. In order to obtain a more homogenous cell line the parental Flp-In CHO cell line was sub-cloned by limited dilution and several clones were selected and expanded. Based on growth behavior one clone, CHO-Flp-In (019), was selected as starting cell line. The CHO-Flp-In (019) cells were cultured as adherent cells in F12-HAM with 10% fetal calf serum (FCS).

The individual plasmid preparations each containing a selected $V_H$ and $V_L$ coding pair obtained in step 0), were co-transfected with Flp recombinase encoding plasmid into $5 \times 10^6$ CHO-Flp-In (019) cell line using Fugene6 (Roche) (for further details see WO 04/061104) to generate approximately 10,000 independent recombination events for each transformation. The large-scale transformation procedure was applied as uniformly as possibly to ensure that identical expression cell populations were generated for each $V_H$ and $V_L$ coding pair. Cells were trypsinated after 24 hours and transferred to 3×T175 flasks. Recombinant cell lines were selected by culturing in the presence of 450 µg/ml Neomycin, which was added 48 hours after transfection. Approximately two weeks later clones appeared. Clones were counted and cells were trypsinated and hereafter cultured as pools of clones expressing one of the specific anti-VV antibodies.

i. Adaptation to Serum Free Suspension Culture

The individual adherent anti-VV antibody CHO-Flp-In (019) cell cultures were trypsinated, centrifuged and transferred to separate shaker flasks with $8 \times 10^5$ cells/ml in appropriate serum free medium (Excell302, JRH Biosciences). Growth and cell morphology were followed over several weeks. After 4-6 weeks the cell lines usually showed good and stable growth behavior with doubling times below 32 hours and the adapted individual cell line was cryopreserved as described above.

j. Characterization of Cell Lines

All the individual cell lines were characterized with respect to antibody production and proliferation. This was performed with the following assays:

Production:
The production of recombinant antibodies of the individual expression cell lines were followed during the adaptation by Kappa specific ELISA. ELISA plates were coated overnight with goat-anti-human Kappa antibodies (Caltag) in carbonate buffer, pH 9.6. Plates were washed 6 times with washing buffer (PBS; 0.05% Tween 20) and blocked by incubation for 1 hour in washing buffer containing 2% non fat milk. Cell culture media supernatants were added and the incubated extended for 1 hour. Plates were washed 6 times in washing buffer and secondary antibodies (goat-anti-human IgG (H+L) HRPO, Caltag) were added and the incubation repeated. After vigorous washing the ELISA was developed with TMB substrate and reaction stopped by addition of $H_2SO_4$. Plates were read at 450 nm.

Further, intracellular staining was used to determine the general expression level as well as to determine the homogeneity of the cell population in relation to expression of recombinant antibody. $5 \times 10^5$ cells were washed in cold FACS buffer (PBS; 2% FCS) before fixation by incubation in CellFix (BD-Biosciences) for 20 minutes and hereafter washed in saponin buffer (PBS; 0.2% Saponin). The suspension was centrifuged and fluorescently tagged antibody (Goat F(ab')$_2$ Fragment, Anti-human IgG(H+L)–PE, Beckman Coulter) was added. After 20 minutes on ice the cells were washed twice in saponin buffer and suspended in FACS buffer and analyzed by FACS.

Proliferation:

Aliquots of the cell suspensions were taken three times a week and cell number, cell size, degree of clumping, and viability was determined by CASY® (Cell Counter+Analyzer System from Schärfe System GmbH) analysis. The doubling time for the cell cultures was calculated by cell number derived form CASY® measurements.

k. Characterization of the Antigen Specificity of the Individual Antibodies

The antigen specificity of the individual expressed antibodies was assessed in order to allow the generation of an anti-VV rpAb with a well-characterized specificity. As already described in section e) the antibodies identified during screening were validated by assessing their binding specificity to inactivated vaccinia virus strains and recombinantly produced A27L, L1R, B5R, VCP, and A33R antigens. These analyses were repeated using the full-length antibodies and additional analysis of the antigen specificity was performed by Western blotting.

The vaccinia virus particle associated proteins (antigens) were separated by SDS-PAGE, using acetone precipitated virus particles which subsequently were dissolved in SDS-loading buffer containing 8 M urea and run on a NuPAGE Bis-Tris 4-12% gel or NuPAGE Bis-Tris 10%. This resulted in a clear separation of the vaccinia virus particle associated proteins when visualized by Coomassie blue. For antigen binding analysis, the vaccinia virus particle associated proteins were separated by SDS-PAGE and electroblotted onto a PVDF membrane and purified preparations of the individual antibodies were analyzed by Western blotting. FIG. 5 shows Western blot analyses identifying a series of antigens derived from the Lister strain detected by different antibodies.

Putative target proteins were expressed by in vitro translation and tested for interaction with the selected antibodies by ELISA. The antigen genes were generated by a gene specific PCR using vaccinia virus, lister strain DNA as template (Autogenbioclear, UK Cat. No.: 08-940-250) followed by a second PCR step for addition of T7 promoter and Poly-A sequences. The Phusion DNA polymerase (Finnzymes, F cat. No: F530L) gene specific PCR reactions consisted of total volume at 50 μl containing 0.2 μM of 5' and 3' gene specific oligo pairs as indicated in Table 4, 1× Phusion HF reaction, 0.2 μM of each dNTP and 0.5 μl vaccinia virus DNA, 1 U Phusion DNA polymerase and were cycled through, 1×98° C. 30 seconds, 25×(98° C. for 10 seconds, 50° C. for 15 seconds, 72° C. 20 seconds), 1×72° C. 7 minutes. The T7-Kozak translational initiation and Poly-A sequence were added by a second PCR reaction identical to the above described except for that T7-Koz. Poly-A (Table 4) primers and 0.5 μl of the 1 step PCR reaction were used as template. The PCR products were in vitro translated using the TNT T7 Quick for PCR DNA kit (Promega, USA, Cat. No.: L1170) according to manufacturers procedure. In detail each reaction consists of 40 μl TNT T7 Quick Master Mix, 1 μl mM Methionine 1, 1 μl Transcend Biotin-Lysyl-tRNA (Promega, Cat. No. L5061), 2 μl PCR generated DNA and incubated for 75 minutes at 30° C.

The in vitro translated antigens were tested for interactions with purified antibodies by ELISA performed in standard ELISA. The purified antibodies were immobilized in an ELISA plate and incubated with dilutions of the in vitro translated antigens. Retained antigen was detected by Streptavidin Peroxidase Polymer (Sigma Cat. No.. S-2438) according to standard ELISA procedure similar to the desription in Example 1, section g).

TABLE 4

Primers for generation of in vitro translational antigen genes

| Primer Name | Sequence | SEQ ID |
|---|---|---|
| H3L-5' | GGGAACAGCCACCATGGCG GCGGTGAAAACTCCTGTTA | |
| H3L-3' | GGATCCTCTAGATCATTAA AATGAAATCAGTGGAGTAG TAAAC | |
| A56R-5' | GGGAACAGCCACCATGACA TGACACCTTTTCCTCAGAC ATCT | |
| A56R-3' | GGATCCTCTAGATCATTAA GAGGTTGTACTACTACC TAC | |
| BSR-5' | GGGAACAGCCACCATGACA TGTACTGTACCCACTATGA | |
| B5R-3' | GGATCCTCTAGATCATTAT AACGATTCTATTTCTTG | |
| Poly-A | TTTTTTTTTTTTTTTTTT TTTTTTTTTTGGATCCTC TAGATCATTA | |
| T7-Koz. | GGATCCTAATACGACTCAC TATAGGGAACAGCCACC ATG | |
| A10L-5' | GGGAACAGCCACCATGATG CCTATTAAGTCAATAG | |
| A10L-3 | GGATCCTCTAGATCATTAT TCATCATCAAAAGAG | |
| A3L-5' | GGGAACAGCCACCATGGAA GCCGTGGTCAATAGCGA | |
| A3L-3' | GGATCCTCTAGATCATTAA AATAGTTCTGTAATATGT CTA | |
| A13L-5' | GGGAACAGCCACCATGATT GGTATTCTTTTGTTGAT | |
| A13L-3' | GGATCCTCTAGATCATTAT ACAGAAGATTTAACTAGAT | |
| D8L-5' | GGGAACAGCCACCATGCCG CAACAACTATCTCCT | |

TABLE 4-continued Primers for generation of in vitro translational antigen genes

| Primer Name | Sequence | SEQ ID |
|---|---|---|
| D8L-3' | GGATCCTCTAGATCATTAT TTATTCCCTTCGATATATT TTTGA | |
| A11L-5' | GGGAACAGCCACCATGACG ACCGTACCAGTGACG | |
| A11L-3' | GGATCCTCTAGATCATTAA ATAATTTTAATTCGTTTAA | |
| A17L-5' | GGGAACAGCCACCATGAGT TATTTAAGATATTACAAT | |
| A17L-3' | GGATCCTCTAGATCATTAA TAATCGTCAGTATTTAA ACT | |
| L5R-5' | GGGAACAGCCACCATGGAG AATGTTCCTAATGTA | |
| L5R-3' | GGATCCTCTAGATTATCAT CTGCGAAGAACATCGTTA | |
| F13L-5' | GGGAACAGCCACCATGTGG CCATTTGCATCGGTA | |
| F13L-3' | GGATCCTCTAGATCATTAA ATTTTAACGATTTACTGT | |
| A16L-5' | GGGAACAGCCACCATGATG GGGGCAGCTGTTACTCTT | |
| A16L-3' | GGATCCTCTAGATCATTAA GGCAGTTTTATTTTATCTT TTA | |

1. Characterization of the Biochemical Properties the Individual Antibodies

Heterogeneity is a common phenomenon in antibodies and recombinant proteins. Antibody modifications can occur during expression, through unfavorable storage conditions, and may cause size or charge heterogeneity. Common modifications include N-glycosylation, methionine oxidation, proteolytic fragmentation, and deamidation. Since these parameters need to be well-defined for therapeutic antibodies, they are analyzed prior to the generation of the polyclonal cell line.

The antibodies expressed during adaptation were purified by affinity chromatography (Protein-A columns) with low pH elution, and used for characterization of the biochemical properties of each individual antibody. The methods used for characterization included reducing and non-reducing SDS-PAGE and weak cation exchange chromatography (IEX). Well-defined heavy and light chain bands in the reducing SDS-PAGE indicated intact antibodies. SDS-PAGE analysis of antibody preparations resulting in well-defined bands, were expected to exert a single peak behavior in IEX analysis, indicating a homogeneously antibody preparation. Antibody preparations resulting in multiple peaks in the IEX analysis and/or aberrant migration of either the light or heavy chain in SDS gels were analyzed in detail for intact N-termini by N-terminal sequencing, as well as for the presence of additional N-glycosylation sites in the variable chains using enzymatic treatment.

m. Establishment of a Polyclonal Cell Line for Anti-VV Recombinant Polyclonal Antibody Production Out of the pool of established expression cell lines a subset were selected to constitute the polyclonal expression cell line (pMCB). The selection parameters can be defined according to the use of the polyclonal antibody to be produced from the polyclonal cell line and the performance of the individual cell lines. Generally the following parameters were considered:

Cell line characteristics; to optimize the stability of the polyclonal cell line, individual cell lines with doubling times between 21 and 34 hours and antibody productivity above 1 pg/cell/day.

Antigen reactivity; which antigens should the anti-VV rpAb exert reactivity against, IMV, EEV and/or RCA derived proteins?

Protein chemistry; generally antibodies with well-defined biochemical characteristics were included in the final anti-VV rpAb.

The selected individual cell lines each expressing a recombinant anti-VV antibody were thawed and expanded at 37° C. in serum free medium in shaker flasks to reach at least $4\times10^8$ cells of each clone having a population doubling time of 21-34 hours. The viabilities were in the range of 93% to 96%. The polyclonal cell line was prepared by mixing $2\times10^6$ cells from each cell line. The polyclonal cell line was distributed into freeze ampoules containing $5.6\times10^7$ cells and cryopreserved. This collection of vials with a polyclonal cell line is termed the polyclonal master cell bank (PMCB) from which the polyclonal working cell bank (PWCB) was generated by expanding one ampoule from the pMCB to reach a sufficient number of cells to lay down a polyclonal working cell bank (PWCB) of approximately 200 ampoules with the same cell density as the ampoules of the pMCB. Samples in the cell banks were tested for mycoplasma and sterility.

n. Expression of a Recombinant Polyclonal Anti-VV Antibody

Recombinant polyclonal anti-VV antibody batches were produced in 5 liter bioreactors (B. Braun Biotech International, Melsungen, Germany). Briefly, vials from the pWCB were thawed and expanded in shaker flasks (Corning). Cells in seed train were cultured in ExCell 302 medium with G418 and with anti-clumping agent at 37° C., 5% $CO_2$. The bioreactors were inoculated with $0.6\times10^6$ cells/ml suspended in 3 liter ExCell 302 medium without G418 and without anti-clumping agent. The cell numbers/viable cells were daily monitored by CASY counting. At 50 hours 2000 ml ExCell 302 medium was supplemented and after 92 hours a temperature downshift from 37° C. to 32° C. was performed. The cell culture supernatant was harvested after 164 hours and subjected to purification as described in section o).

o. Purification of Anti-VV rpAb

The antibody expressed as described in section n) was of the IgG1 isotype and affinity purified (Protein-A). The individual antibodies interacted with immobilized Protein A at pH 7.4, whereas contaminating proteins were washed from the column. The bound antibodies were subsequently eluted from the column by lowering of the pH to 2.7. The fractions containing antibodies, determined from absorbance measurements at 280 nm, were pooled and dialyzed against 5 mM sodium acetate, 150 mM NaCl, pH 5 and long time stored at −20° C.

p. In Vitro Neutralization Assays

Preparation of Vaccinia Virus for Use In Vivo and In Vitro
Lister, NYCBOH, and IHD-J vaccinia virus at $10^4$ pfu/ml was added to $10\times175$ cm² flasks of sub-confluent BSC-1 cells in 5 ml of serum-free Gibco Earle's Minimal Essential Medium (MEM). The virus was allowed to adsorb for 45 minutes at 37° C. 30 ml of MEM containing 2% (v/v) Gibco foetal calf serum (FCS) was then added to each flask before returning to 37° C. When the infected cells showed full cytopathic effect, the medium was discarded. The cells were detached from the flasks, by tapping, into 25 ml of PBS. This was centrifuged at 3,000 rpm for 10 minutes at 8° C. The virus containing cell pellet was re-suspended in 6 ml of PBS and frozen at −80° C. Once thawed, the cell debris were removed by centrifugation, 3,000 rpm for 10 minutes at 8° C. Aliquots of the supernatant were frozen at −80° C. Virus was titred by plaque assay.

Plaque Reduction and Neutralisation Assays (PRNT)

The test substances were diluted in serum free MEM and pre-incubated for 1 hour at 37° C. with $10^4$ pfu of Lister strain virus particles. The mixture was applied to a monolayer of Vero cells pre-seeded in 24-well plates. The infected cells were overlayed by addition of 2×MEM including 2% carboxymethylcellulose followed by incubation at 37° C.; 5% CO2 for 3 days. The cells were fixated by incubation with PBS; 10% formalin and stained using 20% Ethanol containing 0.1% crystal violet and the number of plaques in each well was recorded by counting.

The EEV-neutralization assay was performed using a similar protocol except for that IHD-J strain was used and the carboxymethylcellulose overlay was omitted. The IHD-J/Mini-H mixture was pre-incubated with the cells before addition of the Mini-V dilutions and thereby only detection a Mini-V effect on the EEV mediated virus spreading.

q. In Vivo Protection Assays

The mouse tail lesion model was used to analyze the in-vivo protection conferred by an anti-VV antibody composition. The experiments were performed at the Health Protection Agency, Porton Down, UK ("HPA"). In brief, the mice were challenged by injection of infectious vaccinia virus particles of either the Lister or the NYCBOH strain into the tail vein of the mouse. The used amount of virus results in a countable number of virus induced lesions on the tail within seven days. Twenty-four hours after or prior to viral challenge, increasing amounts of test antibody compound Mini-V, SymVIG, Sym002 anti-V rp-Ab or an unrelated polyclonal antibody was injected intraperitoneally (I.P). or intramuscular (I.M). In some of the experiments a total of 2.5 mg Cidofovir was injected intramuscularly (I.M) as a positive control for viral inhibition.

r. Composition of Sym002 Mix

Antibodies for Sym002 mix was purified individually as described in Example 1, section o, and subsequently mixed. The final antibody concentration of Sym002 mix was 1.09 mg/ml and was produced mixing 0.2 mg of each of the antibodies 02-029, 02-058, 02-086, 02-113, 02-147, 02-186, 02-188, 02-195, 02-197, 02-211, 02-225, 02-229, 02-235, 02-286, 02-295, 02-303, 02-339, 02-461, 02-482, 02-488, 02-526, 02-551, 02-586, 02-589, 02-607, 02-633, 0.574 mg of 02-037 and 0.171 mg of 02-203. The antibody identity is given in Table 5.

s. Affinity Measurements of Antibody-Antigen Interactions

Affinities of antibody-antigen interactions were measured by surface plasmon resonance using a Biacore 2000 (Biacore AB). The antigen (B5R, VCP, A33R, or A27L) was immobilized on a CM5 chip surface using standard amine coupling chemistry to a level resulting in a $RU_{max}$ of approximately 100 RU or less. Purified antibody Fab fragments (see section 0) were diluted serially in HBS-EP running-buffer (Biacore AB) and passed over the chip at 10-50 µl/min. Rate constants ($k_{on}$ and $k_{off}$) and affinity constants ($K_D$) were determined using the BIAevaluation software (Biacore AB) by global fitting of four to six different concentrations passed over the same sensor surface.

t. Preparation of Fab Fragment by Papain Digestion of Purified Antibodies

Fab fragments were produced from purified antibodies by using the ImmunoPure Fab preparation Kit (Pierce, USA cat. No.: 44885) according to manufactures instructions. Briefly, 1.2 mg of the antibodies subject for Papain cleavage were dialyzed against 20 mM sodium phosphate, 10 mM EDTA, pH 7 at 4° C. The dialyzed antibody solution were added to 250 µl gel immobilized Papain, pre-equilibrated and suspended in 20 mM Cysteine/HCl, 20 mM sodium phosphate pH 7. The reaction were incubated at 37° C. with shaking over night, followed by centrifugation for removal of the gel immobilized Papain. Fab fragments were purified by passing the supernatants through protein A columns. The eluates were dialyzed against PBS and up-concentrated by using Spectrum gel/absorbent (Spectrum Laboratories, Cat. No.: 292600). The Fab fragments were analyzed by SDS-PAGE and the concentrations were determined by $OD_{280}$ measurements.

Example 2

In the present Example the isolation, screening, selection and banking of clones containing cognate $V_H$ and $V_L$ pairs expressed as Fabs or antibodies with anti-vaccinia virus specificity was illustrated.

Donors

Twelve donors were recruited from a smallpox vaccination program of British first line responders in collaboration with the Health Protection Agency (HPA), United Kingdom. The donors included both primary and secondary vaccinia virus-immunized individuals. Blood was withdrawn in range of 9 to 21 days after vaccination. The B cell fraction was recovered by anti-CD19 MACS column purification and the sub-population of plasma blasts identified by a CD38high and CD45intermediate cell marker expression profile and single-cell sorted by FACS into 96-well plates as described in section a) of Example 1. The percentages of plasma blasts expressing anti-vaccinia virus antibodies were estimated by ELISpot (Example 1, section b). From 0 to 0.6% of the total plasma cells were specific, and plasma cells from the top five donors (0.3-0.6%) were used to isolate cognate $V_H$ and $V_L$ coding pairs. All the selected donors belonged to the group of secondary immunized donors.

Isolation of Cognate $V_H$ and $V_L$ Coding Pairs

The nucleic acids encoding the antibody repertoires were isolated from the single cell-sorted plasma cells by multiplex overlap-extension RT-PCR (Example 1, section c). The multiplex overlap-extension RT-PCR creates a physical link between the heavy chain variable region gene fragment ($V_H$) and the full-length light chain (LC). The protocol was designed to amplify antibody genes of all $V_H$- gene families and the kappa light chain, by using two primer sets, one for $V_H$ amplification and one for the LC amplification. Following the reverse transcription and multiplex overlap-extension PCR, the linked sequences were subjected to a second PCR amplification with a nested primer set.

Each donor was processed individually, and 400 to 1200 overlap products were generated by the multiplex overlap-extension RT-PCR. The generated collection of cognate linked $V_H$ and $V_L$ coding pairs from each donor were pooled and inserted into a Fab expression vector as described in Example 1 section d). The generated repertoires were transformed into E. coli, and consolidated into ten 384-well master plates and stored.

Screening

Fab-fragments were obtained starting from the master plates, and screened against inactivated IHD-W and Lister strain as well as against the individual recombinant antigen proteins A33R, VCP and B5R as described in Example 1, section e). Several hundred secondary hits were sequenced and aligned. The majority fell in clusters of two or more members, but there were also clones that only were isolated once, so-called singletons. Representative clones from each cluster and the singletons were subjected to validation studies as described in Example 1, section e).

A total of 89 clones passed the validation. These are summarized in Table 5. Each clone number specifies a particular $V_H$ and $V_L$ pair. The IGHV and IGKV gene family is indicated for each clone and specifies the frame work regions (FR) of the selected clones. The amino acid sequence of the complementarity determining regions (CDR) of an antibody or Fab-fragment expressed from each clone are shown, where CDRH1, CDRH2, CDRH3 indicate the CDR regions 1, 2 and 3 of the heavy chain and CDRL1, CDRL2 and CDRL3 indicate the CDR regions 1, 2 and 3 of the light chain (definitions according to Kabat et al. 1991, Sequences of Proteins of Immunological Interest, 5th edn. US Department of Health and Human Services, Public Health Service, NIH.). Finally, the antigen specificity of the antibody or Fab-fragment expressed from the $V_H$ and $V_L$ coding pair contained in the clones is indicated. The antigen specificity was either identified according to the binding properties analyzed during validation, by binding to in vitro translated antigens, or by Western blotting. The in vitro translated approach identified H31, A56R, and D8L as target proteins. Un-identified antigens targeted by antibodies produced from the selected clones using Western blotting, were assigned a letter from B to L according to migration properties in SDS-PAGE (Example 1, section g. subparagraph "Characterization of the antigen specificity of the individual antibodies"). Clones indicated as reactive against antigen A in Table 5, were positive in ELISA and FLISA screens against the IHD-W and/or Lister strain, but did not interact with a particle associated antigen detectable by Western blotting. Where no particular antigen is indicated, no further analysis with respect to binding reactivity has been performed, antibodies expressed from these clones are however reactive against the IHD-W and/or Lister strain.

The complete variable heavy and light chain sequence can be established from the information in Table 5. The only exception is clone 02-291, since this clone carry an 11-codon insertion in the so-called hyper variable region 4 (framework region 3) of the heavy chain. For this reason the complete heavy chain amino acid sequence is given here for this particular clone:

QVQLVQSGAEVKKPGYSVKVSCQASGLTFSNYRVSWVRQAPGQGLEWMGG

IIPIFGTTNYAQKFQGRVTISADRSPSRVTSLADKSTITVYMELSSLRSE

DTAVYYCARSRGSQDYYGMDVWGQGTTVTVSS.

TABLE 5

| Clone | IGHV gene | CDRH1<br>3  3<br>1abc2345 | # | CDRH2<br>5         6<br>012abc3456789012345 | # | CDRH3<br>9         0           0<br>234567890abcdefghijklmno123 | # | IGKV gene |
|---|---|---|---|---|---|---|---|---|
| 02-029 | 1-24 | E---LAMH | 50 | GFDP--EDGEAVYAQGFQG | 139 | CATDVWRRTPEGGTDWF-------DPW | 228 | 3-11 |
| 02-031 | 4-34 | G---FHWS | 51 | EIN---HSGSTNYNPSVKS | 140 | CAGSRSFDLLTAYDLFHRKGNAM-DVW | 229 | 1-39 |
| 02-037 | 6-1 | NNI-ASWN | 52 | RTYYR-SKWYDDFALSVKG | 141 | CARGDVLRYF--------------DYW | 230 | 1-5 |
| 02-058 | 3-30 | R---YGMH | 53 | FLSF--DERNKFYPDSLKG | 142 | CAKGGLGTNEF-------------DHW | 231 | 1-5 |
| 02-086 | 5-51 | T---YWIG | 54 | IIYP--GDSDTKYSPSFQG | 143 | CATLPRYDAYGARIR---------DYW | 232 | 1D-33 |
| 02-089 | 1-2 | G---HYMH | 55 | WINP--SSGGTNYAQKFQG | 144 | CARYCSSPTCS-------------IVW | 233 | 3-20 |
| 02-112 | 2-5 | TSG-VGVD | 56 | LIY---WDDDKRYSPSLKS | 145 | CAHSSQRVVTGL------------DFW | 234 | 1-39 |
| 02-113 | 2-70 | TSG-MCVS | 57 | FID---WDDDKYYTTSLKT | 146 | CARIRTCYPDLYGDYNDAF-----DIW | 235 | 1D-33 |
| 02-147 | 3-7 | K---YWMS | 58 | NINQ--EGSAKHYVDSVKG | 147 | CARAADYGDY--------------VRP | 236 | 2-28 |
| 02-156 | 3-30 | S---YGMH | 59 | LISY--HGNTKYYADSVKG | 148 | CAKHVAAGGTL-------------DYW | 237 | 2-24 |
| 02-159 | 1-46 | N---YYIH | 60 | IINP--SGGSTTYAQRFQG | 149 | CARVIRKYYTSSNSYLTEQAF---DIW | 238 | 1-39 |
| 02-160* | 3-9 | D---YAMH | 61 | GCSW--NSGFISYADSVKG | 150 | CVKETVAGRRGAF-----------DYW | 239 | 1-39 |
| 02-166 | 4-34 | G---YYWT | 62 | EIN---HSANTDYKPSLKS | 151 | CARGREWPSNF-------------DSW | 240 | 3-11 |
| 02-169 | 5-51 | T---YWIG | 63 | IIYP--GDSDTRYSPSFQG | 152 | CARRGSTYYY--------------DTW | 241 | 1-39 |
| 02-172 | 3-21 | S---YTMN | 64 | AITS--STTYIYYADSVKG | 153 | CASKPYGGDFG-------------SYW | 242 | 1-5 |
| 02-183 | 5-51 | K---YWIG | 65 | IIYP--EDGDTRYSPAFQG | 154 | CARPPSNWDESF------------DIW | 243 | 1-17 |
| 02-186 | 1-3 | N---YAVH | 66 | WINV--GNGQTKFSQRFQG | 155 | CARDPTQWLLQGDVYDM-------DVW | 244 | 2-30 |
| 02-188 | 4-30-4 | SGD-YYWN | 67 | NIY---STGSTYYDPSLQN | 156 | CAREAWLGEPLLLGDDAF------DIW | 245 | 1-17 |

TABLE 5-continued

| | | | | | | | |
|---|---|---|---|---|---|---|---|
| 02-189 | 3-30 | K---YYMH 68 | TISY--DVKNKDYADSVKG | 157 | CARDGAGEWDLLMRRDF-------DYW | 246 | 1-39 |
| 02-195 | 1-18 | T---YGIS 69 | WISA--WDGNTKYGEKFQD | 158 | CARDPARRPRSGYSVF--------EYW | 247 | 3-15 |
| 02-197 | 4-4 | SN--NWWS 70 | EIY---HSGNTNYNPSLQS | 159 | CARDNRQSSSWVEGFFYYYGM---DVW | 248 | 3-20 |
| 02-201 | 1-46 | K---YYIH 71 | MINP--SGGTTTYYAQKFQG | 160 | CARLRLGATIGRD-----------DYW | 249 | 2-28 |
| 02-203 | 4-30-4 | RGD-FYWS 72 | YIY---YTGSTYYNPSLKS | 161 | CARDRASSGYDSRVWF--------DPW | 250 | 1D-33 |
| 02-205 | 3-30 | D---YTTH 73 | IVLY--DGKNKNYADSVRG | 162 | CARTYRVYAKFDPF----------DVW | 251 | 3-20 |
| 02-211 | 3-9 | D---YAMH 74 | GISW--NSEYIGYEDSVKG | 163 | CGKGVPGRRGYI-----------EDW | 252 | 1-39 |
| 02-214* | 3-9 | D---YAMH 75 | TISW--NSGFIDYADSVKG | 164 | CVKDNIAGRRGSF----------DSW | 253 | 1-39 |
| 02-215 | 1-2 | D---YYIH 76 | WINP--NFGGTDYAQKFQG | 165 | CARDYIRATGATPSKYFIYYYGM-GVW | 254 | 1-27 |
| 02-219 | 1-18 | S---YAIA 77 | WISA--YNGNTDYAQKFQG | 166 | CARARRVTNSPNNWF---------DPW | 255 | 1-39 |
| 02-225 | 4-34 | G---YYWG 78 | EIN---HSGSANYHPSLKS | 167 | CARAGERSGSGSFVLGRF------DFW | 256 | 1-39 |
| 02-229 | 3-49 | D---YAVS 79 | LIRSRHYGAKTQFAASVQG | 168 | CTNTSSLAVA--------------GNW | 257 | 4-1 |
| 02-232 | 4-39 | SRN-YYWG 80 | TIY---YTGRTYYNPSLKN | 169 | CARIPQQRVNYF-----------DYW | 258 | 1-5 |
| 02-235 | 4-39 | SSTNYYWG 81 | TVY---LSGRAYYNPSLKS | 170 | CARLPGQRTTFF-----------DYW | 259 | 1-5 |
| 02-237 | 6-1 | TST-AAWN 82 | RTYYR-SRWRNDYAGSVRS | 171 | CARGRRFEDDAF-----------DIW | 260 | 1-39 |
| 02-238* | 3-9 | D---YAMH 83 | GINW--NSGNIVYADSVKG | 172 | CVKDSVAGRRGGF----------DHW | 261 | 1-39 |
| 02-242 | 1-f | E---YYIH 84 | LVDP--EDGEPIYAEKFQG | 173 | CATRDGDF----------------DHW | 262 | 1-16 |
| 02-243 | 5-51 | S---YWIS 85 | IIYG--GDSDTKYSPSFQG | 174 | CVRHGTRYSFGRSDII--------DIW | 263 | 1-17 |
| 02-246 | 5-51 | S---YWIA 86 | IIFP--GDSDTRYSPSFQG | 175 | CTKTPARGAYGDYIS---------GSW | 264 | 1D-33 |
| 02-250* | 3-9 | D---FAMH 87 | GVSW--NSDVINYSDSVKG | 176 | CAKSTKAVRRGSF----------DYW | 265 | 1-39 |
| 02-267 | 1-69 | D---YAIS 88 | GIIP--VFGTPNYAQQFQG | 177 | CARGGKLYEGNGYYSFHYF-----DYW | 266 | 1D-33 |
| 02-269 | 2-5 | STG-VGVG 89 | LIY---WDDEERYSPSLKN | 178 | CAHTELAF----------------DYW | 267 | 1D-33 |
| 02-271 | 1-69 | S---YAIN 90 | SIIP--IFATTNYAQRFQG | 179 | CARVKGTQNYYGM----------DVW | 268 | 1-5 |
| 02-274 | 4-34 | G---YYWS 91 | EVN---HSGSTNYNPSLRS | 180 | CHYYDSTGYYVS-----------DFW | 269 | 1-16 |
| 02-286 | 1-18 | G---YGIS 92 | WITY--DKGNTNHAQKFRG | 181 | CARGVVLIQTILF----------DYW | 270 | 1-39 |
| 02-290 | 1-69 | N---SAIN 93 | GVVP--IYDTSHYAQKFKG | 182 | CARTVLDSGAYSYY----------DSR | 271 | 1-5 |
| 02-291 □ | 1-69 | N---YRVS 94 | GIIP--IFGTTNYAQKFQG | 183 | CARSRGSQDYYGM----------DVW | 272 | 1-5 |
| 02-294 | 3-23 | N---YAMS 95 | AISG--SGGKTYHAHSVRG | 184 | CAKLRDSSVYSAYVFRVIF-----DGW | 273 | 1D-33 |
| 02-295 | 3-11 | D---NYMN 96 | YISS--TSGSIYYADSVKG | 185 | CATLTVASTY--------------DYW | 274 | 2-30 |
| 02-297 | 3-9 | D---YAMH 97 | GLNW--NGANIRYADSVKG | 186 | CVKDTVALLTSRGGCM--------DVW | 275 | 1-12 |
| 02-302 | 2-5 | TSG-VGVG 98 | LIY---WDDDKRYSPSLKS | 187 | CAHSPPHGG---------------DYW | 276 | 1D-33 |
| 02-303 | 3-30 | T---YGMH 99 | FISS--DGSTKYYADSVKG | 188 | CAKGLSQALNYYGSGS--------PFL | 277 | 3-20 |
| 02-335 | 3-30 | N---YGIH 100 | FISY--DGSKKYYVDSVKG | 189 | CAKDRGVSAWYPRDAF--------DIW | 278 | 1-39 |
| 02-339 | 4-59 | S---DNWS 101 | YIY---KTGSTNYNPSLKS | 190 | CARVPLIEAGITIFAKIGAF----DIW | 279 | 3-20 |
| 02-349‡ | 5-51 | S---FWIG 102 | VTYP--GDSDTRYSPSFQG | 191 | CARGSPMIKFYF-----------DYW | 280 | 3-20 |
| 02-351 | 3-9 | N---YAMY 103 | GIIW--NSEYIGYADSVKG | 192 | CARATGAGRRNPL----------DYW | 281 | 1-39 |
| 02-431 | 1-46 | S---YYMH 104 | LINP--SSGTTSYAQNFQG | 193 | CARPYRSYSSSPQ----------DYW | 282 | 3-20 |
| 02-437 | 4-31 | SPG-YYWN 105 | YIY---YSGSTNYNPSLKS | 194 | CARYYYSSGPKF-----------DYW | 283 | 1-12 |
| 02-446 | 1-69 | S---FAIS 106 | SIIP--IFGTAHYAQRFEG | 195 | CARNNRPLGALFGM----------DVW | 284 | 1-9 |

TABLE 5-continued

| Clone | | | | | | | |
|---|---|---|---|---|---|---|---|
| 02-461 | 1-18 | T---YGIS | 107 | GIRV--HNGNTNYAQKFQG | 196 | CARGGFNRLV---------------DPW | 285 3-20 |
| 02-482 | 4-31 | SAG-YYWS | 108 | YIH---YTGTTYYNPSLKS | 197 | CARNTGIYLGGSPGGTRNNWF---DPW | 286 1-39 |
| 02-488 | 5-51 | S---YWIG | 109 | IIYP--GDSDTRYSPSFQG | 198 | CARQQAKTLYYDSSGSKSAF----DIW | 287 1-5 |
| 02-515 | 4-31 | SGG-YYWS | 110 | YIH---YSGSTYYNPSLKS | 199 | CARVRGNIVATTAFYYYYGL----DAW | 288 1-12 |
| 02-516 | 3-11 | D---YYMS | 111 | YTNL--FTGYTNYADSVKG | 200 | CAKFDYGEGAYHF-----------DFW | 289 1D-12 |
| 02-517 | 4-31 | GA--YHWS | 112 | YIY---YTGNTYFNPSLKS | 201 | CARDPIALPGRGVF----------DYW | 290 3-20 |
| 02-520 | 4-34 | A---YYWS | 113 | EIS---HSGSTHYNPSLNS | 202 | CSSGYYFAGGEF------------DYW | 291 1-12 |
| 02-526 | 3-49 | D---YTNS | 114 | FIRGKKFGGTKDYAASVKG | 203 | CTRDRGYSDHTGLYTRFGF-----DSW | 292 2-28 |
| 02-532 | 1-69 | D---HSIG | 115 | KIIP--IYGRANYAQKFQG | 204 | CARWRGGYSGYGDYF---------DSW | 293 1-39 |
| 02-536 | 4-4 | SS--HWWN | 116 | EIY---HSGSTNYNPSLKS | 205 | CARDPQKPRQHLWPNPYYYSGM--DVW | 294 1-5 |
| 02-551 | 1-69 | Y---YAIN | 117 | GIVP--MVGPADYAEKFRG | 206 | CARGRSWRGYL-------------DYW | 295 3-20 |
| 02-559 | 1-46 | N---YYMH | 118 | LINP--SGDSTTNAQKFQG | 207 | CARDYGDYCGGDCPYDAF------DIW | 296 1-27 |
| 02-572 | 1-69 | S---FGIS | 119 | GIIP--IFGTPNYSLKFQD | 208 | CARDKGESDINGWQTGAFYYGM--DVW | 297 1-12 |
| 02-575 | 2-26 | NDR-MGVS | 120 | HIF---SNDERSHSSSLKS | 209 | CARIDSVGWPSSHYYGM-------DVW | 298 1-12 |
| 02-586 | 4-59 | S---YYWS | 121 | YIF---YSGNTNYNPSLKS | 210 | CARDRITGYDSSGHAF--------DIW | 299 1-5 |
| 02-589 | 4-34 | G---YYWT | 122 | EIN---QNGRSNHNPSLKS | 211 | CARGGKFCGSTSCFTEGRL-----DYW | 300 1-39 |
| 02-607 | 3-30 | S---YGMH | 123 | VISY--DGRYKFYANSVKG | 212 | CAKDSGRYSSLGHYYYYGM-----DVW | 301 1-39 |
| 02-611 | 5-51 | N---YWIG | 124 | IIHP--GDSETRYSPSFQG | 213 | CARGYYYDTSGYRPGSF-------QHW | 302 1-5 |
| 02-612 | 3-30 | T---YTMH | 125 | VISY--DGTNKYHTDSVKG | 214 | CARPLFYGAGDAF-----------DIW | 303 1-39 |
| 02-614 | 1-69 | N---YAII | 126 | EIIP--KFGTANYAQKFQG | 215 | CADWVVGNYNGL------------DVW | 304 3-20 |
| 02-617 | 1-46 | N---YYVH | 127 | LINP--SAGKTTYAQRFQG | 216 | CAREGKHDFWRGYFSPLGM-----DVW | 305 3-20 |
| 02-621 | 1-69 | S---HGVN | 128 | GIIP--VFGTTNYAQSLQG | 217 | CATARNSSNWYEGHYYL-------AHW | 306 1D-33 |
| 02-626 | 4-30-4 | TGD-YYWS | 129 | YVF---NSGSTYYNPSLQS | 218 | CANMVVVATQPKNWF---------DPW | 307 1-39 |
| 02-628 | 4-30-4 | SGY-YYWN | 130 | YID---YRGTTYYSPSFKS | 219 | CASYGSGMGSEYYF----------GHW | 308 1-39 |
| 02-632 | 1-2 | G---YYIH | 131 | RINP--ITDVTNYAQIFQG | 220 | CGRVGREAFYYYGM----------DVW | 309 1-9 |
| 02-633 | 1-2 | A---YYIH | 132 | RINP--DSGGTDFSQKFQG | 221 | CARASRRLTTHNYF----------DGW | 310 1-16 |
| 02-634 | 3-48 | T---YEMS | 133 | YIGS--GGVTIYYADSVKG | 222 | CARVRGGRYF--------------DYW | 311 3-20 |
| 02-640 | 5-51 | T---YWIA | 134 | IIWP--VDSDTRYSPSFQG | 223 | CASGSGYDSYYNM-----------DVW | 312 1-39 |
| 02-643 | 7-4-1 | S---YAMN | 135 | WINT--NGNPTYAQGFTG | 224 | CARDSSTVTGLMTEYNWF------DPW | 313 1-39 |
| 02-649 | 4-31 | SGP-YYWS | 136 | YSS---NRGIAYYNPSLKS | 225 | CATEKGSGGDVGKF----------DNW | 314 1-39 |
| 02-650 | 1-69 | S---NPVS | 137 | GIIP--FAQKVLGAORVRD | 226 | CATGQQLYSL--------------HYW | 315 2-30 |
| 02-651 | 1-2 | D---YYLH | 138 | RINP--KSGDTHHVQKFQG | 227 | CAREGPQFYYDSGDYYSAHSPGDFDHW | 316 1-39 |

| Clone | CDRL1<br>2      3      3<br>45678901abcdefghi234 | # | CDRL2<br>5<br>0123456 | # | CDRL3<br>8   9<br>89012345a678 | # Spec. |
|---|---|---|---|---|---|---|
| 02-029 | RASQSVRR---------SLA | 317 | DASNRAT | 406 | CLQRSNWP-ITF | 495 H3L |
| 02-031 | RASQGISN---------SLN | 318 | GASGLES | 407 | CQQSYRTL-YTF | 496 H3L |
| 02-037 | RASQSISI---------WLA | 319 | KASTLES | 408 | CQQYNGYSEVTF | 497 B |
| 02-058 | RASQSIGN---------WLA | 320 | DASSLKS | 409 | CQQYDTYP-ITF | 498 B |
| 02-086 | QASQDISK---------YLN | 321 | DASNLET | 410 | CQQYDNLP-PTF | 499 C |

TABLE 5-continued

| | | | | |
|---|---|---|---|---|
| 02-089 | RASESVRSN--------YLA | 322 | GASSRAT | 411 | CQQYGRSP-LTF | 500B |
| 02-112 | RASQSIST---------YLN | 323 | AASSLQS | 412 | CQQSYNTP-ATF | 501A27L |
| 02-113 | QASQDIKY---------YLN | 324 | DASNLET | 413 | CQQYENVP-YTF | 502VCP |
| 02-147 | RSSKSLLHSNGYN----YLD | 325 | LASNRAS | 414 | CMQALQIP-RTF | 503G |
| 02-156 | RSSESLVNNDGNT----YLS | 326 | KISNRFS | 415 | CMQTTHIP-HTF | 504L |
| 02-159 | RASQNISN---------FLL | 327 | AASSLQS | 416 | CQQYGNP-LTF | 505A27L |
| 02-160* | RASQSINN---------YLN | 328 | AVSSLQT | 417 | CQQSFRTP-NTF | 506H3L |
| 02-166 | RASQSVDR---------YLA | 329 | DASNRDT | 418 | CQQRAIWP-PEF | 507 |
| 02-169 | RASQSIWT---------FLN | 330 | TASSLQS | 419 | CQQSFTSW-WTF | 508B5R |
| 02-172 | RASQSISN---------WLA | 331 | KASNLES | 420 | CQQYSNYP-ITF | 509B5R |
| 02-183 | RASQDISN---------DLG | 332 | LASSLQS | 421 | CLQHNSF--LTF | 510 |
| 02-186 | RSSQSLVYSDGNT----YLH | 333 | KVSNRDS | 422 | CMQGTHWP-PAF | 511A27L |
| 02-188 | RASQGIGY---------DLG | 334 | AASSLQS | 423 | CLQLHTFP-RTF | 512A27L |
| 02-189 | RASQSISN---------YLS | 335 | AASLLQT | 424 | CQQGYSTP-YTF | 513 |
| 02-195 | RASQSVSS---------NLA | 336 | GASTRAT | 425 | CHQYNYWPPLAF | 514H3L |
| 02-197 | RASQSIASA--------YLA | 337 | GASSRPT | 426 | CQQYGISP-RTF | 515H3L |
| 02-201 | RSSQSLLHSNGYN----YLD | 338 | LGSTRAS | 427 | GMQALQTP-HTF | 516H3L |
| 02-203 | QASHDVSN---------FLN | 339 | DASNLKT | 428 | CHQYDSLP-FTF | 517A27L |
| 02-205 | RASQSVSSN--------YIA | 340 | GASSRAT | 429 | CQQFGYSPRFTF | 518H3L |
| 02-211 | RASQSIRT---------YLN | 341 | AASSLQS | 430 | CQQTYITP-KSF | 519H3L |
| 02-214* | RASQTIST---------YLN | 342 | AASSLQS | 431 | CQQSYRTP-LTF | 520 |
| 02-215 | RASQGISN---------YLA | 343 | GASTLQS | 432 | CQKYDSAP-YTF | 521 |
| 02-219 | RASRSIST---------YLN | 344 | AASSLQS | 433 | CQQTYTIP-LTF | 522 |
| 02-225 | RASQSIHT---------YLN | 345 | TASNLQS | 434 | CQQSYSTL-RTF | 523L |
| 02-229 | KSSQSVLYSSNNNN---YLA | 346 | WASTRES | 435 | CQQYYKTP-PTF | 524A27L |
| 02-232 | RASQTIST---------WLA | 347 | DASSLES | 436 | CQQYNSYP-LTF | 525H3L |
| 02-235 | RASQSIST---------WLA | 348 | DASSLES | 437 | CQQYNFY--GTF | 526H3L |
| 02-237 | RASQSISN---------YLN | 349 | GASSLES | 438 | CQQSYSIP-RTF | 527 |
| 02-238* | RASLNIRN---------YLN | 350 | AASTLQI | 439 | CQQSYSMSPYTF | 528 |
| 02-242 | RASQVIGK---------YLA | 351 | ATSILQS | 440 | CQQYNSFP-LTF | 529 |
| 02-243 | RASQGIRN---------DLG | 352 | AASSLQS | 441 | CLQQNNYP-WTF | 530C |
| 02-246 | QASHDINK---------YLN | 353 | DASNLET | 442 | CQQYDNFP-YTF | 531 |
| 02-250* | RASQSINN---------YLN | 354 | AASSLHS | 443 | CQQTYIST-RTF | 532 |
| 02-267 | QASQDISN---------YLN | 355 | DASHLET | 444 | CQQYDNLP--LF | 533VCP |
| 02-269 | QASQDISF---------YLN | 356 | DASILET | 445 | CQQYDNLI--TF | 534VCP |
| 02-271 | RASQSISS---------WLA | 357 | KVSSLES | 446 | CQQYESDI-FTF | 535VCP |
| 02-274 | RASQDISN---------YLA | 358 | AASSLLS | 447 | CQQYGRYP-LTF | 536VCP |
| 02-286 | RASQSVST---------FLN | 359 | GVSNLQS | 448 | CQQSHRTP-YTF | 537VCP |
| 02-290 | RASQDVSP---------WLA | 360 | KASSLES | 449 | CQQYQTY--STF | 538VCP |

TABLE 5-continued

| | | | | | |
|---|---|---|---|---|---|
| 02-291 | RASQGISD---------WLA | 361 | KASSLES | 450 | CQQYESDS-WTF | 539VCP |
| 02-294 | QASQDISN---------YLN | 362 | DTSNLET | 451 | CQQYDNLP-FTF | 540VCP |
| 02-295 | RSSQSVVYSDGNI----YLN | 363 | QVSNRDS | 452 | CMQGTHWP-YSF | 541B5R |
| 02-297 | RASQDISS---------WLA | 364 | AASSLQS | 453 | CQQAYSFP-WTF | 542VCP |
| 02-302 | QASQDISN---------YLN | 365 | DASNLET | 454 | CQQYDNL--PTF | 543VCP |
| 02-303 | RASQSVSSL--------YVG | 366 | GTSSRAT | 455 | CQQYGTSP-WTF | 544B5R |
| 02-335 | RASQSISS---------FLN | 367 | GATTLQS | 456 | CHQSYSLP-FTF | 545 |
| 02-339 | RASQSVSS---------SYLA | 368 | RASSRAA | 457 | CQQYVASP-FTF | 546D8L |
| 02-349‡ | RASQSVSSRASQSVSSNYLA | 369 | GASTRAA | 458 | CHQYGTSP-RTF | 547 |
| 02-351 | RASQTIRN---------YLN | 370 | TASSLHS | 459 | CQQSYITP-YTF | 548 |
| 02-431 | RASQSVSNN--------NLA | 371 | GASSRAA | 460 | CQQYGSSP-YTF | 549A56R |
| 02-437 | RASQGISN---------WLA | 372 | AASSLQS | 461 | CQQANSFP-FTF | 550 |
| 02-446 | RASQGIGG---------ALA | 373 | AASTLQS | 462 | CQQLDTYP-LTF | 551 |
| 02-461 | RASQSVSSN--------YLA | 374 | GASSRAT | 463 | CQQYASSP-YTF | 552A33R |
| 02-482 | RASQSISR---------HLN | 375 | AASSLQT | 464 | CQHSSKTP-FTF | 553A33R |
| 02-488 | RASQSIST---------YLA | 376 | KASSLEP | 465 | CQQYSSY--LSF | 554A27L |
| 02-515 | RASQGVSN---------WVA | 377 | AASSLQS | 466 | CQQANGFL-WTF | 555 |
| 02-516 | RASQGIST---------FLA | 378 | AASSLQS | 467 | CQQAHSFP-VTF | 556A56R |
| 02-517 | RASQSVTSN--------YLA | 379 | GASNRAT | 468 | CQQYGSSP-LTF | 557 |
| 02-520 | RASQGIST---------WLA | 380 | AASTLQH | 469 | CQQANSFP-RTF | 558A |
| 02-526 | RSSQSLLHSNGYN----YLD | 381 | LGSNRAS | 470 | CMQSLQT--VTF | 559B5R |
| 02-532 | RASQSISN---------YLN | 382 | AASRLQS | 471 | CQHSYETPPYTF | 560 |
| 02-536 | RASQSLNN---------WLA | 383 | DASSLQS | 472 | CQQYNFYP-WTF | 561 |
| 02-551 | RASQSVSNN--------YLA | 384 | GASSRAT | 473 | CQQYGGSP-QTF | 562A56R |
| 02-559 | RASQGIFN---------YLA | 385 | GASTLRS | 474 | CQKYNSAP-LTF | 563 |
| 02-572 | RASQNIGN---------WLA | 386 | SASSLQN | 475 | CQQANSFP-VTF | 564 |
| 02-575 | RASQDIIS---------WLA | 387 | AASSLQS | 476 | CQQTHSFPPWTF | 565 |
| 02-586 | RASQSIYI---------WLA | 388 | DASSLES | 477 | CQQYHHYS-PTF | 566A |
| 02-589 | RASQSISR---------SLN | 389 | AASTLQS | 478 | CQQSYSTL-RTF | 567L |
| 02-607 | RASQPISS---------FLN | 390 | AASSLQS | 479 | CQQGYSTP-PTF | 568A |
| 02-611 | RASQSISS---------WLA | 391 | HAFSLEG | 480 | CQQYDSYP-YTF | 569 |
| 02-612 | RASQSFNG---------YLN | 392 | AASTLQS | 481 | CQQSYSTP-RTF | 570 |
| 02-614 | RASQTVIST--------YLA | 393 | GASSRAT | 482 | CQQYSDS--LTF | 571 |
| 02-617 | RASQSVSSG--------SLD | 394 | GASNRAS | 483 | CHQYGGAQ-GTF | 572 |
| 02-621 | QASQDISN---------YLN | 395 | DASNLET | 484 | CQQYDTLPPITF | 573 |
| 02-626 | RASQSISS---------YLN | 396 | AASSLQS | 485 | CQQSHSSP-WTF | 574 |
| 02-628 | RASQSIRS---------YLN | 397 | GASSLQS | 486 | CQQSYLAP-WTF | 575 |
| 02-632 | RASQGISS---------YLV | 398 | AASTLES | 487 | CQQFNNYP-YTF | 576 |
| 02-633 | RASQAISN---------YLN | 399 | GAFILES | 488 | CQQYHTYP-FTF | 577J |

TABLE 5-continued

| | | | | | |
|---|---|---|---|---|---|
| 02-634 | RASQSVSST--------YLA | 400 | GASNRAT | 489 CQKYGRSPTWTF | 578 |
| 02-640 | RASQSISN---------HLN | 401 | VASSLQG | 490 CQQGFTTP-ITF | 579J |
| 02-643 | RASQSISS---------YLN | 402 | AASSLQS | 491 CQQSYSTP-YTF | 580 |
| 02-649 | RANQSIDD---------YLH | 403 | DASTLHS | 492 CQQSYTIPLWTF | 581 |
| 02-650 | RSSQSLVYADGDT----HLN | 404 | HVSNRDA | 493 CMQGTHWP-PTF | 582 |
| 02-651 | RASQSITN---------CLN | 405 | GASTLQS | 494 CQQSDSTP-YTF | 583 |

IGHV and IGKV gene names were assigned according to the official HUGO/IMGT nomenclature (IMGT; Lefranc & Lefranc, 2001, The Immunoglobulin FactsBook, Academic Press). Numbering and alignments are according to Chothia (Al-Lazikani et al. 1997 J. Mol. Biol. 273:927-48).
*) These clones were isolated from different donors but utilize highly similar VDJ and VJ rearrangements.
◘) These two clones carry an 11-codon insertion in the so-called hypervariable region 4 (framework region 3).?
†) This clone carries an eight-codon insertion in CDRL1.

Mirroring the Humeral Immune Response

Figures 7, 8:
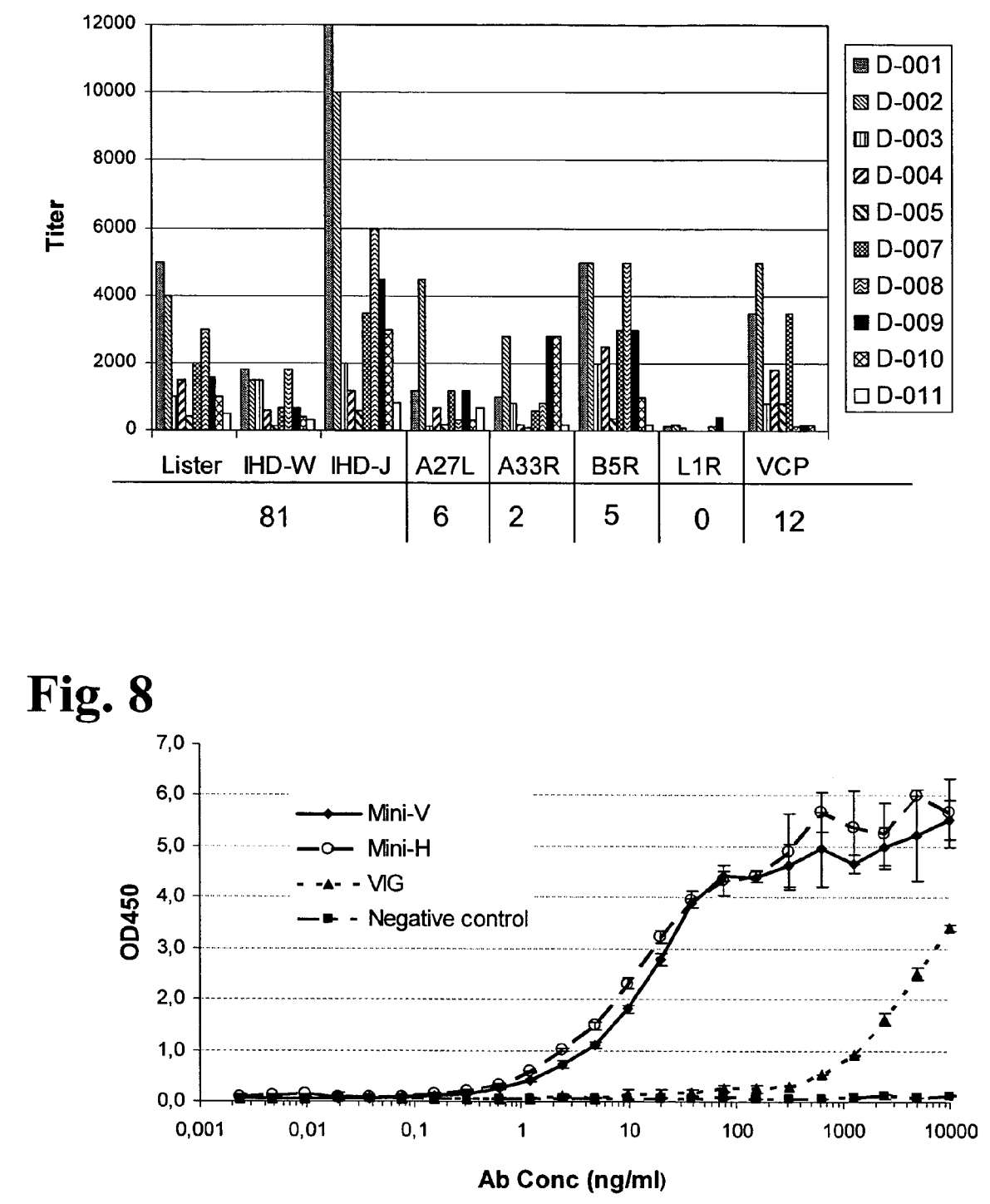

In order to illustrate that the cognate $V_H$ and $V_L$ coding pairs isolated and selected as described above mirrors the natural humeral immune response raised upon challenge with vaccina virus, serum samples from ten of the twelve donors were tested for reactivity against three virus strains (Lister, IHD-W and IHD-J), and five recombinant antigens (B5R, VCP, A27L, A33R and L1R). The antibody titers were determined as the minimum sera dilution required for a four-fold background signal and the determined values are displayed in FIG. 7. The titers varied among the different antigens and donors, this is likely to reflect differences in immunogenicity, efficient up-take of the vaccinia virus, time from vaccination to blood withdrawal, primary and secondary response, etc. Comparison of the specific antibody titers from the donors and identified cognate Fabs/antibodies with the same reactivity, suggested that the antibody diversity recovered in the present experiment included the specificities present in the collected serum samples. The analysis thereby supports the claim that the identified anti-vaccinia virus repertoire reflects the specificity of the natural humeral immune response.

The vaccinia virus-specific clones also display a high diversity. All immunoglobulin variable region heavy chain gene families (IGHV), including IGHV7, as well the immunoglobulin kappa light chain gene families (IGKV) 1-4, were found among the validated clones. The V-gene families for each isolated and selected clone are indicated in Table 5. The heavy chain V-gene usage correlated with what has been found previously in human antibody repertoires, with a frequent usage of the IGHV3, IGHV1 and IGHV4 families. The light chain V-gene usage was dominated by the IGKV1 family, mainly due to the frequent usage of the IGKV1-39 gene. This gene is also among the most frequently used light chain V-genes in the human immunoglobulin repertoire. As a whole, the IGKV1 genes make up 75% of the repertoire. The only other IGKV gene of prominent usage in the isolated repertoire was the IGKV3-20, which also is the most frequently expressed light chain gene in humans. The IGKV families 5 and 6 were the only families not represented in the repertoire. IGKV5 and 6 are very rarely utilized in a human antibody response, or may not even consist of functional IGKV genes (de Wildt et al. 1999, J. Mol. Biol. 285:895-891; Lefranc & Lefranc 2001, The Immunoglobulin FactsBook, Academic Press). In conclusion, the diversity of the isolated repertoire is evidence of an unbiased recovery of V-genes by multiplex overlap-extension RT-PCR, indicating that the isolated antibodies mirror the diversity of the humeral response in humans.

Further, due to the cognate pairing of the $V_H$ and $V_L$ coding sequences representing the $V_H$ and $V_L$ pairing originally present in the donor from which such a cell is derived, the affinity of the humeral immune response raised upon vaccination with vaccinia virus is also considered to be mirrored by the isolated antibodies.

Generation of a Cell Bank of Individual Antibody Expressing Members

A subset of 47 unique cognate $V_H$ and $V_L$ coding pairs corresponding to clone nr $O_2$-029, 02-031, 02-037, 02-058, 02-086, 02-089, 02-112, 02-113, 02-147, 02-156, 02-159, 02-160, 02-169, 02-172, 02-186, 02-188, 02-195, 02-197, 02-201, 02-203, 02-205, 02-211, 02-225, 02-229, 02-232, 02-235, 02-243, 02-271, 02-286, 02-295, 02-297, 02-303, 02-339, 02-431, 02-461, 02-482, 02-488, 02-516, 02-520, 02-526, 02-551, 02-586, 02-589, 02-607, 02-628, 02-633 and 02-640 of Table 5 were selected for expression as complete antibodies. The $V_H$ and $V_L$ coding pairs were selected from the 89 validated antibodies, according to the Fab reactivity in ELISA, Western blotting, antigen diversity, and sequence diversity. The selected cognate V-gene pairs were transferred to a mammalian expression vector. The transfer process is described in Example 1 section f). The individual expression constructs were co-transfected with a Flp-recombinase expressing plasmid into the CHO-FlpIn recipient cell line (Invitrogen), followed by antibiotic selection of integrants. The transfections, selection, and adaptation to serum free culture was performed as described in Example 1, section g). The adaptation process was continued until the doubling time was below 32 hours. This was on average completed within a 4-6 week period; thereafter the individual cells lines were banked.

Example 3

In the present Example the biological activity of a mixture of monoclonal anti-VV antibodies was compared to a serum derived VIG product.

The first sixteen individual cell lines introduced into the bank generated in Example 2, were used to express monoclonal antibodies, which where purified, and characterized individually and mixed to generate the Mini-V preliminary antibody composition, a composition which was composed of a mixture of 16 monoclonal antibodies containing the cognate $V_H$ and $V_L$ pairs corresponding to clone nr 02-029, 02-031, 02-037, 02-058, 02-086, 02-089, 02-112, 02-113, 02-147, 02-156, 02-159, 02-160, 02-169, 02-172, 02-211 and 02-243 of Table 5 in Example 2. The Mini-V composition was produced to resemble a polyclonal antibody product, to verify the biological activity of such a product. In parallel, an oligoclonal composition was compiled consisting of three antibodies specific for IMV antigens as indicated by Western blotting. This oligoclonal antibody composition was termed Mini-H, and was composed of a mixture of 3 monoclonal antibodies corresponding to clone nr 02-31, 02-211 and 02-243 of Table 5.

The specific binding to inactivated Lister strain of the Mini-V and Mini-H compositions were compared to the serum derived antibodies of the five processed donors, which had been affinity purified using Protein-A columns (termed SymVIG) (FIG. 8). The direct binding analyses demonstrated at least a 100-fold increase in the specific binding activity of the recombinant antibody compositions.

The neutralizing activity of the two compositions was assayed in vitro by plaque reduction and neutralization assay as described in Example 1, section p). The anti-viral potency was indicated as the antibody concentration required for 50% reduction of viral infectivity detected as number of plaques caused by a vaccinia virus infection of a confluent monolayer of adhered cells ($IC_{50}$). Mini-V showed a 100-fold increased potency compared to SymVIG (Table 6). This correlated with the profound specific activity of Mini-V. Interestingly, Mini-H was 10-fold less potent than Mini-V, indicating superiority of a polyclonal antibody composition, including reactivity against both IMV- and EEV-particles.

TABLE 6

| Antibody composition | IMV-neutralization (μg/ml) | EEV-neutralization (μg/ml) |
|---|---|---|
| Mini-V | 0.5 | 25 |
| Mini-H | 6.25 | n.a. |
| SymVIG | 62.5 | 250 |

EEV-specific infection was detected in a plaque reduction assay as described in Example 1, section p) in the presence of 100 μg/ml of the Mini-H IMV-neutralizing antibody composition. The EEV-neutralization potency of Mini-V was only found to be 10-fold more profound than SymVIG (Table 6). The Mini-V composition only contains two EEV-specific antibodies. This is most likely the reason that the mini-V composition has a lower anti-EEV than anti-IMV activity, and this suggests that an increased proportion of anti-EEV antibodies will improve the EEV-neutralization.

The effect on vaccinia virus replication of Mini-V in vivo has been investigated using the mouse tail lesion model (see Example 1, section q). Both SymVIG and Mini-V significantly reduced the number of tail lesions (FIG. 9). A nearly complete elimination of pocks was observed with the 100 μg to 300 μg Mini-V doses, in contrast to a maximum of ~65% inhibition observed for the highest concentration of SymVIG. These experiments suggest that the in vivo specific activity of Mini-V is at least 100-fold higher than SymVIG, correlating with the in vitro neutralization and binding studies.

Example 4

The present Example illustrates the generation of a recombinant polyclonal anti-VV antibody and compares the biological activity of an anti-VV rpAb with that of a mixture of monoclonal antibodies and a serum derived polyclonal VIG product.

Generation of a Polyclonal Cell Line and Production of Anti-VV rpAb

The aim of the lead identification for the production of the recombinant polyclonal anti-VV antibody was to select a composition with the broadest possible reactivity against vaccinia virus and thus presumably also variola virus. The individual antibody members included in the anti-VV recombinant polyclonal antibody were selected based on several characteristics:

- Antigen reactivity; in principle all antigen reactivities identified in Example 2 should be represented in the composition, and the reactivity should be specific and of high affinity. Further, if possible an average of 2-3 antibodies against each identified antigen should be included.
- Biochemical properties; only antibodies with well-defined characteristics were included in the final product. The individually expressed antibodies were analyzed by reducing and non-reducing SDS-PAGE, and ion exchange-profiles. Antibodies with an aberrant biochemical behavior were subjected to detailed analysis and most likely excluded from the final composition.
- Cell line characteristics; to optimize the stability of the polyclonal cell line, individual cell lines with similar doubling times, as well as productivity after adaptation were preferred.

Twenty eight individual cell cultures expressing cognate $V_H$ and $V_L$ coding pairs corresponding to clone nr. 02-029, 02-037, 02-058, 02-086, 02-113, 02-147, 02-186, 02-188, 02-195, 02-197, 02-203, 02-211, 02-225, 02-229, 02-235, 02-286, 02-295, 02-303, 02-339, 02-461, 02-482, 02-488, 02-526, 02-551, 02-586, 02-589, 02-607 and 02-633 of Table 5 in Example 2, were selected for the generation of a polyclonal cell line. The individual cell lines were thawed and expanded at 37° C. in serum free medium in shaker flasks to reach at least $4\times10^8$ cells of each clone having a population doubling time of 21-34 hours. The viabilities were in the range of 93% to 96%, prior to mixing of the individual cell lines. Further details to the generation of the polyclonal cell line and the establishment of a polyclonal working cell bank (PWCB) are found in Example 1, section g).

The recombinant polyclonal anti-VV antibody was produced in laboratorial scale bioreactors as described in Example 1, section n) and purified as described in section o). Three batches have been produced independently from three vials from the pWCB.

The diversity of the anti-VV rpAb produced from the polyclonal cell line was analyzed by IEX chromatography using a PolyCAT column; buffer A: 25 mM sodium acetate, 150 mM sodium chloride, pH 5.0; B: 25 mM sodium acetate, 0.5 mM sodium chloride, pH 5.0 (gradient: 30-100% B). The IEX profiles of the three anti-VV rpAb batches were highly similar. Assignment of the individual peaks in the IEX profile of the anti-VV rpAb product was conducted by running the individual antibodies produced in Example 2, under identical conditions to identify the position of the peaks in the IEX profile (FIG. 10). Antibodies from two of the individual cell lines (clones 02-113 and 02-225) included in the polyclonal cell line were not found in the anti-VV rpAb. These clones produce antibodies which are reactive against VCP and antigen L, respectively. However, since there are other antibodies with similar reactivity in the composition the loss of these clones are considered acceptable for the further analysis.

Biological Activity of the Anti-VV rpAb

The reactivity of the three anti-VV rpAb batches against different vaccinia virus strains and the recombinant antigens was compared by ELISA (FIG. 11). In correlation with the highly similar IEX profiles, the three batches exert a nearly identical binding reactivity against all the tested antigens supporting a consistent antibody mixture of the produced polyclonal antibody. For this reason it was decided to pool the three batches. Further, the anti-VV rpAb batches were compared to SyinVIG and the commercial available serum derived VIG product (Cangene). In comparison to the serum derived VIG, a ~250 fold increase specific binding activity of the anti-VV rpAb batches was observed more or less independent of the target antigen.

The SYM002 anti-VV rpAb was tested in two types of plaque reduction and neutralization assays (PRNT; Example 1, section p). SYM002 anti-VV rpAb exerted a 40-fold improved specific antiviral activity as compared to the Mini-V of Example 3 and 800-fold improved specific activity than the commercial available blood derived VIG product (Cangene) (Table 6). The superior antiviral activity of Sym002 anti-VV rpAb was also observed in the modified PRNT assay detecting EEV-mediated infection. The $IC_{50}$ values obtained in the in vitro assays are connected with a high degree of uncertainty, but the presented data clearly demonstrate a superior specific activity of Sym002 anti-VV rpAb.

TABLE 6

| Antibody composition | IMV- neutralization (µg/ml) | EEV- neutralization (µg/ml) |
|---|---|---|
| Sym002 anti-VV rpAb | 0.125 | 2 |
| Mini-V | 5.0 | 10 |
| VIG (cangene) | 100 | 200 |

Figure 12:
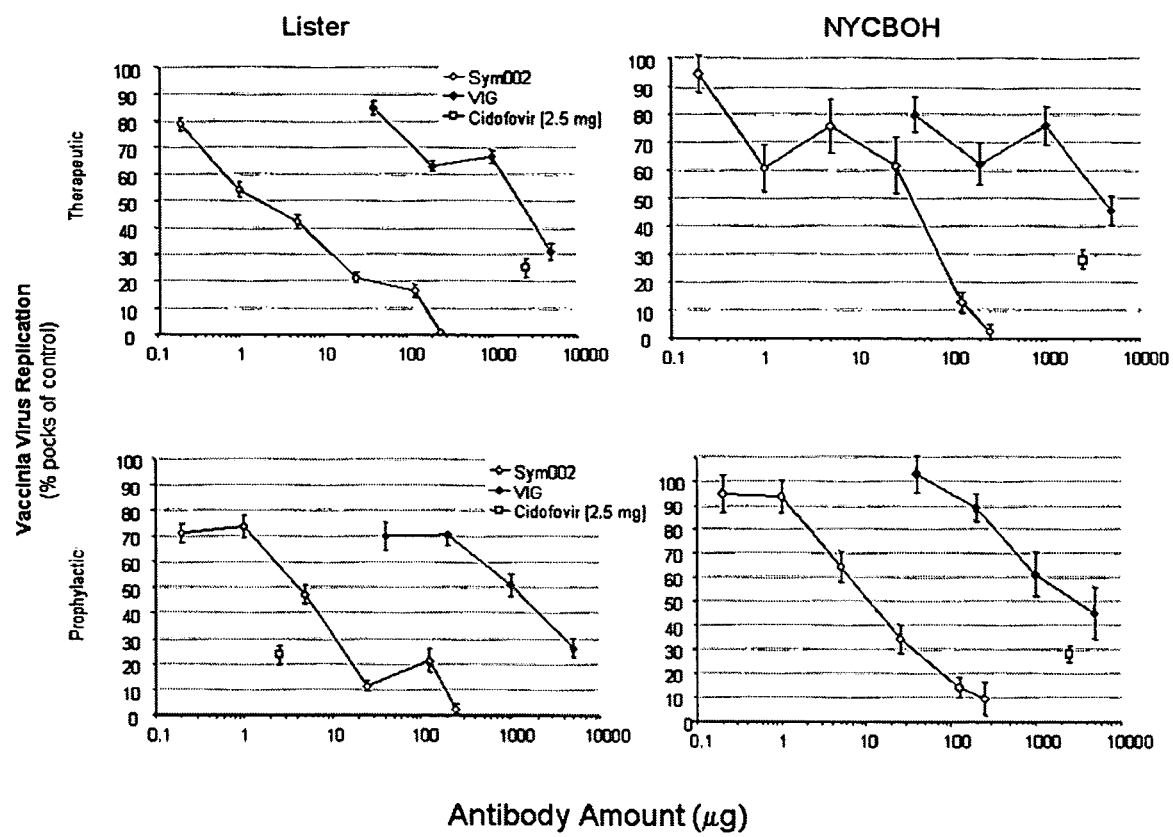
FIG. 12: Sym002 anti-VV rpAb (SYM002) inhibits vaccinia virus replication in vivo. Prophylactic (lower panel) or therapeutic (top panel) intramuscular administered Sym002 anti-VV rpAb inhibits both the Lister and NYCBOH vaccinia virus replication in vivo as assayed by the mouse tail pock model. All the four data sets showed an approximately 300-fold increased specific activity of Sym002 anti-VV rpAb as compared to VIG (Cangene).

The Sym002 anti-VV rpAb has been tested for in vivo antiviral activity using the tail lesion model challenged with either Lister of NYCBOH vaccinia virus strain. The Sym002 pre-lead product was administered intramuscularly (I.M) 24 hours prior (prophylactic) or post (therapeutic) virus challenges. All data sets demonstrated an approximately 300-fold increase specific activity of Sym002 anti-VV rpAb as compared to blood derived commercial available VIG (FIG. 12). It was anticipated that prophylactic administered Sym002 anti-VV rpAb would elicit a profound anti-virus effect and not as observed a nearly identical antiviral activity. The result is likely to reflect the limitation of the used mouse model, in which a huge amount of infectious virus particles (~$10^5$ PFU) is injected into the tail vein and thereby creating a temporary high local concentration that are giving raise to approximately 50-70 countable pocks in the untreated situation. In this scenario the temporary high concentration of virus is likely to exceed the concentration of administered antibody which thereby is more likely to influence continues spreading of virus than blocking the primary infection. If this is the dynamic of the mouse tail lesion model no profound potency of Sym002 anti-VV rpAb can be obtained by a prophylactic administration of antibody correlating with the observation. Combined the in vitro and in vivo data provide evidence for that all essential antibody reactivities required for in vitro neutralization of vaccinia virus are included in anti-VV rpAv.

Figure 13:
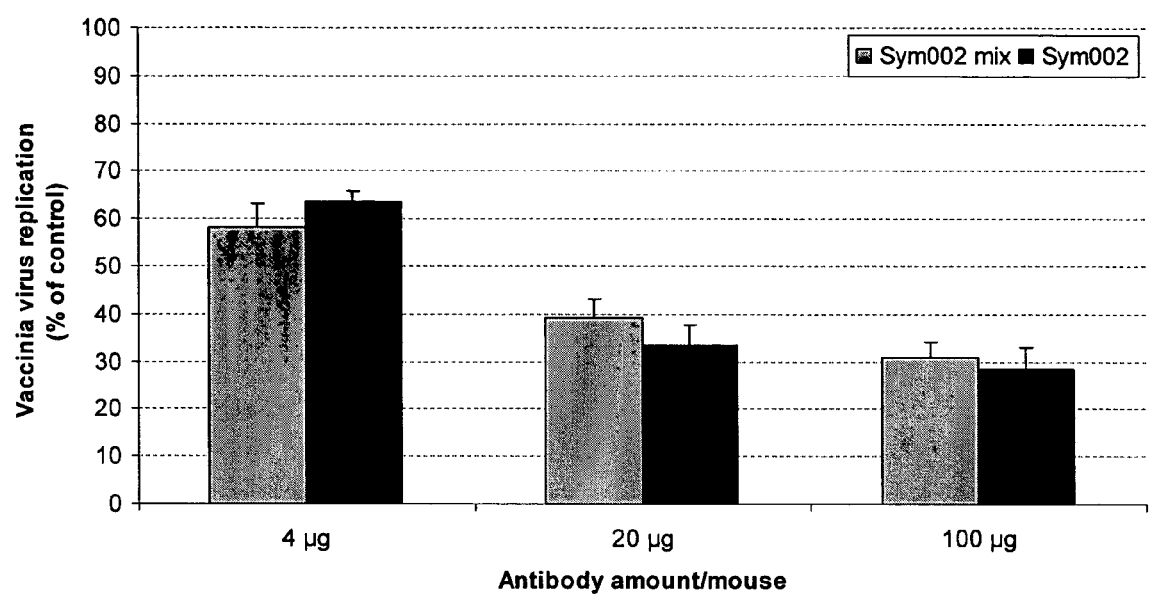
FIG. 13: Sym002 mix and Sym002 anti-VV rpAb (SYM002) have identical anti-viral potency in the mouse tail lesion model. Eight mice in each group were challenged with vaccinia virus, NYCOBH strain 24 hours prior to injection I.P. injection of the indicated amount of antibodies.

A Sym002 mix was compiled by mixing of individual purified antibodies (Example 1, section i) to obtain a more equal representation of each antibody than present in the anti-VV-rpAb produce from the pWCB (Example 4). The anti-viral activity of the two polyclonal antibody compounds was assayed in the mouse tail lesion model as described above except for that the indicated doses of antibodies were administered intraperitoneal (I.P) 24 hours post challenge with the NYCBOH vaccinia virus. Within the tested dose range we observed an identical antiviral activity of the SYM002 anti-VV-rpAb and the Sym002 mix (FIG. 13) proving that the used production method generate fully biological active polyclonal antibody product.

Example 5

Affinity of Selected Antibodies

Figure 14:
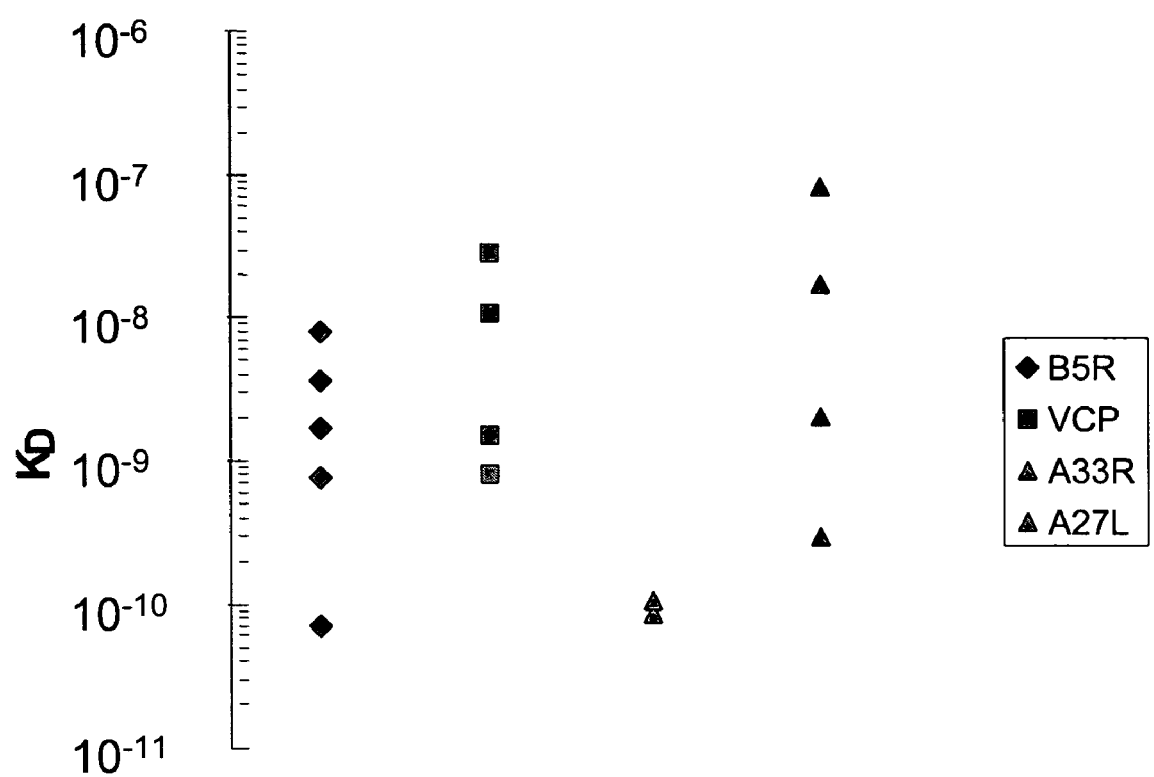
FIG. 14: Affinities of antibodies reactive against B5R, A33R, A27L, or VCP determined by surface plasmon resonance using a BIAcore 2000. The obtained affinities are in the nanomolar range indicating affinity maturated antibodies.

The binding kinetic of antibodies can be detected by surface plasmon resonance measurements e.i. by BIAcore. This method requires chemical immobilization of the antigens on a CHIP surface, restricting the analysis to the Sym002 antibodies interacting with A27L, A33R, VCP and B5R, since only these antigens were available as recombinant proteins. Fab fragments were generated from purified IgG1 antibodies by papain digestions (Example 1, section J). The kinetic measurements revealed affinities constants ($K_D$) between $10^{-8}$ to $10^{-10}$ $M^{-1}$ of the majority of the investigated antibodies (FIG. 14). The observed affinities are approaching the theoretical antibody affinity ceiling (KD at $10^{-10}$ M–1) (Foote and Eisen, 1995, Proc Natl Acad Sci USA, 92: 1254-1256) supporting that the selected antibodies repertoire mirrors the natural humeral immune response. In addition to the reported data, some of the tested antibodies did not interact with the immobilized antigen. The explanation to this observation is unknown but it might be due to sterical constrains introduced by the immobilization or that the structure of some epitopes may be denatured during either during the immobilization or the chip cleaning procedures.

What is claimed is:

1. An anti-orthopoxvirus polyclonal recombinant antibody composition, comprising two or more distinct antibody molecules binding to different orthopoxvirus epitopes, wherein each distinct antibody comprises the following:
(a) a VH CDR1 selected from SEQ ID NOs: 50-138;
(b) a VH CDR2 selected from SEQ ID NOs: 139-227;
(c) a VH CDR3 selected from SEQ ID NOs: 228-316;
(d) a VL CDR1 selected from SEQ ID NOs: 317-405;
(e) a VL CDR2 selected from SEQ ID NOs: 406-494; and
(f) a VL CDR3 selected from SEQ ID NOs: 495-583;
wherein the CDRs are combined according to Table 5.

2. The composition of claim 1, comprising two or more distinct antibody molecules binding to different epitopes of the same orthopoxvirus antigen.

3. The composition of claim 1, comprising three or more distinct antibody molecules binding to three different orthopoxvirus antigens.

4. The composition of claim 3, further comprising two or more distinct antibody molecules binding to different epitopes of the same orthopoxvirus antigen.

5. An anti-orthopoxvirus polyclonal recombinant antibody composition, comprising two or more antibodies selected from the group consisting of antibodies comprising heavy and light chain CDR1, CDR2, and CDR3 regions:

(a) SEQ ID NOs: 50, 139, 228, 317, 406, and 495;
(b) SEQ ID NOs: 52, 141, 230, 319, 408, and 497;
(c) SEQ ID NOs: 53, 142, 231, 320, 409 and 498;
(d) SEQ ID NOs: 54, 143, 232, 321, 410, and 499;
(e) SEQ ID NOs: 58, 147, 236, 325, 414, and 503;
(f) SEQ ID NOs: 66, 155, 244, 333, 422, and 511;
(g) SEQ ID NOs: 67, 156, 245, 334, 423 and 512;
(h) SEQ ID NOs: 69, 158, 247, 336, 425, and 514;
(i) SEQ ID NOs: 70, 159, 248, 337, 426, and 515;
(j) SEQ ID NOs: 72, 161, 250, 339, 428, and 517;
(k) SEQ ID NOs: 74, 163, 252, 341, 430, and 519;
(l) SEQ ID NOs: 79, 168, 257, 346, 435, and 524;
(m) SEQ ID NOs: 81, 170, 259, 348, 437 and 526;
(n) SEQ ID NOs: 92, 181, 270, 359, 448, and 537;
(o) SEQ ID NOs: 96, 185, 274, 363, 452, and 541;
(p) SEQ ID NOs: 99, 188, 277, 366, 455, and 544;
(q) SEQ ID NOs: 101, 190, 279, 368, 457, and 546;
(r) SEQ ID NOs: 107, 196, 285, 374, 463, and 552;
(s) SEQ ID NOs: 108, 197, 286, 375, 464 and 553;
(t) SEQ ID NOs: 109, 198, 287, 376, 465, and 554;
(u) SEQ ID NOs: 114, 203, 292, 381, 470, and 559;
(v) SEQ ID NOs: 117, 206, 295, 384, 473, and 562;
(w) SEQ ID NOs: 121, 210, 299, 388, 477, and 566;
(x) SEQ ID NOs: 122, 211, 300, 389, 478, and 567;
(y) SEQ ID NOs: 123, 212, 301, 390, 479, and 568; and
(z) SEQ ID NOs: 132, 221, 310, 399, 488, and 577.

6. An anti-orthopoxvirus polyclonal recombinant antibody composition, comprising antibodies comprising heavy and light chain CDR1, CDR2, and CDR3 regions:

(a) SEQ ID NOs: 57, 146, 235, 324, 413, and 502; and
(b) SEQ ID NOs: 78, 167, 256, 345, 434, and 523.

* * * * *